(12) United States Patent
Beutler et al.

(10) Patent No.: US 7,705,199 B2
(45) Date of Patent: Apr. 27, 2010

(54) COMPOSITIONS AND METHODS FOR TREATMENT OF AUTOIMMUNE AND RELATED DISEASES

(75) Inventors: Bruce Beutler, San Diego, CA (US); Koichi Tabeta, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 11/817,288

(22) PCT Filed: Mar. 2, 2006

(86) PCT No.: PCT/US2006/007420
§ 371 (c)(1),
(2), (4) Date: Aug. 28, 2007

(87) PCT Pub. No.: WO2006/094124
PCT Pub. Date: Sep. 8, 2006

(65) Prior Publication Data
US 2008/0152643 A1    Jun. 26, 2008

Related U.S. Application Data

(60) Provisional application No. 60/658,197, filed on Mar. 2, 2005.

(51) Int. Cl.
*A01K 67/027* (2006.01)
*A01K 67/00* (2006.01)
*A01K 67/033* (2006.01)
*G01N 33/00* (2006.01)
*C12N 5/07* (2006.01)
*C12N 5/10* (2006.01)
*C12N 5/00* (2006.01)
*C12N 5/02* (2006.01)

(52) U.S. Cl. .................. 800/18; 800/9; 800/3; 435/354; 435/325

(58) Field of Classification Search ........................ None
See application file for complete search history.

(56) References Cited

OTHER PUBLICATIONS

Conley, 2007, Trends in Immunology, 28: 99-101.*
Natasha Caplen et al., "Specific inhibition of gene expression by small double-stranded RNAs in invertebrate and vertebrate systems", PNAS, 2001 vol. 98 No. 17 pp. 9742-9747.
Ying Liu et al., The human homologue of unc-93 maps to chromosome 6q27—characterisation and analysis in sporadic epithelial ovarian cancer, BMC Genetics, 2002 vol. 3 No. 20 pp. 1-20.

* cited by examiner

*Primary Examiner*—Joanne Hama
(74) *Attorney, Agent, or Firm*—Hugh Wang; Thomas Fitting

(57) ABSTRACT

Compositions and methods are provided for treatment of autoimmune and other related diseases. 3d, a point mutation of the protein uncoordinated-93b (unc-93B), unc-93A, unc-93B, and unc-93C, polypeptides, nucleic acids encoding them and methods for making and using them, for example, to produce transgenic non-human animals.

14 Claims, 16 Drawing Sheets

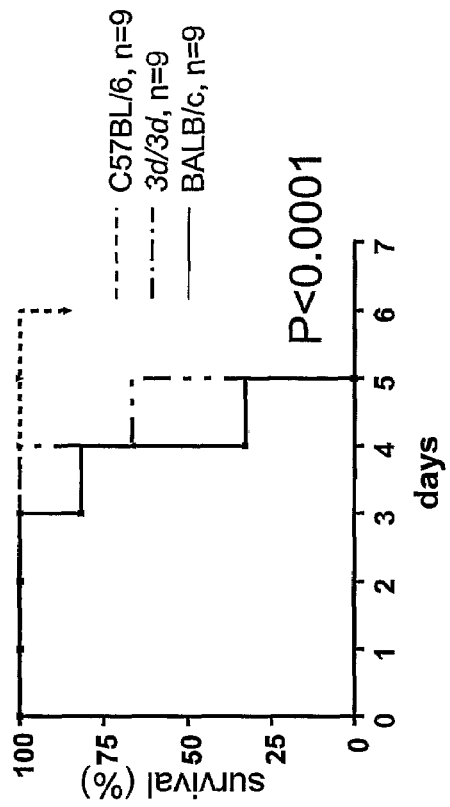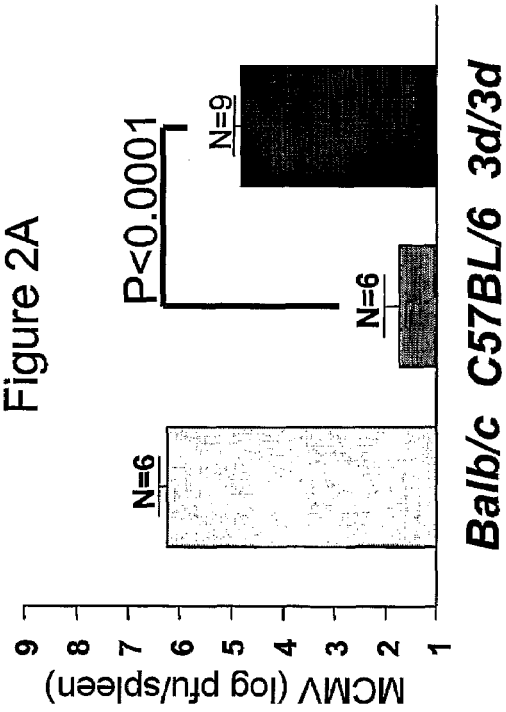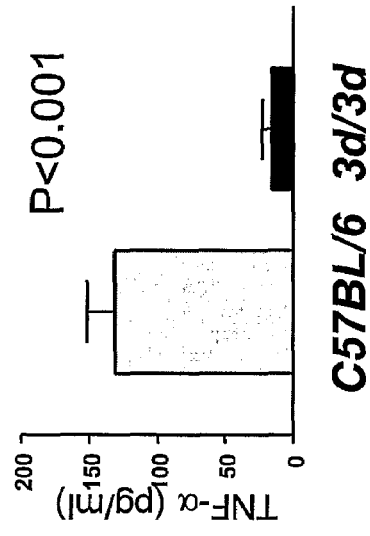
Figure 2A, Figure 2B, Figure 2C, Figure 2D, Figure 2E

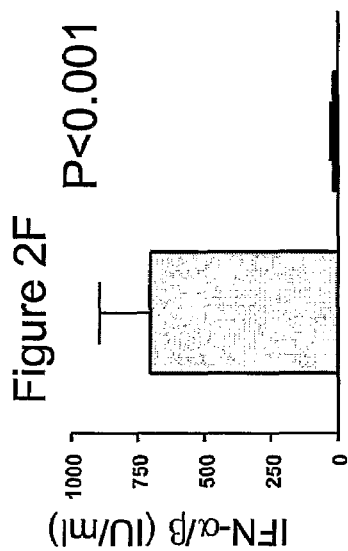
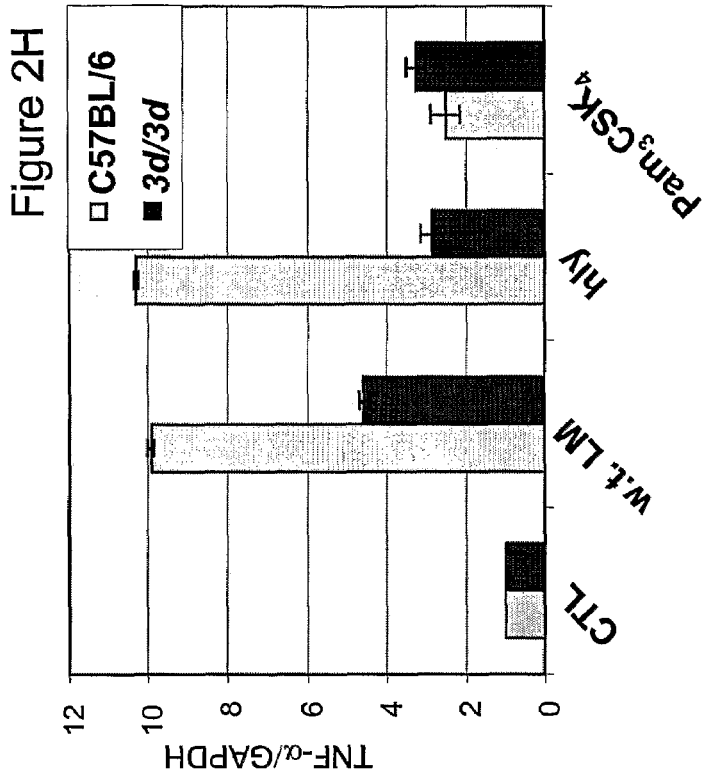
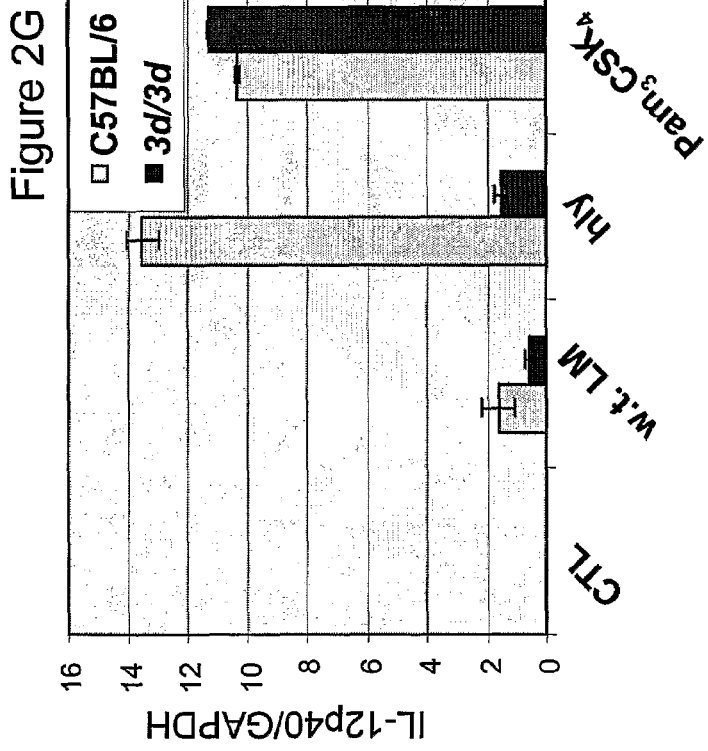

C57BL/6    C57BL/6<sup>3d/3d</sup>

Figure 7

| SNP | Allele (C57BL/6/C3H/HeN) | Distance from centromere (bp) |
|---|---|---|
| 3dSNP1 | A/G | 4215024 |
| 3dSNP2 | T/C | 5392271 |
| 3dSNP3 | G/A | 3744813 |
| 3dSNP4 | C/A | 3895073 |

| Marker | Primer( F/R) | Distance from centromere (bp) |
|---|---|---|
| 3d_1_6_f | 5′ TCGGAAGCGGTTCATCACTGACTC3′ | 4020567bp |
| 3d_1_6_r | 5′ CCAGCAGACAGACAGCTCATCGGAAG3′ | 4020796bp |

Figure 8

Unc93b (3d mutant) cDNA    (SEQ ID NO:1)

```
   1 ATGGAGGTGG AGCCTCCGCT CTACCCTGTG GCCGGGGCCG CGGGTCCTCA
  51 AGGGGATGAA GACCGGCACG GAGTTCCTGA TGGGCCAGAG GCTCCCTTGG
 101 ACGAACTCGT GGGTGCGTAC CCCAACTACA ATGAGGAGGA GGAAGAGCGC
 151 CGCTACTACC GCCGCAAGCG CCTCGGAGTG GTCAAGAACG TGCTGGCGGC
 201 CAGCACGGGT GTCACCCTTA CTTACGGCGT CTACCTGGGC CTCCTGCAGA
 251 TGCAACTGAT CCTGCACTAT GATGAGACCT ACAGAGAGGT GAAGTATGGC
 301 AACATGGGGC TGCCGGACAT CGATAGCAAG ATGCTGATGG GTATCAACGT
 351 GACGCCTATC GCTGCCCTGC TCTACACACC TGTGCTCATC AGGTTTTTTG
 401 GTACCAAGTG GATGATGTTC TTGGCTGTGG GCATCTATGC CCTCTTTGTC
 451 TCTACCAACT ACTGGGAACG CTACTACACG CTGGTGCCCT CTGCTGTGGC
 501 TCTGGGCATG GCCATTGTGC CTCTGTGGGC CTCCATGGGC AACTATATCA
 551 CCAGGATGTC CCAGAAGTAC TATGAATACT CCCACTACAA GGAGCAAGAT
 601 GAGCAGGGAC CTCAGCAGCG CCCACCACGA GGTTCCCACG CACCCTATCT
 651 CCTGGTTTTC CAGGCCATCT TCTATAGCTT CTTCCACTTG AGCTTCGCGT
 701 GTGCCCAGCT GCCCATGATT TACTTCCTCA ACAACTACCT GTATGACCTG
 751 AACCACACAC TGATCAACGT GCAGAGCTGC GGTACTAAGA GCCAAGGCAT
 801 TCTGAATGGC TTCAACAAGA CGGTCCTTCG GACGCTGCCG CGCAGCAAAA
 851 ACCTTATTGT TGTAGAGAGC GTGCTCATGG CGGTGGCCTT CTTGGCCATG
 901 CTGATGGTGC TGGGCCTGTG TGGAGCCGCT TACCGGCCCA CGGAAGAGAT
 951 CGACCTGCGC AGCGTGGGCT GGGGCAACAT CTTCCAGCTG CCCTTCAAAC
1001 ACGTGCGTGA CTTTCGCTTA CGCCATCTGG TGCCCTTCTT TATCTACAGT
1051 GGCTTTGAGG TGCTCTTTGC CTGCACTGGT TTTGCCCTGG GCTACGGCGT
1101 GTGCTCCATG GGCTGGAGC GACTGGCATA CCTGCTCATA GCTTACAGCC
1151 TGGGTGCCTC AGCCTCCTCG GTTCTGGGGC TGCTGGGACT GTGGCTGCCT
1201 CGCTCTGTCC CGCTCGTGGC TGGGGCAGGA CTGCGCCTAC TGCTCACCCT
1251 TAGCCTCTTT TTCTGGGCTC CTGCTCCTCG GGTCCTCCAG CACAGTTGGA
1301 TCTTTTACTT CGTGGCTGCC CTCTGGGGTG TGGGCAGCGC CCTCAACAAG
1351 ACCGGACTTA GCACACTCCT GGGCATCCTA TATGAAGACA AGAGAGGCA
1401 GGACTTCATC TTCACCATCT ATCACTGGTG GCAGGCCGTG GCCATCTTTG
1451 TTGTGTACCT GGGCTCCAGC TTGCCCATGA AGGCCAAGCT GGCAGTGTTG
1501 CTGGTGACCC TGGTAGCAGC AGCAGCCTCA TACCTGTGGA TGGAGCAGAA
1551 GTTGCAGCAA GGATTGGTCC CGCGGCAGCC GCGCATTCCG AAGCCACAGC
1601 ACAAAGTCCG CGGCTACCGC TACCTGGAGG AGGACAACTC GGATGAGAGT
1651 GACATGGAGG GCGAGCAGGG TCAGGGGGAC TGCGCAGAGG ACGAAGCACC
1701 ACAGGCAGGG CCCCTGGGTG CAGAGCCAGC TGGCCCCTGC CGCAAGCCCT
1751 GTCCCTATGA ACAGGCTCTG GGTGGCGATG GGCCTGAGGA GCAGTGA
```

Unc93b (3d mutant)Amino Acid Sequence    (SEQ ID NO:2)

```
   1 MEVEPPLYPV AGAAGPQGDE DRHGVPDGPE APLDELVGAY PNYNEEEEER
  51 RYYRRKRLGV VKNVLAASTG VTLTYGVYLG LLQMQLILHY DETYREVKYG
 101 NMGLPDIDSK MLMGINVTPI AALLYTPVLI RFFGTKWMMF LAVGIYALFV
 151 STNYWERYYT LVPSAVALGM AIVPLWASMG NYITRMSQKY YEYSHYKEQD
 201 EQGPQQRPPR GSHAPYLLVF QAIFYSFFHL SFACAQLPMI YFLNNYLYDL
 251 NHTLINVQSC GTKSQGILNG FNKTVLRTLP RSKNLIVVES VLMAVAFLAM
 301 LMVLGLCGAA YRPTEEIDLR SVGWGNIFQL PFKHVRDFRL RHLVPFFIYS
 351 GFEVLFACTG FALGYGVCSM GLERLAYLLI AYSLGASASS VLGLLGLWLP
 401 RSVPLVAGAG LRLLLTLSLF FWAPAPRVLQ HSWIFYFVAA LWGVGSALNK
 451 TGLSTLLGIL YEDKERQDFI FTIYHWWQAV AIFVVYLGSS LPMKAKLAVL
 501 LVTLVAAAAS YLWMEQKLQQ GLVPRQPRIP KPQHKVRGYR YLEEDNSDES
 551 DMEGEQGQGD CAEDEAPQAG PLGAEPAGPC RKPCPYEQAL GGDGPEEQ
```

Figure 9

```
Unc93b cDNA (wild type)    (SEQ ID NO:3)
   1  ATGGAGGTGG AGCCTCCGCT CTACCCTGTG GCCGGGGCCG CGGGTCCTCA
  51  AGGGGATGAA GACCGGCACG GAGTTCCTGA TGGGCCAGAG GCTCCCTTGG
 101  ACGAACTCGT GGGTGCGTAC CCCAACTACA ATGAGGAGGA GGAAGAGCGC
 151  CGCTACTACC GCCGCAAGCG CCTCGGAGTG GTCAAGAACG TGCTGGCGGC
 201  CAGCACGGGT GTCACCCTTA CTTACGGCGT CTACCTGGGC CTCCTGCAGA
 251  TGCAACTGAT CCTGCACTAT GATGAGACCT ACAGAGAGGT GAAGTATGGC
 301  AACATGGGGC TGCCGGACAT CGATAGCAAG ATGCTGATGG GTATCAACGT
 351  GACGCCTATC GCTGCCCTGC TCTACACACC TGTGCTCATC AGGTTTTTTG
 401  GTACCAAGTG GATGATGTTC TTGGCTGTGG GCATCTATGC CCTCTTTGTC
 451  TCTACCAACT ACTGGGAACG CTACTACACG CTGGTGCCCT CTGCTGTGGC
 501  TCTGGGCATG GCCATTGTGC CTCTGTGGGC CTCCATGGGC AACTATATCA
 551  CCAGGATGTC CCAGAAGTAC TATGAATACT CCCACTACAA GGAGCAAGAT
 601  GAGCAGGGAC CTCAGCAGCG CCCACCACGA GGTTCCCACG CACCCTATCT
 651  CCTGGTTTTC CAGGCCATCT TCTATAGCTT CTTCCACTTG AGCTTCGCGT
 701  GTGCCCAGCT GCCCATGATT TACTTCCTCA ACAACTACCT GTATGACCTG
 751  AACCACACAC TGATCAACGT GCAGAGCTGC GGTACTAAGA GCCAAGGCAT
 801  TCTGAATGGC TTCAACAAGA CGGTCCTTCG GACGCTGCCG CGCAGCAAAA
 851  ACCTTATTGT TGTAGAGAGC GTGCTCATGG CGGTGGCCTT CTTGGCCATG
 901  CTGATGGTGC TGGGCCTGTG TGGAGCCGCT TACCGGCCCA CGGAAGAGAT
 951  CGACCTGCGC AGCGTGGGCT GGGGCAACAT CTTCCAGCTG CCCTTCAAAC
1001  ACGTGCGTGA CTTTCGCTTA CGCCATCTGG TGCCCTTCTT TATCTACAGT
1051  GGCTTTGAGG TGCTCTTTGC CTGCACTGGT TTTGCCCTGG GCTACGGCGT
1101  GTGCTCCATG GGGCTGGAGC GACTGGCATA CCTGCTCATA GCTTACAGCC
1151  TGGGTGCCTC AGCCTCCTCG GTTCTGGGGC TGCTGGGACT GTGGCTGCCT
1201  CGCTCTGTCC CGCTCGTGGC TGGGGCAGGA CTGCGCCTAC TGCTCACCCT
1251  TAGCCTCTTT TTCTGGGCTC CTGCTCCTCG GGTCCTCCAG CACAGTTGGA
1301  TCTTTTACTT CGTGGCTGCC CTCTGGGGTG TGGGCAGCGC CCTCAACAAG
1351  ACCGGACTTA GCACACTCCT GGGCATCCTA TATGAAGACA AAGAGAGGCA
1401  GGACTTCATC TTCACCATCT ATCACTGGTG GCAGGCCGTG GCCATCTTTG
1451  TTGTGTACCT GGGCTCCAGC TTGCCCATGA AGGCCAAGCT GGCAGTGTTG
1501  CTGGTGACCC TGGTAGCAGC AGCAGCCTCA TACCTGTGGA TGGAGCAGAA
1551  GTTGCAGCAA GGATTGGTCC CGCGGCAGCC GCGCATTCCG AAGCCACAGC
1601  ACAAAGTCCG CGGCTACCGC TACCTGGAGG AGGACAACTC GGATGAGAGT
1651  GACATGGAGG GCGAGCAGGG TCAGGGGGAC TGCGCAGAGG ACGAAGCACC
1701  ACAGGCAGGG CCCCTGGGTG CAGAGCCAGC TGGCCCCTGC CGCAAGCCCT
1751  GTCCCTATGA ACAGGCTCTG GGTGGCGATG GGCCTGAGGA GCAGTGA Unc93b Amino Acid Sequence (wild type)  (SEQ ID NO:4)
   1  MEVEPPLYPV AGAAGPQGDE DRHGVPDGPE APLDELVGAY PNYNEEEEER
  51  RYYRRKRLGV VKNVLAASTG VTLTYGVYLG LLQMQLILHY DETYREVKYG
 101  NMGLPDIDSK MLMGINVTPI AALLYTPVLI RFFGTKWMMF LAVGIYALFV
 151  STNYWERYYT LVPSAVALGM AIVPLWASMG NYITRMSQKY YEYSHYKEQD
 201  EQGPQQRPPR GSHAPYLLVF QAIFYSFFHL SFACAQLPMI YFLNNYLYDL
 251  NHTLINVQSC GTKSQGILNG FNKTVLRTLP RSKNLIVVES VLMAVAFLAM
 301  LMVLGLCGAA YRPTEEIDLR SVGWGNIFQL PFKHVRDFRL RHLVPFFIYS
 351  GFEVLFACTG FALGYVCSM GLERLAYLLI AYSLGASASS VLGLLGLWLP
 401  RSVPLVAGAG LHLLLTLSLF FWAPAPRVLQ HSWIFYFVAA LWGVGSALNK
 451  TGLSTLLGIL YEDKERQDFI FTIYHWWQAV AIFVVYLGSS LPMKAKLAVL
 501  LVTLVAAAS YLWMEQKLQQ GLVPRQPRIP KPQHKVRGYR YLEEDNSDES
 551  DMEGEQGQGD CAEDEAPQAG PLGAEPAGPC RKPCPYEQAL GGDGPEEQ
```

COMPOSITIONS AND METHODS FOR TREATMENT OF AUTOIMMUNE AND RELATED DISEASES

STATEMENT OF GOVERNMENT SUPPORT

This invention was made by government support by Grant Nos. U54-AI54523, AI 40682 and GM 60031 from National Institutes of Health. The Government has certain rights in this invention.

CROSS-REFERENCE TO RELATED APPLICATIONS

This application is the National Stage of International Application No. PCT/US2006/007420, filed Mar. 2, 2006, which claims the benefit of U.S. Provisional Patent Application No. 60/658,197, filed Mar. 2, 2005, the entire disclosures of which are incorporated herein by reference.

FIELD

The present invention relates generally to molecular immunology and the treatment of human diseases. In particular, the invention provides 3d, a point mutation of the protein uncoordinated-93b (referred to as unc-93B; also known as unc-93b1), unc-93A, unc-93B, and unc-93C polypeptides, nucleic acids encoding them and methods for making and using them, for example, to produce transgenic non-human animals. In one aspect, the polypeptides of the invention have altered Toll-like receptor 3, Toll-like receptor 7-, Toll-like receptor 9-signaling activity. Methods for treating disease in a mammalian subject are provided by administering modulators, e.g., inhibitors, of Toll-like receptor 3, Toll-like receptor 7-, Toll-like receptor 9-signaling activity.

BACKGROUND

The mammalian Toll-like receptors (TLR) sense conserved molecules of microbial origin, including bacterial lipopolysaccharides (LPS), lipopeptides, glucans, flagellin, and nucleic acids. Poltorak, A. et al., *Science* 282:2085-2088, 1998; Takeuchi, O. et al., *J. Immunol.* 164:554-557, 2000; Takeuchi, O. et al., 13:933-940, 2001; Gantner, B. N. et al., *J. Exp. Med.* 197:1107-1117, 2003; Hayashi, F. et al., *Nature* 410:1099-1103, 2001; Hemmi, H. et al., *Nature* 408:740-745, 2000; Alexopoulou, L. et al., *Nature* 413:732-738, 2001; Diebold, S. S. et al., *Science* 303:1529-1531, 2004; Heil, F. et al., *Science* 303:1526-1529, 2004; Lund, J. M. et al., *Proc. Natl. Acad. Sci U.S.A* 101:5598-5603, 2004. While TLRs 1, 2, 4, and 6 are at least partly represented on the surface of mammalian cells, TLRs 3, 7, and 9, which detect dsRNA, ssRNA, and unmethylated DNA, respectively are predominantly or entirely intracellular receptors, residing within the endoplasmic reticulum (ER) and/or endosomes. Hemmi, H. et al., *Nature* 408:740-745, 2000; Alexopoulou, L. et al., *Nature* 413:732-738, 2001; Diebold, S. S. et al., *Science* 303:1529-1531, 2004; Heil, F. et al., *Science* 303:1526-1529, 2004; Lund, J. M. et al., *Proc. Natl. Acad. Sci U.S.A* 101: 5598-5603, 2004; Matsumoto, M. et al., *J. Immunol.* 171: 3154-3162, 2003; Funami, K. et al., *Int. Immunol.* 16:1143-1154, 2004; Ahmad-Nejad, P. et al., *Eur. J. Immunol.* 32:1958-1968, 2002; Leifer, C. A. et al., 173:1179-1183, 2004; Latz, E. et al., 5:190-198, 2004; Heil, F. et al., *Eur. J. Immunol.* 33:2987-2997, 2003.

TLRs mediate the great majority of phenomena associated with microbial infections, including the upregulation of costimulatory molecules that are required to initiate adaptive immune responses to peptides processed and presented by antigen-presenting cells of the host. Beutler, B. *Nature* 430: 257-263, 2004. But the processing and presentation of antigens—whether endogenous or exogenous—occurs constitutively in the absence of infection and does not dependent upon TLR signaling. Moreover, where exogenous antigens are concerned, processing for class I MHC presentation (cross presentation) involves a series of biochemical events very different from those associated with processing for class II MHC presentation.

SUMMARY

Compositions and methods are provided for treatment of disease which comprise administering to the mammalian subject a compound capable of modulating Toll-like receptor 3-signaling, Toll-like receptor 7-signaling, or Toll-like receptor 9-signaling activity via unc-93A, unc-93B, or unc-93C, wherein the compound is administered in an amount effective to reduce or eliminate the autoimmune disease or to prevent its occurrence or recurrence. Compositions and methods of the present invention provide a single nucleotide substitution, e.g., 3d allele in unc-93B, or alleles of unc-93A, unc-93B, or unc-93C, that abrogate signaling via Toll-like receptors (TLRs) 3, 7, and 9 (but not other TLRs) and markedly impair both class I and class II MHC presentation of exogenous antigens. This mutation reveals a point of intersection between the cellular events required for exogenous antigen presentation and those required for activation of the intracellular TLRs.

A method for treating an autoimmune disease in a mammalian subject, is provided comprising administering to the mammalian subject a compound capable of modulating Toll-like receptor 3-signaling, Toll-like receptor 7-signaling, or Toll-like receptor 9-signaling activity via unc-93A, unc-93B, or unc-93C, wherein the compound is administered in an amount effective to reduce or eliminate the autoimmune disease or to prevent its occurrence or recurrence.

A method for treating an infectious disease in a mammalian subject is provided comprising administering to the mammalian subject a compound capable of modulating Toll-like receptor 3-signaling, Toll-like receptor 7-signaling, or Toll-like receptor 9-signaling activity via unc-93A, unc-93B, or unc-93C, wherein the compound is administered in an amount effective to reduce or eliminate the infectious disease or to prevent its occurrence or recurrence.

A method for treating an inflammatory disease in a mammalian subject is provided comprising administering to the mammalian subject a compound capable of modulating Toll-like receptor 3-signaling, Toll-like receptor 7-signaling, or Toll-like receptor 9-signaling activity via unc-93A, unc-93B, or unc-93C, wherein the compound is administered in an amount effective to reduce or eliminate the autoimmune disease or to prevent its occurrence or recurrence.

A method for treating an CD8 cell defect, a CD4 cell defect, or an antigen presenting cell defect in a mammalian subject is provided comprising administering to the mammalian subject a compound capable of modulating Toll-like receptor 3-signaling, Toll-like receptor 7-signaling, or Toll-like receptor 9-signaling activity via unc-93A, unc-93B, or unc-93C, wherein the compound is administered in an amount effective to reduce or eliminate the autoimmune disease or to prevent its occurrence or recurrence. The therapeutic compound is an antagonist of Toll-like receptor 3-signaling, Toll-like receptor 7-signaling, or Toll-like receptor 9-signaling activity via unc-93A, unc-93B, or unc-93C. In one aspect, the compound is an inhibitor of unc-93A, unc-93B, or unc-93C. In a further aspect, the compound is interfering RNA, short hairpin RNA, ribozyme, antisense oligonucleotide, small chemical compound, or protein inhibitor. In another aspect, the compound is an inhibitor of proteins targeted to endosomes by unc-93A, unc-93B, or unc-93C. In a detailed aspect, the compound is a protease inhibitor. In a further aspect, unc-93B is an unc-93B polypeptide having (i) an amino acid sequence having at least 95% sequence identity to SEQ ID NO:4; or (ii) an amino acid sequence encoded by a nucleic acid comprising a sequence having at least 90% sequence identity to SEQ ID NO:3; wherein the polypeptide has an Toll-like receptor 3-, Toll-like receptor 7-, or Toll-like receptor 9-signaling activity.

Treatment of the autoimmune disease includes, but is not limited to, treatment for insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis $Hb_s$-ve, cryptogenic cirrhosis, ulcerative colitis, Sjogren's syndrome, scleroderma, Wegener's granulomatosis, poly/dermatomyositis, discoid LE or systemic lupus erythematosus.

A transgenic non-human animal is provided comprising a heterologous nucleic acid encoding unc-93A, unc-93B, or unc-93C, or a variant thereof, wherein said animal exhibits a phenotype, relative to a wild-type phenotype comprising a characteristic of inhibition of macrophage activation, susceptibility to viral or bacterial infection, a decrease in TNF-α production, or a combination of any two or more thereof. The nucleic acid encoding unc-93B further comprises a sequence having at least 90% sequence identity to SEQ ID NO:1. The transgenic animal includes, but is not limited to, a mouse or a rat.

An in vivo method for screening for a modulator of an autoimmune disease, an infectious disease, an inflammatory disease, an antigen presenting cell defect, a CD8 cell defect, or a CD4 cell defect is provided comprising: contacting the transgenic non-human animal with a test compound; and detecting an increase or a decrease in the amount or severity of the autoimmune disease, the infectious disease, the inflammatory disease, the antigen presenting cell defect, the CD8 cell defect, or the CD4 cell defect; wherein the increase or the decrease identifies the test compound as a modulator of the autoimmune disease, the infectious disease, an inflammatory disease, the antigen presenting cell defect, the CD8 cell defect, or the CD4 cell defect.

An in vivo method to identify a genetic modulator of an autoimmune disease, an infectious disease, an inflammatory disease, an antigen presenting cell defect, a CD8 cell defect, or a CD4 cell defect is provided comprising: inserting a test gene into one or more cells of the transgenic non-human animal; and detecting an increase or a decrease in the amount or severity of the autoimmune disease, the infectious disease, the inflammatory disease, the antigen presenting cell defect, the CD8 cell defect, or the CD4 cell defect; wherein the increase or decrease identifies the test gene as a genetic modulator of the autoimmune disease, the infectious disease, the antigen presenting cell defect, the CD8 cell defect, or the CD4 cell defect.

An in vivo method to identify a genetic modulator of an autoimmune disease, an infectious disease, an inflammatory disease, an antigen presenting cell defect, a CD8 cell defect, or a CD4 cell defect is provided comprising: mating the first transgenic non-human animal with a second non-human animal of a sex opposite of the first transgenic non-human animal, wherein the second non-human animal is selected from the group consisting of an inbred non-human animal strain, a randomly mutagenized non-human animal, a transgenic non-human animal, and a knockout non-human animal; and selecting an offspring of the mating that exhibits an increase or a decrease in the amount or severity of the autoimmune disease, the infectious disease, the inflammatory disease, the antigen presenting cell defect, the CD8 cell defect, or the CD4 cell defect, thereby identifying a genetic modulator of the autoimmune disease, the infectious disease, the inflammatory disease, the antigen presenting cell defect, the CD8 cell defect, or the CD4 cell defect.

An in vivo method to identify a genetic modulator of an autoimmune disease, an infectious disease, an inflammatory disease, an antigen presenting cell defect, a CD8 cell defect, or a CD4 cell defect, said method comprising: (i) mating the first transgenic non-human animal with a second non-human animal of a sex opposite of the first transgenic non-human animal, wherein the second non-human animal is a randomly mutagenized non-human animal; (ii) mating two offspring of the mating of step (i); and (iii) identifying offspring of the mating of step (ii) that carry two mutated alleles of unc-93A, unc-93B, or unc-93C, and that exhibit an increase or a decrease in the amount or severity of the autoimmune disease, the infectious disease, the inflammatory disease, the antigen presenting cell defect, the CD8 cell defect, or the CD4 cell defect, thereby identifying a genetic modulator of the autoimmune disease, the infectious disease, the inflammatory disease, the antigen presenting cell defect, the CD8 cell defect, or the CD4 cell defect. In a further aspect, the unc-93B allele is a nucleic acid having at least 90% identity with SEQ ID NO:1.

An in vivo method to identify a genetic modulator of an autoimmune disease, an infectious disease, an inflammatory disease, an antigen presenting cell defect, a CD8 cell defect, or a CD4 cell defect is provided comprising: (i) mating the first transgenic non-human animal with a second non-human animal of a sex opposite of the first transgenic non-human animal, wherein the second non-human animal is a randomly mutagenized non-human animal; (ii) mating an offspring of the mating of step (i) with the first transgenic non-human animal; and (iii) identifying offspring of the mating of step (ii) that carry two mutated alleles of unc-93A, unc-93B, or unc-93C and that exhibit an increase or a decrease in the amount or severity of the autoimmune disease, the infectious disease, the inflammatory disease, the antigen presenting cell defect, the CD8 cell defect, or the CD4 cell defect, thereby identifying a genetic modulator of the autoimmune disease, the infectious disease, the inflammatory disease, the antigen presenting cell defect, the CD8 cell defect, or the CD4 cell defect. In a further aspect, the unc-93B allele is a nucleic acid having at least 90% identity with SEQ ID NO:1.

An in vivo method to identify a genetic modulator of an autoimmune disease, an infectious disease, an inflammatory disease, an antigen presenting cell defect, a CD8 cell defect, or a CD4 cell defect is provided comprising: (i) mating the first transgenic non-human animal with a second non-human animal of a sex opposite of the first transgenic non-human animal, wherein the second non-human animal is a randomly mutagenized non-human animal; (ii) mating an offspring of the mating of step (i) with a randomly mutagenized non-human animal; and (iii) identifying offspring of the mating of step (ii) that carry two mutated alleles of unc-93A, unc-93B, or unc-93C and that exhibit an increase or a decrease in the amount or severity of the autoimmune disease, the infectious disease, the inflammatory disease, the antigen presenting cell defect, the CD8 cell defect, or the CD4 cell defect, thereby identifying a genetic modulator of the autoimmune disease, the infectious disease, the inflammatory disease, the antigen presenting cell defect, the CD8 cell defect, or the CD4 cell defect. In a further aspect, the unc-93B allele is a nucleic acid having at least 90% identity with SEQ ID NO:1.

In one aspect, a cell or cell line derived from a transgenic non-human animal. An in vitro method of screening for a modulator of a Toll-like receptor 3, Toll-like receptor 7-, or Toll-like receptor 9-signaling activity is provided comprising: contacting the cell or cell line with a test compound; and detecting an increase or a decrease in the amount of TNF-α production, susceptibility to viral or bacterial infection, or an Toll-like receptor 3-, Toll-like receptor 7-, or Toll-like receptor 9-induced macrophage activating activity; thereby identifying the test compound as a modulator of a Toll-like receptor 3-, Toll-like receptor 7-, or Toll-like receptor 9-induced macrophage activating activity.

A knockout non-human animal is provided wherein an endogenous gene sequence comprising a nucleic acid sequence encoding unc-93A, unc-93B, or unc-93C is disrupted so as to produce a phenotype comprising a characteristic of inhibition of macrophage activation, susceptibility to viral or bacterial infection, a decrease in TNF-α production, or a combination of any two or more thereof. In a further aspect, the nucleic acid sequence encoding unc-93B has at least 90% sequence identity to SEQ ID NO:3. The knockout non-human animal includes, but is not limited to, a mouse or a rat. In one aspect, a cell or cell line is derived from a knockout non-human animal.

An in vivo method for screening for a modulator of an autoimmune disease, an infectious disease, an inflammatory disease, an antigen presenting cell defect, a CD8 cell defect, or a CD4 cell defect is provided comprising: contacting the knockout non-human animal with a test compound; and detecting an increase or a decrease in the amount or severity of the autoimmune disease, the infectious disease, the inflammatory disease, the antigen presenting cell defect, the CD8 cell defect, or the CD4 cell defect; wherein the increase or the decrease identifies the test compound as a modulator of the autoimmune disease, the infectious disease, the inflammatory disease, the antigen presenting cell defect, the CD8 cell defect, or the CD4 cell defect.

An in vivo method to identify a genetic modulator of an autoimmune disease, an infectious disease, an inflammatory disease, an antigen presenting cell defect, a CD8 cell defect, or a CD4 cell defect is provided comprising: inserting a test gene into one or more cells of the knockout non-human animal; and detecting an increase or a decrease in the amount or severity of the autoimmune disease, the infectious disease, the inflammatory disease, the antigen presenting cell defect, the CD8 cell defect, or the CD4 cell defect; wherein the increase or decrease identifies the test gene as a genetic modulator of the autoimmune disease, the infectious disease, the inflammatory disease, the antigen presenting cell defect, the CD8 cell defect, or the CD4 cell defect.

An inbred mouse is provided comprising a genome that is homozygous for a nucleic acid sequence encoding a polypeptide having at least 95% sequence identity to SEQ ID NO:4, wherein said polypeptide comprises a change in the amino acid sequence of SEQ ID NO:4 at amino acid residue number 411. In a further aspect, the polypeptide comprises a sequence as set forth in SEQ ID NO:2. In a further aspect, the inbred mouse has a phenotype comprising a characteristic of an autoimmune disease, an infectious disease, an inflammatory disease, an antigen presenting cell defect, a CD8 cell defect, or a CD4 cell defect.

An in vivo method for screening for a modulator of an autoimmune disease, an infectious disease, an inflammatory disease, an antigen presenting cell defect, a CD8 cell defect, or a CD4 cell defect is provided comprising: contacting the inbred mouse with a test compound; and detecting an increase or a decrease in the amount or severity of the autoimmune disease, the infectious disease, the antigen presenting cell defect, the CD8 cell defect, or the CD4 cell defect; wherein the increase or the decrease identifies the test compound as a modulator of the autoimmune disease, the infectious disease, the inflammatory disease, the antigen presenting cell defect, the CD8 cell defect, or the CD4 cell defect.

An in vivo method to identify a genetic modulator of an autoimmune disease, an infectious disease, an inflammatory disease, an antigen presenting cell defect, a CD8 cell defect, or a CD4 cell defect is provided comprising: inserting a test gene into one or more cells of the inbred mouse; and detecting an increase or a decrease in the amount or severity of the autoimmune disease, the infectious disease, the inflammatory disease, the antigen presenting cell defect, the CD8 cell defect, or the CD4 cell defect; wherein the increase or decrease identifies the test gene as a genetic modulator of the autoimmune disease, the infectious disease, the inflammatory disease, the antigen presenting cell defect, the CD8 cell defect, or the CD4 cell defect.

An in vivo method to identify a genetic modulator of an autoimmune disease, an infectious disease, an inflammatory disease, an antigen presenting cell defect, a CD8 cell defect, or a CD4 cell defect is provided comprising: mating the first inbred mouse with a second mouse of a sex opposite of the first inbred mouse, wherein the second mouse is selected from the group consisting of an inbred mouse strain, a randomly mutagenized mouse, a transgenic mouse, and a knockout mouse; and selecting an offspring of the mating that exhibits an increase or a decrease in the amount or severity of the autoimmune disease, the infectious disease, the inflammatory disease, the antigen presenting cell defect, the CD8 cell defect, or the CD4 cell defect, thereby identifying a genetic modulator of the autoimmune disease, the infectious disease, the inflammatory disease, the antigen presenting cell defect, the CD8 cell defect, or the CD4 cell defect.

An in vivo method to identify a genetic modulator of an autoimmune disease, an infectious disease, an inflammatory disease, an antigen presenting cell defect, a CD8 cell defect, or a CD4 cell defect is provided comprising: (i) mating the first inbred mouse with a second mouse of a sex opposite of the first inbred mouse, wherein the second mouse is a randomly mutagenized non-human animal; (ii) mating two offspring of the mating of step (i); and (iii) identifying offspring of the mating of step (ii) that carry two mutated alleles of a nucleic acid encoding unc-93A, unc-93B, or unc-93C, and that exhibit an increase or a decrease in the amount or severity of the autoimmune disease, the infectious disease, the inflammatory disease, the antigen presenting cell defect, the CD8 cell defect, or the CD4 cell defect, thereby identifying a genetic modulator of the autoimmune disease, the infectious disease, the inflammatory disease, the antigen presenting cell defect, the CD8 cell defect, or the CD4 cell defect. In a further aspect, the nucleic acid encoding unc-93B has at least 90% identity with SEQ ID NO:1.

An in vivo method to identify a genetic modulator of an autoimmune disease, an infectious disease, an inflammatory disease, an antigen presenting cell defect, a CD8 cell defect, or a CD4 cell defect, said method comprising: (i) mating the first inbred mouse with a second mouse of a sex opposite of the first inbred mouse, wherein the second mouse is a randomly mutagenized non-human animal; (ii) mating an offspring of the mating of step (i) with the first inbred mouse; and (iii) identifying offspring of the mating of step (ii) that carry two mutated alleles of a nucleic acid encoding unc-93A, unc-93B, or unc-93C and that exhibit an increase or a decrease in the amount or severity of the autoimmune disease, the infectious disease, the inflammatory disease, the antigen presenting cell defect, the CD8 cell defect, or the CD4 cell defect, thereby identifying a genetic modulator of the autoimmune disease, the infectious disease, the inflammatory disease, the antigen presenting cell defect, the CD8 cell defect, or the CD4 cell defect. In a further aspect, the nucleic acid encoding unc-93B has at least 90% identity with SEQ ID NO:1.

An in vivo method to identify a genetic modulator of an autoimmune disease, an infectious disease, an inflammatory disease, an antigen presenting cell defect, a CD8 cell defect, or a CD4 cell defect is provided comprising: (i) mating the first inbred mouse with a second mouse of a sex opposite of the first inbred mouse, wherein the second mouse is a randomly mutagenized mouse; (ii) mating an offspring of the mating of step (i) with a randomly mutagenized mouse; and (iii) identifying offspring of the mating of step (ii) that carry a mutated allele of a nucleic acid encoding unc-93A, unc-93B, or unc-93C and that exhibit an increase or a decrease in the amount or severity of the autoimmune disease, the infectious disease, the inflammatory disease, the antigen presenting cell defect, the CD8 cell defect, or the CD4 cell defect, thereby identifying a genetic modulator of the autoimmune disease, the infectious disease, the inflammatory disease, the antigen presenting cell defect, the CD8 cell defect, or the CD4 cell defect. In a further aspect, the nucleic acid encoding unc-93B has at least 90% identity with SEQ ID NO:1.

In a further aspect, a cell or cell line derived from the inbred mouse. An in vitro method of screening for a modulator of a Toll-like receptor 3-, Toll-like receptor 7-, or Toll-like receptor 9-signaling activity is provided comprising: contacting the cell or cell line with a test compound; and detecting an increase or a decrease in the amount of TNF-α production, susceptibility to viral or bacterial infection, or an Toll-like receptor 3-, Toll-like receptor 7-, or Toll-like receptor 9-induced macrophage activating activity; thereby identifying the test compound as a modulator of a Toll-like receptor 3-, Toll-like receptor 7-, or Toll-like receptor 9-induced macrophage activating activity. An in vivo method of screening for a modulator of a Toll-like receptor 3-, Toll-like receptor 7-, or Toll-like receptor 9-signaling activity is provided comprising: contacting the cell or cell line with a test compound; and detecting an increase or a decrease in the amount of TNF-α production, susceptibility to viral or bacterial infection, or an Toll-like receptor 3-, Toll-like receptor 7-, or Toll-like receptor 9-induced macrophage activating activity; thereby identifying the test compound as a modulator of a Toll-like receptor 3-, Toll-like receptor 7-, or Toll-like receptor 9-induced macrophage activating activity.

A method for generating a toleragenic signal in a subject is provided comprising administering to the subject an amount of an antisense oligonucleotide complementary unc-93A, unc-93B, or unc-93C sufficient to inhibit the expression of a unc-93A polypeptide, unc-93B polypeptide, or unc-93C polypeptide, thereby generating an antigen presenting cell defect, a CD8 cell defect, or a CD4 cell defect and generating a toleragenic signal in the subject. In a further aspect, the antisense oligonucleotide to unc-93B is complementary to SEQ ID NO:3.

A method for generating a tolerogenic signal in a subject is provided comprising administering to the subject an amount of an antibody to an unc-93A polypeptide, unc-93B polypeptide, or unc-93C polypeptide sufficient to inhibit the activity of the unc-93A polypeptide, unc-93B polypeptide, or unc-93C polypeptide, thereby generating an antigen presenting cell defect, a CD8 cell defect, or a CD4 cell defect in the subject. In a further aspect, the antibody to the unc-93B polypeptide is an antibody to a polypeptide of SEQ ID NO:4.

A method for tolerizing a subject to an antigen, said method comprising: administering to the subject an amount of an antisense oligonucleotide complementary to a nucleic acid encoding unc-93A, unc-93B, or unc-93C sufficient to inhibit the expression of an unc-93A polypeptide, unc-93B polypeptide, or unc-93C polypeptide, thereby generating an antigen presenting cell defect, a CD8 cell defect, or a CD4 cell defect and generating a toleragenic signal in the subject; and administering an antigen to the subject, thereby tolerizing the subject to the antigen. In a further aspect, the antisense oligonucleotide to unc-93B is an antisense oligonucleotide complementary to SEQ ID NO:3.

A method for tolerizing a subject to an antigen is provided comprising: administering to the subject an amount of an antibody to an unc-93A polypeptide, unc-93B polypeptide, or unc-93C polypeptide sufficient to inhibit the expression of the unc-93A polypeptide, unc-93B polypeptide, or unc-93C polypeptide, thereby generating a an antigen presenting cell defect, a CD8 cell defect, or a CD4 cell defect and generating a toleragenic signal in the subject; and administering an antigen to the subject, thereby tolerizing the subject to the antigen. In a further aspect, the antibody to the unc-93B polypeptide is an antibody to a polypeptide of SEQ ID NO:4.

A method for tolerizing a subject to an antigen, said method comprising: administering to the subject an amount of small chemical inhibitor to a unc-93A polypeptide, unc-93B polypeptide, or unc-93C polypeptide having a Toll-like receptor 3-, Toll-like receptor 7-, or Toll-like receptor 9-signaling activity, the small chemical inhibitor sufficient to inhibit the expression of the unc-93A polypeptide, unc-93B polypeptide, or unc-93C polypeptide, thereby generating an antigen presenting cell defect, a CD8 cell defect, or a CD4 cell defect and generating a toleragenic signal in the subject; and administering the antigen to the subject, thereby tolerizing the subject to the antigen.

A non-human transgenic animal is provided having a knockout mutation in one or both alleles encoding a polypeptide substantially identical to an unc-93A polypeptide, unc-93B polypeptide, or unc-93C polypeptide.

A transgenic knockout mouse is provided whose genome comprises a homozygous disruption in its endogenous unc-93A gene, unc-93B gene, or unc-93C gene, wherein said homozygous disruption prevents the expression of a functional unc-93A protein, unc-93B protein, or unc-93C protein, resulting in a transgenic knockout mouse in which Toll-like receptor 3-, Toll-like receptor 7- or Toll-like receptor 9-induced costimulatory molecule expression in macrophages is inhibited, as compared to which Toll-like receptor 3-, Toll-like receptor 7- or Toll-like receptor 9-induced costimulatory molecule expression in macrophages of a wild type mouse. In one aspect, the homozygous disruption in the gene of the transgenic knockout mouse results from deletion or mutation of portions of the endogenous unc-93A gene, unc-93B gene, or unc-93C gene whereby a non-functional gene product or complete absence of the gene product is produced.

A transgenic knockout mouse is provided whose genome comprises a homozygous disruption in its endogenous unc-93A gene, unc-93B gene, or unc-93C gene, wherein said homozygous disruption prevents the expression of a functional unc-93A protein, unc-93B protein, or unc-93C protein, resulting in a transgenic knockout mouse which has an increased susceptibility to bacterial or viral infection as compared to a susceptibility to bacterial or viral infection in a wild type mouse. In one aspect, the homozygous disruption in the gene of the transgenic knockout mouse results from the homozygous disruption results from deletion or mutation of portions of the endogenous unc-93A gene, unc-93B gene, or unc-93C gene whereby a non-functional gene product or complete absence of the gene product is produced. In a further aspect, the increased susceptibility to bacterial or viral infection is increased susceptibility to mouse cytomegalovirus infection or increased susceptibility to *Staphylococcus aureus* infection.

A transgenic knockout mouse whose genome comprises a homozygous disruption in its endogenous unc-93A gene, unc-93B gene, or unc-93C gene, wherein said homozygous disruption prevents the expression of a functional unc-93A protein, unc-93B protein, or unc-93C protein, resulting in a transgenic knockout mouse which has a decreased production of TNF-α induced by CpG-oligodeoxynucleotide, Resiquimod, or poly I:C as compared to production of TNF-α induced by CpG-oligodeoxynucleotide, Resiquimod, or poly I:C in a wild type mouse. The homozygous disruption in the transgenic knockout mouse results from deletion or mutation of portions of the endogenous unc-93A gene, unc-93B gene, or unc-93C gene whereby a non-functional gene product or complete absence of the gene product is produced. In a further aspect, the homozygous disruption consists of a histidine to arginine replacement at position 411 of the unc-93B polypeptide.

BRIEF DESCRIPTION OF THE DRAWINGS

FIGS. 2A, 2B, 2C, 2D, 2E, 2F, 2G, 2H show susceptibility to infection in 3d homozygotes.

FIG. 7 shows SNPs and a novel microsatellite marker used to confine the 3d critical region. (Ensemble distance)

FIG. 8 shows the cDNA and amino acid sequence of the 3d mutant of unc-93b.

FIG. 9 shows the cDNA and amino acid sequence of the wild type unc-93b.

DETAILED DESCRIPTION

1. Introduction

Figure 1A:
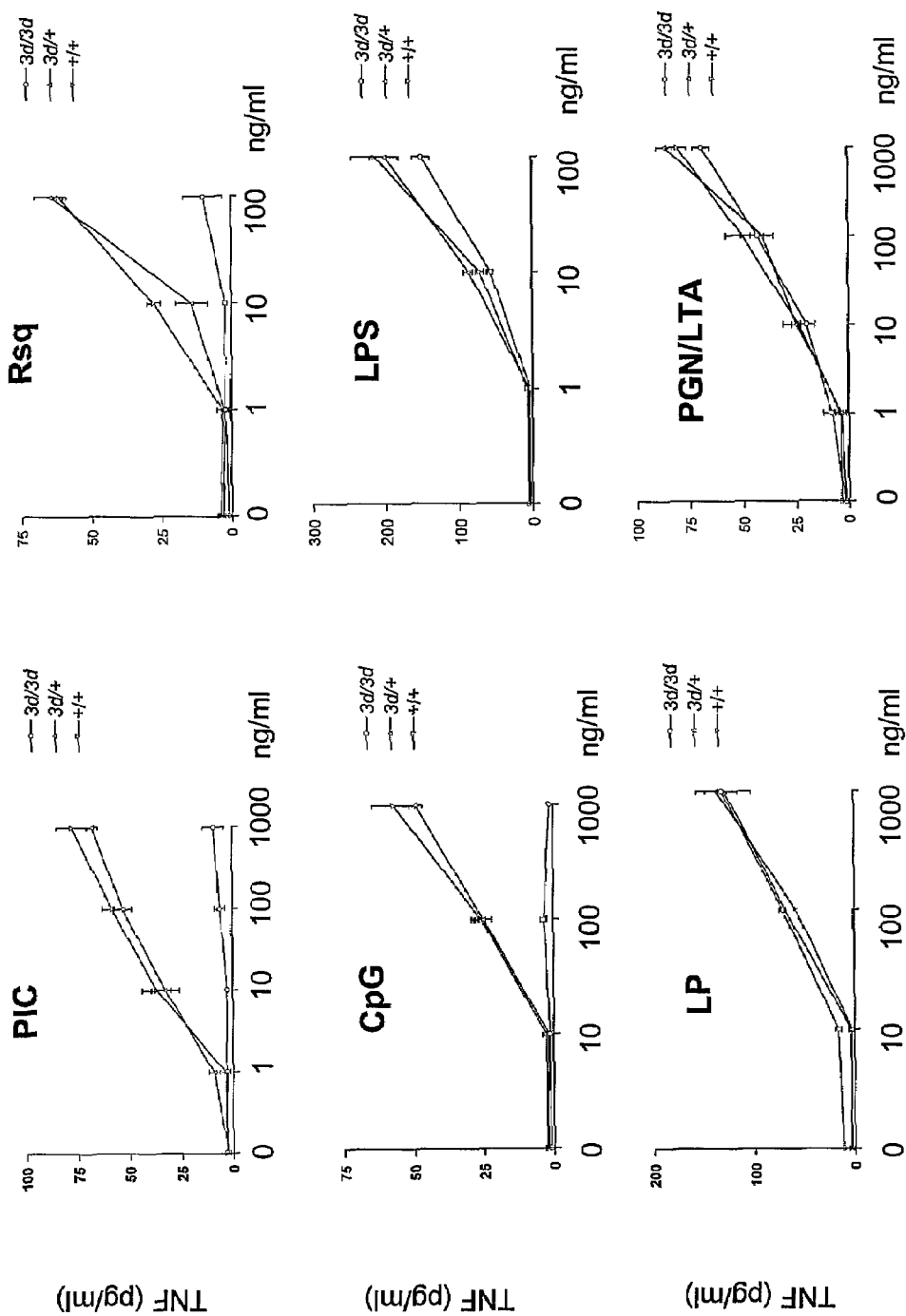
FIGS. 1A, 1B show TLR3, TLR7 and TLR9 signaling are prevented by the 3d mutation, which has no effect on endosome pH.

The invention provides 3d, a point mutation of the protein uncoordinated-93b (referred to as unc-93B), unc-93A, unc-93B, or unc-93C, polypeptides, nucleic acids encoding them and methods for making and using them, for example, to produce transgenic non-human animals.

In one aspect, the polypeptides of the invention have Toll-like receptor (TLR), e.g., TLR3-, TLR7-, or TLR9-signaling activity. The invention also provides non-human animals, e.g., transgenics or inbred strains, comprising the 3d polypeptides and/or nucleic acids of the invention, and methods for making and using these animals. The invention provides in vitro and in vivo methods to identify genetic or chemical modulators of a TLR3-, TLR7-, TLR9-signalling activity. The invention provides in vitro and in vivo methods to identify genetic or chemical modulators of autoimmune disease, conditions, or disorders. The invention also provides transgenic non-human animals and inbred strains comprising non-human animals having their endogenous unc-93a, unc-93b, or unc-93c activity disabled by using the nucleic acids of the invention, e.g., by use of antisense nucleic acids of the invention or by knockout of unc-93b-encoding loci using nucleic acids of the invention.

As used herein uncoordinated-93a, unc-93a, UNC93A, uncoordinated-93b, unc-93b, UNC93B1, uncoordinated-93c, unc-93c, UNC93C, unc-93 homolog A, B1 or C (*C. elegans*), unc-93 related protein, unc93 (*C. elegans*) homolog B and unc93 (*C. elegans*) homolog B1, UNC93, UNC93A, UNC93B, and UNC93C are used interchangeably. UNC93B1 has the Genbank accession number BC018388 and has been mapped to chromosome 19A (GeneID: 54445). This gene encodes a protein with similarity to the *C. elegans* unc93 protein. The Unc93 protein is involved in the regulation or coordination of muscle contraction in the worm. See also Strausberg, R. L. et al., *Proc. Natl. Acad. Sci. U.S.A.* 99: 16899-16903, 2002). In both humans and in mice, unc-93A (NCBI accession no. CAD19523) was found to be the nearest paralogue of unc-93B with a clearly divergent sequence along its entire length. Its function has not been determined. In mice, unc-93A is encoded by a gene on chromosome 17 (Unc93a; MGI:1933250). unc-93A was itself found to be homologous to a still more distant paralogue, unc-93C, also of unknown function (MGI:1917150), encoded by a gene on chromosome 11. Sureau, A. et al., *Nucleic Acids Res.* 25, 4513-4522, 1997. The existence of still other, more distant family members was not definitively excluded.

"Ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, unc-93a, unc-93b, and unc-93c are paralogs of each other.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Autoimmune disease" refers to a disease caused by an inability of the immune system to distinguish foreign molecules from self molecules, and a loss of immunological tolerance to self antigens, that results in destruction of the self molecules. Autoimmune diseases, include but are not limited to, insulin-dependent diabetes mellitus (IDDM), multiple sclerosis, experimental autoimmune encephalomyelitis (an animal model of multiple sclerosis), rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis $Hb_s$-ve, cryptogenic cirrhosis, ulcerative colitis, Sjogren's syndrome, scleroderma, Wegener's granulomatosis, Poly/Dermatomyositis, discoid LE and systemic Lupus erythematosus.

"Autoantigen" refers to a self-antigen, that is, a substance normally found within a mammal and normally recognized as self, but due to an auto-immune disease, is erroneously recognized as foreign by the mammal. That is, an autoantigen is not recognized as part of the mammal itself by the lymphocytes or antibodies of that mammal and is erroneously attacked by the immunoregulatory system of the mammal as though such autoantigen were a foreign substance. An autoantigen thus acts to downregulate the arm of the immune system that is responsible for causing a specific autoimmune disease. As used herein, "autoantigen" also refers to autoantigenic substances which induce conditions having the symptoms of an autoimmune disease when administered to mammals. An autoantigen according to the invention also includes an epitope or a combination of epitopes derived from an autoantigen that is recognized. As foreign by the mammal and that is a self-antigen in non-disease states.

Autoantigens that are useful according to the invention include but are not limited to those autoantigens associated with suppression of T-cell mediated autoimmune diseases.

An autoantigen refers to a molecule that provokes an immune response, or induces a state of immunological tolerance, including but not limited to single or double stranded DNA, an antibody or fragments thereof, including synthetic peptides of corresponding nucleic acid genetic information, gamma globulins or fragments thereof, including synthetic peptides or corresponding nucleic acid genetic information, a transplantation antigen or fragments thereof, including synthetic peptides or corresponding nucleic acid genetic information. An autoantigen according to the invention also includes an epitope or a combination of epitopes derived from that autoantigen.

"T-cell mediated autoimmune disease" refers to an autoimmune disease wherein the effects of the disease are induced by $T_H1$ mediated stimulation of lymphocyte inflammatory cytokine production. T-cell mediated autoimmune diseases include but are not limited to experimental autoimmune encephalomyelitis, multiple sclerosis, rheumatoid arthritis, myasthenia gravis, thyroiditis, experimental uveoretinitis and □adioi disease of the intestine. Autoantigens associated with suppression of $T_H1$ mediated autoimmune diseases include but are not limited to glutamate decarboxylase, insulin, myelin basic protein, type II collagen, nicotinic acetylcholine receptor, thyroglobulin, thyroid peroxidase, and the rhodopsin glycoproteins S-Antigen, IRBP-retinal protein and recoverin.

"Inhibition of macrophage activation" refers to inhibition of TLR3-, TLR7-, and TLR9-induced costimulatory molecule (CD40 and CD86) expression in macrophages in response to inducers CpG, Rsq, or PIC. CD40 and CD86 expression on macrophages can be analyzed by FACS.

"Susceptibility to viral or bacterial infection" refers to susceptibility to an infectious virus, e.g., mouse cytomegalovirus (MCMV), or an infectious bacteria, *Listeria monocytogenes*. Susceptibility to infection with MCMV was measured as the time to death in mice resulting from MCMV infection. Susceptibility to infection with *L. monocytogenes* was measured as production of TNF and IL-12 p40 mRNA in macrophages of mice infected with *L. monocytogenes*. Susceptibility to infection with *Staphylococcus aureus* was measured as the time to death in mice resulting from *S. aureus* infection.

"Decrease in TNF-α production" refers to macrophages from the mammalian subject that fail to produce normal quantities of TNF-α in response to poly-I:C (a TLR3-selective stimulus), resiquimod (a TLR7-selective stimulus), and unmethylated DNA oligonucleotides bearing CpG motifs (CpG-ODN; a TLR9-selective stimulus).

"Immune cell response" refers to the response of immune system cells to external or internal stimuli (e.g., antigen, cytokines, chemokines, and other cells) producing biochemical changes in the immune cells that result in immune cell migration, killing of target cells, phagocytosis, production of antibodies, other soluble effectors of the immune response, and the like.

"T lymphocyte response" and "T lymphocyte activity" are used here interchangeably to refer to the component of immune response dependent on T lymphocytes (i.e., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

"Immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

"Inflammation" or "inflammatory response" refers to an innate immune response that occurs when tissues are injured by bacteria, trauma, toxins, heat, or any other cause. The damaged tissue releases compounds including histamine, bradykinin, and serotonin. Inflammation refers to both acute responses (i.e., responses in which the inflammatory processes are active) and chronic responses (i.e., responses marked by slow progression and formation of new connective tissue). Acute and chronic inflammation can be distinguished by the cell types involved. Acute inflammation often involves polymorphonuclear neutrophils; whereas chronic inflammation is normally characterized by a lymphohistiocytic and/or granulomatous response. Inflammation includes reactions of both the specific and non-specific defense systems. A specific defense system reaction is a specific immune system reaction response to an antigen (possibly including an autoantigen). A non-specific defense system reaction is an inflammatory response mediated by leukocytes incapable of immunological memory. Such cells include granulocytes, macrophages, neutrophils and eosinophils. Examples of specific types of inflammation are diffuse inflammation, focal inflammation, croupous inflammation, interstitial inflammation, obliterative inflammation, parenchymatous inflammation, reactive inflammation, specific inflammation, toxic inflammation and traumatic inflammation.

"Patient", "subject" or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

"Treating" or "treatment" includes the administration of the compositions, compounds or agents of the present invention to prevent or delay the onset of the symptoms, complications, or biochemical indicia of a disease, alleviating or ameliorating the symptoms or arresting or inhibiting further development of the disease, condition, or disorder (e.g., an autoimmune disease). "Treating" further refers to any indicia of success in the treatment or amelioration or prevention of the disease, condition, or disorder (e.g., an autoimmune disease), including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with an autoimmune disease. The term "therapeutic effect" refers to the reduction, elimination, or prevention of the disease, symptoms of the disease, or side effects of the disease in the subject. "Treating" or "treatment" using the methods of the present invention includes preventing the onset of symptoms in a subject that can be at increased risk of an autoimmune disease but does not yet experience or exhibit symptoms, inhibiting the symptoms of an autoimmune disease (slowing or arresting its development), providing relief from the symptoms or side-effects of autoimmune disease (including palliative treatment), and relieving the symptoms of autoimmune disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition.

"Inhibitors," "activators," and "modulators" of Toll-like receptors in cells are used to refer to inhibitory, activating, or modulating molecules, respectively, identified using in vitro and in vivo assays for Toll-like receptors binding or signaling, e.g., ligands, agonists, antagonists, and their homologs and mimetics.

The term "modulator" includes inhibitors and activators. Inhibitors are agents that, e.g., bind to, partially or totally block stimulation, decrease, prevent, delay activation, inactivate, desensitize, or down regulate the activity of Toll-like receptors, e.g., antagonists. Activators are agents that, e.g., bind to, stimulate, increase, open, activate, facilitate, enhance activation, sensitize or up regulate the activity of Toll-like receptors, e.g., agonists. Modulators include agents that, e.g., alter the interaction of Toll-like receptor with: proteins that bind activators or inhibitors, receptors, including proteins, peptides, lipids, carbohydrates, polysaccharides, or combinations of the above, e.g., lipoproteins, glycoproteins, and the like. Modulators include genetically modified versions of naturally-occurring Toll-like receptor ligands, e.g., with altered activity, as well as naturally occurring and synthetic ligands, antagonists, agonists, small chemical molecules and the like. Such assays for inhibitors and activators include, e.g., applying putative modulator compounds to a cell expressing a Toll-like receptor and then determining the functional effects on Toll-like receptor signaling, as described herein. Samples or assays comprising Toll-like receptor that are treated with a potential activator, inhibitor, or modulator are compared to control samples without the inhibitor, activator, or modulator to examine the extent of inhibition. Control samples (untreated with inhibitors) can be assigned a relative Toll-like receptor activity value of 100%. Inhibition of Toll-like receptor is achieved when the Toll-like receptor activity value relative to the control is about 80%, optionally 50% or 25-0%. Activation of Toll-like receptor is achieved when the Toll-like receptor activity value relative to the control is 110%, optionally 150%, optionally 200-500%, or 1000-3000% higher.

The ability of a molecule to bind to Toll-like receptor can be determined, for example, by the ability of the putative ligand to bind to Toll-like receptor immunoadhesin coated on an assay plate. Specificity of binding can be determined by comparing binding to non-Toll-like receptor.

In one embodiment, antibody binding to Toll-like receptor can be assayed by either immobilizing the ligand or the receptor. For example, the assay can include immobilizing Toll-like receptor fused to a His tag onto Ni-activated NTA resin beads. Antibody can be added in an appropriate buffer and the beads incubated for a period of time at a given temperature. After washes to remove unbound material, the bound protein can be released with, for example, SDS, buffers with a high pH, and the like and analyzed.

"Inhibitors," "activators," and "modulators" of Toll-like receptor 3-signaling, Toll-like receptor 7-signaling, or Toll-like receptor 9-signaling activity via unc-93A, unc-93B, or unc-93C are used to refer to inhibitory, activating, or modulating molecules, respectively, identified using in vitro and in vivo assays for unc-93a, unc-93b, or unc-93c binding or signaling, e.g., ligands, agonists, antagonists, and their homologs and mimetics. "Modulator" includes inhibitors and activators. Inhibitors are agents that, e.g., bind to, partially or totally block stimulation, decrease, prevent, delay activation, inactivate, desensitize, or down regulate the activity of Toll-like receptor 3-signaling, Toll-like receptor 7-signaling, or Toll-like receptor 9-signaling, e.g., antagonists. Activators are agents that, e.g., bind to, stimulate, increase, open, activate, facilitate, enhance activation, sensitize or up regulate the activity of Toll-like receptor 3-signaling, Toll-like receptor 7-signaling, or Toll-like receptor 9-signaling, e.g., agonists. Modulators include agents that, e.g., alter the interaction of Toll-like receptor 3, Toll-like receptor 7, or Toll-like receptor 9 with: proteins that bind activators or inhibitors, receptors, including proteins, peptides, lipids, carbohydrates, polysaccharides, or combinations of the above, e.g., lipoproteins, glycoproteins, and the like. Modulators include genetically modified versions of naturally-occurring Toll-like receptor 3, Toll-like receptor 7, or Toll-like receptor 9 ligands, e.g., unc-93a, unc-93b, or unc-93c, with altered activity, as well as naturally occurring and synthetic ligands, antagonists, agonists, small chemical molecules and the like. Such assays for inhibitors and activators include, e.g., applying putative modulator compounds to a cell expressing unc-93a, unc-93b, or unc-93c and then determining the functional effects on Toll-like receptor 3, Toll-like receptor 7, or Toll-like receptor 9 signaling, as described herein. Samples or assays comprising unc-93a, unc-93b, or unc-93c and Toll-like receptor 3, Toll-like receptor 7, or Toll-like receptor 9 that are treated with a potential activator, inhibitor, or modulator are compared to control samples without the inhibitor, activator, or modulator to examine the extent of inhibition. Control samples (untreated with inhibitors) can be assigned a relative Toll-like receptor activity value of 100%. Inhibition of TNFRII/CD120b is achieved when the Toll-like receptor activity value relative to the control is about 80%, optionally 50% or 25-0%. Activation of Toll-like receptor 3, Toll-like receptor 7, or Toll-like receptor 9 is achieved when the Toll-like receptor activity value relative to the control is 110%, optionally 150%, optionally 200-500%, or 1000-3000% higher.

"Antagonist" is used in the broadest sense, and includes any molecule that partially or fully blocks, inhibits, or neutralizes a biological activity of a unc-93a polypeptide, unc-93b polypeptide, or unc-93c polypeptide or Toll-like receptor 3 signaling, Toll-like receptor 7 signaling, or Toll-like receptor 9 signaling. In a similar manner, the term "agonist" is used in the broadest sense and includes any molecule that mimics or enhances a biological activity of a unc-93a polypeptide, unc-93b polypeptide, or unc-93c polypeptide or Toll-like receptor 3-signaling, Toll-like receptor 7-signaling, or Toll-like receptor 9-signaling. Suitable agonist or antagonist molecules specifically include agonist or antagonist antibodies or antibody fragments, fragments or amino acid sequence variants of native unc-93a polypeptides, unc-93b polypeptides, or unc-93c polypeptides, peptides, antisense oligonucleotides, small organic molecules, and the like. Methods for identifying agonists or antagonists of unc-93a polypeptides, unc-93b polypeptides, or unc-93c polypeptides can comprise contacting an unc-93a polypeptide, unc-93b polypeptide, or unc-93c polypeptide with a candidate agonist or antagonist molecule and measuring a detectable change in one or more biological activities normally associated with the unc-93a polypeptide, unc-93b polypeptide, or unc-93c polypeptide.

"Signaling in cells" refers to the interaction of a ligand, such as an endogenous or exogenous ligand, e.g., unc-93a, unc-93b, or unc-93c with receptors, such as Toll-like receptor 3-signaling, Toll-like receptor 7-signaling, or Toll-like receptor 9-signaling pathways resulting in cell signaling to produce a response, for example, an autoimmune response, inflammatory response, infectious disease or CD8 cell or CD4 cell signaling defect.

"Test compound" refers to a nucleic acid, DNA, RNA, protein, polypeptide, or small chemical entity that is determined to effect an increase or decrease in a gene expression as a result of signaling through the Toll-like receptor 3-signaling pathway, Toll-like receptor 7-signaling pathway, or Toll-like receptor 9-signaling pathway. The test compound can be an antisense RNA, ribozyme, polypeptide, or small molecular chemical entity. The term "test compound" can be any small chemical compound, or a biological entity, such as a protein, sugar, nucleic acid or lipid. Typically, test compounds will be small chemical molecules and polypeptides. A "test compound specific for Toll-like receptor 3-signaling, Toll-like receptor 7-signaling, or Toll-like receptor 9-signaling" is determined to be a modulator of TNFRII/CD120b pathway signaling via TNF-α.

"Cell-based assays" include Toll-like receptor 3, Toll-like receptor 7, or Toll-like receptor 9 binding assays, for example, radioligand or fluorescent ligand binding assays for Toll-like receptor 3-signaling, Toll-like receptor 7-signaling, or Toll-like receptor 9-signaling activity via unc-93A, unc-93B, or unc-93C in cells, plasma membranes, detergent-solubilized plasma membrane proteins, immobilized collagen (Alberdi, *J Biol Chem.* 274:31605-12, 1999; Meyer et al., 2002); TNFRII/CD120b -affinity column chromatography (Alberdi, *J Biol Chem.* 274:31605-12, 1999; Aymerich et al., *Invest Ophthalmol Vis Sci.* 42:3287-93, 2001); TNFRII/CD120b ligand blot using a radio- or fluorosceinated-ligand (Aymerich et al., *Invest Ophthalmol Vis Sci.* 42:3287-93, 2001; Meyer et al., 2002); Size-exclusion ultrafiltration (Alberdi et al., *Biochem.,* 1998; Meyer et al., 2002); or ELISA. Exemplary TNFRII/CD120b binding activity assays of the present invention are: a TNF-α/TNFRII/CD120b ligand blot assay (Aymerich et al., *Invest Ophthalmol Vis Sci.* 42:3287-93, 2001); a TNFRII/CD120b affinity column chromatography assay (Alberdi, *J Biol Chem.* 274:31605-12, 1999) and a TNF-α/TNFRII/CD120b ligand binding assay (Alberdi et al., *J Biol Chem.* 274:31605-12, 1999). Each incorporated by reference in their entirety.

In one embodiment, Toll-like receptor 3-signaling, Toll-like receptor 7-signaling, or Toll-like receptor 9-signaling activity via unc-93A, unc-93B, or unc-93C can be assayed by either immobilizing the ligand or the receptor. For example, the assay can include immobilizing Toll-like receptor 3, Toll-like receptor 7, or Toll-like receptor 9 fused to a His tag onto Ni-activated NTA resin beads. unc-93a polypeptide, unc-93b polypeptide, or unc-93c polypeptide can be added in an appropriate buffer and the beads incubated for a period of time at a given temperature. After washes to remove unbound material, the bound protein can be released with, for example, SDS, buffers with a high pH, and the like and analyzed.

"Contacting" refers to mixing a test compound in a soluble form into an assay system, for example, a cell-based assay system, such that an effect upon receptor-mediated signaling can be measured.

"Signaling responsiveness" or "effective to activate signaling" or "stimulating a cell-based assay system" refers to the ability of Toll-like receptor 3-signaling, Toll-like receptor 7-signaling, or Toll-like receptor 9-signaling activity via unc-93A, unc-93B, or unc-93C to inhibit or enhance an immune response, or treat autoimmune disease, an infectious disease, an inflammatory disease, an antigen presenting cell defect, a CD8 cell defect, or a CD4 cell defect.

"Detecting an effect" refers to an effect measured in a cell-based assay system. For example, the effect detected can be Toll-like receptor 3-signaling, Toll-like receptor 7-signaling, or Toll-like receptor 9-signaling in an assay system, for example, TNF cellular assay, Toll-like receptor 3, Toll-like receptor 7, or Toll-like receptor 9 binding assay.

"Assay being indicative of modulation" refers to results of a cell-based assay system indicating that cell activation by Toll-like receptor 3-signaling, Toll-like receptor 7-signaling, or Toll-like receptor 9-signaling activity via unc-93A, unc-93B, or unc-93C induces a protective response in cells against autoimmune disease, an infectious disease, an inflammatory disease, an antigen presenting cell defect, a CD8 cell defect, or a CD4 cell defect.

"Biological activity" and "biologically active" with regard to a ligand of Toll-like receptor 3-signaling, Toll-like receptor 7-signaling, or Toll-like receptor 9-signaling activity via unc-93A, unc-93B, or unc-93C of the present invention refer to the ability of the ligand molecule to specifically bind to and signal through a native or recombinant Toll-like receptor 3, Toll-like receptor 7, or Toll-like receptor 9, or to block the ability of a native or recombinant Toll-like receptor 3, Toll-like receptor 7, or Toll-like receptor 9 to participate in signal transduction.

Thus, the (native and variant) ligands of Toll-like receptor 3, Toll-like receptor 7, or Toll-like receptor 9 of the present invention include agonists and antagonists of a native or recombinant TNFRII/CD120b. Preferred biological activities of the ligands of Toll-like receptor 3, Toll-like receptor 7, or Toll-like receptor 9 of the present invention include the ability to induce or inhibit, for example, inhibiting or enhancing an immune response, or treating autoimmune disease, an infectious disease, an inflammatory disease, an antigen presenting cell defect, a CD8 cell defect, or a CD4 cell defect. Accordingly, the administration of the compounds or agents of the present invention can prevent or delay, to alleviate, or to arrest or inhibit development of the symptoms or conditions associated with autoimmune disease, an infectious disease, an inflammatory disease, an antigen presenting cell defect, a CD8 cell defect, or a CD4 cell defect, or other disorders.

"Concomitant administration" of a known drug with a compound of the present invention means administration of the drug and the compound at such time that both the known drug and the compound will have a therapeutic effect or diagnostic effect. Such concomitant administration can involve concurrent (i.e. at the same time), prior, or subsequent administration of the drug with respect to the administration of a compound of the present invention. A person of ordinary skill in the art, would have no difficulty determining the appropriate timing, sequence and dosages of administration for particular drugs and compounds of the present invention.

In general, the phrase "well tolerated" refers to the absence of adverse changes in health status that occur as a result of the treatment and would affect treatment decisions.

"Lymphocyte" as used herein has the normal meaning in the art, and refers to any of the mononuclear, nonphagocytic leukocytes, found in the blood, lymph, and lymphoid tissues, i.e., B and T lymphocytes.

"Subpopulations of T lymphocytes" or "T cell subset(s)" refers to T lymphocytes or T cells characterized by the expression of particular cell surface markers (see Barclay, A. N. et al., (eds.), THE LEUKOCYTE ANTIGEN FACTS BOOK, $2^{ND}$. EDITION, Academic Press, London, United Kingdom, 1997; this reference is herein incorporated by reference for all purposes).

"Epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

An intact "antibody" comprises at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) through cellular receptors such as Fc receptors (e.g., FcγRI, FcγRIIa, FcγRIIb, FcγRIII, and FcRη) and the first component (Clq) of the classical complement system. The term antibody includes antigen-binding portions of an intact antibody that retain capacity to bind the antigen. Examples of antigen binding portions include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 341:544-546, 1989), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al., Science 242:423-426, 1988; and Huston et al., Proc. Natl. Acad. Sci. U.S.A. 85:5879-5883, 1988). Such single chain antibodies are included by reference to the term "antibody" Fragments can be prepared by recombinant techniques or enzymatic or chemical cleavage of intact antibodies.

"Human sequence antibody" includes antibodies having variable and constant regions (if present) derived from human immunoglobulin sequences. The human sequence antibodies of the invention can include amino acid residues not encoded by human germline immunoglobulin sequences (e.g., mutations introduced by random or site-specific mutagenesis in vitro or by somatic mutation in vivo). However, the term "human sequence antibody", as used herein, is not intended to include antibodies in which entire CDR sequences sufficient to confer antigen specificity and derived from the germline of another mammalian species, such as a mouse, have been grafted onto human framework sequences (i.e., humanized antibodies).

"Monoclonal antibody" or "monoclonal antibody composition" refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

"Diclonal antibody" refers to a preparation of at least two antibodies to an antigen. Typically, the different antibodies bind different epitopes.

"Oligoclonal antibody" refers to a preparation of 3 to 100 different antibodies to an antigen. Typically, the antibodies in such a preparation bind to a range of different epitopes.

"Polyclonal antibody" refers to a preparation of more than 1 (two or more) different antibodies to an antigen. Such a preparation includes antibodies binding to a range of different epitopes.

"Recombinant human antibody" includes all human sequence antibodies of the invention that are prepared, expressed, created or isolated by recombinant means, such as antibodies isolated from an animal (e.g., a mouse) that is transgenic for human immunoglobulin genes (described further below); antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

A "heterohybrid antibody" refers to an antibody having a light and heavy chains of different organismal origins. For example, an antibody having a human heavy chain associated with a murine light chain is a heterohybrid antibody.

"Substantially pure" or "isolated" means an object species (e.g., an antibody of the invention) has been identified and separated and/or recovered from a component of its natural environment such that the object species is the predominant species present (i.e., on a molar basis it is more abundant than any other individual species in the composition); a "substantially pure" or "isolated" composition also means where the object species comprises at least about 50 percent (on a molar basis) of all macromolecular species present. A substantially pure or isolated composition can also comprise more than about 80 to 90 percent by weight of all macromolecular species present in the composition. An isolated object species (e.g., antibodies of the invention) can also be purified to essential homogeneity (contaminant species cannot be detected in the composition by conventional detection methods) wherein the composition consists essentially of derivatives of a single macromolecular species. For example, an isolated antibody to 3d can be substantially free of other antibodies that lack binding to human 3d and bind to a different antigen. Further, an isolated antibody that specifically binds to an epitope, isoform or variant of human 3d may, however, have cross-reactivity to other related antigens, e.g., from other species (e.g., 3d species homologs). Moreover, an isolated antibody of the invention be substantially free of other cellular material (e.g., non-immunoglobulin associated proteins) and/or chemicals.

"Specific binding" refers to preferential binding of an antibody to a specified antigen relative to other non-specified antigens. The phrase "specifically (or selectively) binds" to an antibody refers to a binding reaction that is determinative of the presence of the protein in a heterogeneous population of proteins and other biologics. Typically, the antibody binds with an association constant ($K_a$) of at least about $1 \times 10^6 M^{-1}$ or $10^{7\ M^{-1}}$, or about $10^8 M^{-1}$ to $10^9 M^{-1}$, or about $10^{10} M^{-1}$ to $10^{11} M^{-1}$ or higher, and binds to the specified antigen with an affinity that is at least two-fold greater than its affinity for binding to a non-specific antigen (e.g., BSA, casein) other than the specified antigen or a closely-related antigen. The phrases "an antibody recognizing an antigen" and "an antibody specific for an antigen" are used interchangeably herein with the term "an antibody which binds specifically to an antigen". A predetermined antigen is an antigen that is chosen prior to the selection of an antibody that binds to that antigen.

"Specifically bind(s)" or "bind(s) specifically" when referring to a peptide refers to a peptide molecule which has intermediate or high binding affinity, exclusively or predominately, to a target molecule. The phrases "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions can require a binding moiety that is selected for its specificity for a particular target antigen. A variety of assay formats can be used to select ligands that are specifically reactive with a particular protein. For example, solid-phase ELISA immunoassays, immunoprecipitation, Biacore and Western blot are used to identify peptides that specifically react with the antigen. Typically a specific or selective reaction will be at least twice background signal or noise and more typically more than 10 times background.

"High affinity" for an antibody refers to an equilibrium association constant ($K_a$) of at least about $10^7 M^{-1}$, at least about $10^8 M^{-1}$, at least about $10^9 M^{-1}$, at least about $10^{10} M^{-1}$, at least about $10^{11} M^{-1}$, or at least about $10^{12} M^{-1}$ or greater, e.g., up to $10^{13} M^{-1}$ or $10^{14} M^{-1}$ or greater. However, "high affinity" binding can vary for other antibody isotypes.

The term "$K_a$", as used herein, is intended to refer to the equilibrium association constant of a particular antibody-antigen interaction. This constant has units of 1/M.

The term "$K_d$", as used herein, is intended to refer to the equilibrium dissociation constant of a particular antibody-antigen interaction. This constant has units of M.

The term "$k_a$", as used herein, is intended to refer to the kinetic association constant of a particular antibody-antigen interaction. This constant has units of 1/Ms.

The term "$k_d$", as used herein, is intended to refer to the kinetic dissociation constant of a particular antibody-antigen interaction. This constant has units of 1/s.

"Particular antibody-antigen interactions" refers to the experimental conditions under which the equilibrium and kinetic constants are measured.

"Isotype" refers to the antibody class that is encoded by heavy chain constant region genes. Heavy chains are classified as gamma, mu, alpha, delta, or epsilon, and define the antibody's isotype as IgG, IgM, IgA, IgD and IgE, respectively. Additional structural variations characterize distinct subtypes of IgG (e.g., $IgG_1$, $IgG_2$, $IgG_3$ and $IgG_4$) and IgA (e.g., $IgA_1$ and $IgA_2$)

"Isotype switching" refers to the phenomenon by which the class, or isotype, of an antibody changes from one Ig class to one of the other Ig classes.

"Nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching can occur by, for example, homologous recombination between human $\sigma_\mu$ and human $\Sigma_\mu$ (δ-associated deletion). Alternative non-classical switching mechanisms, such as intertransgene and/or interchromosomal recombination, among others, can occur and effectuate isotype switching.

"Switch sequence" refers to those DNA sequences responsible for switch recombination. A "switch donor" sequence, typically a μ switch region, are 5' (i.e., upstream) of the construct region to be deleted during the switch recombination. The "switch acceptor" region are between the construct region to be deleted and the replacement constant region (e.g., γ, ε, and alike). As there is no specific site where recombination always occurs, the final gene sequence is not typically predictable from the construct.

"Glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the non-human transgenic animal, when one of ordinary skill in the art would recognize the glycosylation pattern of the heterologous antibody as being more similar to said pattern of glycosylation in the species of the non-human transgenic animal than to the species from which the CH genes of the transgene were derived.

"Naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Immunoglobulin locus" refers to a genetic element or set of linked genetic elements that comprise information that can be used by a B cell or B cell precursor to express an immunoglobulin peptide. This peptide can be a heavy chain peptide, a light chain peptide, or the fusion of a heavy and a light chain peptide. In the case of an unrearranged locus, the genetic elements are assembled by a B cell precursor to form the gene encoding an immunoglobulin peptide. In the case of a rearranged locus, a gene encoding an immunoglobulin peptide is contained within the locus.

"Rearranged" refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus has at least one recombined heptamer/nonamer homology element.

"Unrearranged" or "germine configuration" in reference to a V segment refers to the configuration wherein the V segment is not recombined so as to be immediately adjacent to a D or J segment.

"Nucleic acid" or "nucleic acid molecule" refer to a deoxyribonucleotide or ribonucleotide polymer in either single- or double-stranded form, and unless otherwise limited, can encompass known analogs of natural nucleotides that can function in a similar manner as naturally occurring nucleotides.

"Isolated nucleic acid" in reference to nucleic acids encoding antibodies or antibody portions (e.g., VH, VL, CDR3) that bind to the antigen, is intended to refer to a nucleic acid in which the nucleotide sequences encoding the antibody or antibody portion are free of other nucleotide sequences encoding antibodies or antibody portions that bind antigens other than, for example, 3d, which other sequences can naturally flank the nucleic acid in human genomic DNA.

"Substantially identical," in the context of two nucleic acids or polypeptides refers to two or more sequences or subsequences that have at least about 80%, about 90%, about 95% or higher nucleotide or amino acid residue identity, when compared and aligned for maximum correspondence, as measured using the following sequence comparison method and/or by visual inspection. Such "substantially identical" sequences are typically considered to be homologous. The "substantial identity" can exist over a region of sequence that is at least about 50 residues in length, over a region of at least about 100 residues, or over a region at least about 150 residues, or over the full length of the two sequences to be compared. As described below, any two antibody sequences can only be aligned in one way, by using the numbering scheme in Kabat. Therefore, for antibodies, percent identity has a unique and well-defined meaning.

Amino acids from the variable regions of the mature heavy and light chains of immunoglobulins are designated Hx and Lx respectively, where x is a number designating the position of an amino acid according to the scheme of Kabat, Sequences of Proteins of Immunological Interest (National Institutes of Health, Bethesda, Md., 1987 and 1991). Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Likewise, nucleic acids encoding antibody chains are aligned when the amino acid sequences encoded by the respective nucleic acids are aligned according to the Kabat numbering convention. An alternative structural definition has been proposed by Chothia, et al., *J. Mol. Biol.* 196:901-917, 1987; Chothia, et al., *Nature* 342:878-883, 1989; and Chothia, et al., *J. Mol. Biol.* 186:651-663, 1989, which are herein incorporated by reference for all purposes.

The nucleic acids of the invention be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art (See, e.g., Sambrook, Tijssen and Ausubel discussed herein and incorporated by reference for all purposes). The nucleic acid sequences of the invention and other nucleic acids used to practice this invention, whether RNA, cDNA, genomic DNA, or hybrids thereof, can be isolated from a variety of sources, genetically engineered, amplified, and/or expressed recombinantly. Any recombinant expression system can be used, including, in addition to bacterial, e.g., yeast, insect or mammalian systems. Alternatively, these nucleic acids can be chemically synthesized in vitro. Techniques for the manipulation of nucleic acids, such as, e.g., subcloning into expression vectors, labeling probes, sequencing, and hybridization are well described in the scientific and patent literature, see, e.g., Sambrook, Tijssen and Ausubel. Nucleic acids can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassay (RIAs), enzyme-linked immunosorbent assays (ELISAs), immunofluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

The nucleic acid compositions of the present invention, while often in a native sequence (except for modified restriction sites and the like), from either cDNA, genomic or mixtures can be mutated, thereof in accordance with standard techniques to provide gene sequences. For coding sequences, these mutations, can affect amino acid sequence as desired. In particular, DNA sequences substantially homologous to or derived from native V, D, J, constant, switches and other such sequences described herein are contemplated (where "derived" indicates that a sequence is identical or modified from another sequence).

"Recombinant host cell" or "host cell" refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

A "label" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins for which antisera or monoclonal antibodies are available (e.g., the polypeptides of the invention can be made detectable, e.g., by incorporating a radiolabel into the peptide, and used to detect antibodies specifically reactive with the peptide).

"Sorting" in the context of cells as used herein to refers to both physical sorting of the cells, as can be accomplished using, e.g., a fluorescence activated cell sorter, as well as to analysis of cells based on expression of cell surface markers, e.g., FACS analysis in the absence of sorting.

Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity, (2) helper T lymphocytes can be incubated with antigens and antigen presenting cells and the synthesis and secretion of cytokines measured by standard methods (Windhagen A; et al., Immunity 2:373-80, 1995), (3) antigen presenting cells can be incubated with whole protein antigen and the presentation of that antigen on MHC detected by either T lymphocyte activation assays or biophysical methods (Harding et al., *Proc. Natl. Acad. Sci. U.S.A.*, 86:4230-4, 1989), (4) mast cells can be incubated with reagents that cross-link their Fc-epsilon receptors and histamine release measured by enzyme immunoassay (Siraganian, et al., TIPS 4:432-437, 1983).

Similarly, products of an immune response in either a model organism (e.g., mouse) or a human patient can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., Blood 72:1310-5, 1988); (3) the proliferation of peripheral blood mononuclear cells in response to mitogens or mixed lymphocyte reaction can be measured using $^3$H-thymidine; (4) the phagocitic capacity of granulocytes, macrophages, and other phagocytes in PBMCs can be measured by placing PMBCs in wells together with labeled particles (Peters et al., 1988); and (5) the radioimmunoassa of immune system cells can be measured by labeling PBMCs with antibodies to CD molecules such as CD4 and CD8 and measuring the fraction of the PBMCs expressing these markers.

As used herein, the phrase "signal transduction pathway" or "signal transduction event" refers to at least one biochemical reaction, but more commonly a series of biochemical reactions, which result from interaction of a cell with a stimulatory compound or agent. Thus, the interaction of a stimulatory compound with a cell generates a "signal" that is transmitted through the signal transduction pathway, ultimately resulting in a cellular response, e.g., an immune response described above.

A signal transduction pathway refers to the biochemical relationship between a variety of signal transduction molecules that play a role in the transmission of a signal from one portion of a cell to another portion of a cell. As used herein, the phrase "cell surface receptor" includes molecules and complexes of molecules capable of receiving a signal and the transmission of such a signal across the plasma membrane of a cell. An example of a "cell surface receptor" is the T cell receptor (TCR) or the B7 ligands of CTLA-4.

A signal transduction pathway in a cell can be initiated by interaction of a cell with a stimulator that is inside or outside of the cell. If an exterior (i.e., outside of the cell) stimulator (e.g., an MHC-antigen complex on an antigen presenting cell) interacts with a cell surface receptor (e.g., a T cell receptor), a signal transduction pathway can transmit a signal across the cell's membrane, through the cytoplasm of the cell, and in some instances into the nucleus. If an interior (e.g., inside the cell) stimulator interacts with an intracellular signal transduction molecule, a signal transduction pathway can result in transmission of a signal through the cell's cytoplasm, and in some instances into the cell's nucleus. An example of a signal transduction pathway is the Toll-like receptor (TLR) pathway, e.g., TLR-3, TLR-7, or TLR-9.

Signal transduction can occur through, e.g., the phosphorylation of a molecule; non-covalent allosteric interactions; complexing of molecules; the conformational change of a molecule; calcium release; inositol phosphate production; proteolytic cleavage; cyclic nucleotide production and diacylglyceride production. Typically, signal transduction occurs through phosphorylating a signal transduction molecule.

"Nonspecific T cell activation" refers to the stimulation of T cells independent of their antigenic specificity.

This invention relies on routine techniques in the field of recombinant genetics. Basic texts disclosing the general methods of use in this invention include Sambrook et al., *Molecular Cloning, A Laboratory Manual, 2$^{nd}$ ed.*, 1989;

Kriegler, *Gene Transfer and Expression: A Laboratory Manual*, 1990; and Ausubel et al., eds., *Current Protocols in Molecular Biology*, 1994.

3d, a mutant of unc-93B, unc-93A, unc-93B, or unc-93C, nucleic acids, polymorphic variants, orthologs, and alleles that are substantially identical to sequences provided herein can be isolated using nucleic acid probes and oligonucleotides of 3d, unc-93A, unc-93B, or unc-93C, under stringent hybridization conditions, by screening libraries. Alternatively, expression libraries can be used to clone 3d protein, or protein encoding unc-93A, unc-93B, or unc-93C, polymorphic variants, orthologs, and alleles by detecting expressed homologs immunologically with antisera or purified antibodies made against human 3d, unc-93A, unc-93B, or unc-93C, or portions thereof.

2. General Techniques

The nucleic acids used to practice this invention, whether RNA, iRNA, antisense nucleic acid, cDNA, genomic DNA, vectors, viruses or hybrids thereof, can be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams, *J. Am. Chem. Soc.* 105:661, 1983; Belousov, *Nucleic Acids Res.* 25:3440-3444, 1997; Frenkel, *Free Radic. Biol. Med.* 19:373-380, 1995; Blommers, *Biochemistry* 33:7886-7896, 1994; Narang, *Meth. Enzymol.* 68:90, 1979; Brown *Meth. Enzymol.* 68:109, 1979; Beaucage, *Tetra. Lett.* 22:1859, 1981; U.S. Pat. No. 4,458,066.

The invention provides oligonucleotides comprising sequences of the invention, e.g., subsequences of the exemplary sequences of the invention. Oligonucleotides can include, e.g., single stranded poly-deoxynucleotides or two complementary polydeoxynucleotide strands which can be chemically synthesized.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL ($2^{ND}$ ED.), Vols. 1-3, Cold Spring Harbor Laboratory, 1989; CURRENT PROTOCOLS IN MOLECULAR BIOLOGY, Ausubel, ed. John Wiley & Sons, Inc., New York, 1997; LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y., 1993.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, □adioimmunoassay (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabeling, scintillation counting, and affinity chromatography.

Obtaining and manipulating nucleic acids used to practice the methods of the invention can be done by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld, *Nat. Genet.* 15:333-335, 1997; yeast artificial chromosomes (YAC); bacterial artificial chromosomes (BAC); P1 artificial chromosomes, see, e.g., Woon, *Genomics* 50:306-316, 1998; P1-derived vectors (PACs), see, e.g., Kern, *Biotechniques* 23:120-124, 1997; cosmids, recombinant viruses, phages or plasmids.

The invention provides fusion proteins and nucleic acids encoding them. An unc-93, unc-93a, unc-93b, or unc-93c polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams, *Biochemistry* 34:1787-1797, 1995; Dobeli, *Protein Expl. Purif* 12:404-414, 1998). The histidine residues facilitate detection and purification while the enterokinase cleavage site provides a means for purifying the epitope from the remainder of the fusion protein. In one aspect, a nucleic acid encoding a polypeptide of the invention is assembled in appropriate phase with a leader sequence capable of directing secretion of the translated polypeptide or fragment thereof. Technology pertaining to vectors encoding fusion proteins and application of fusion proteins are well described in the scientific and patent literature, see e.g., Kroll, *DNA Cell. Biol.* 12:441-53, 1993.

3. Transcriptional Control Elements

The nucleic acids of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

4. Expression Vectors and Cloning Vehicles

The invention provides expression vectors and cloning vehicles comprising nucleic acids of the invention, e.g., sequences encoding the proteins of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" a PCR primer pair.

The invention provides libraries of expression vectors encoding polypeptides and peptides of the invention. These nucleic acids can be introduced into a genome or into the cytoplasm or a nucleus of a cell and expressed by a variety of conventional techniques, well described in the scientific and patent literature. See, e.g., Roberts, *Nature* 328:731, 1987; Schneider, *Protein Expr. Purif.* 6435:10, 1995; Sambrook, Tijssen or Ausubel. The vectors can be isolated from natural sources, obtained from such sources as ATCC or GenBank libraries, or prepared by synthetic or recombinant methods. For example, the nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids of the invention are administered in vivo for in situ expression of the peptides or polypeptides of the invention. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. Chimeric vectors can also be employed which exploit advantageous merits of each of the parent vector properties (See e.g., Feng, *Nature Biotechnology* 15:866-870, 1997). Such viral genomes can be modified by recombinant DNA techniques to include the nucleic acids of the invention; and can be further engineered to be replication deficient, conditionally replicating or replication competent. In alternative aspects, vectors are derived from the adenoviral (e.g., replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher, *J. Virol.* 66:2731-2739, 1992; Johann, *J. Virol.* 66:1635-1640, 1992). Adeno-associated virus (AAV)-based vectors can be used to □adioimmun cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada, *Gene Ther.* 3:957-964, 1996.

"Expression cassette" as used herein refers to a nucleotide sequence which is capable of affecting expression of a structural gene (i.e., a protein coding sequence, such as a polypeptide of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression can also be used, e.g., enhancers.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination. Thus, expression cassettes also include plasmids, expression vectors, recombinant viruses, any form of recombinant "naked DNA" vector, and the like.

"Vector" is intended to refer to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

5. Host Cells and Transformed Cells

The invention also provides a transformed cell comprising a nucleic acid sequence of the invention, e.g., a sequence encoding a polypeptide of the invention, or a vector of the invention. The host cell can be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces,* and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter can be induced by appropriate means (e.g., temperature shift or chemical induction) and the cells can be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct can be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

6. Amplification of Nucleic Acids

In practicing the invention, nucleic acids encoding the polypeptides of the invention, or modified nucleic acids, can be reproduced by, e.g., amplification. The invention provides amplification primer sequence pairs for amplifying nucleic acids encoding polypeptides of the invention, e.g., primer pairs capable of amplifying nucleic acid sequences comprising the exemplary SEQ ID NO:1 or SEQ ID NO:3, or subsequences thereof.

Amplification methods include, e.g., polymerase chain reaction, PCR (PCR PROTOCOLS, A GUIDE TO METHODS AND APPLICATIONS, ed. Innis, Academic Press, N.Y., 1990 and PCR STRATEGIES, 1995, ed. Innis, Academic Press, Inc., N.Y., ligase chain reaction (LCR) (see, e.g., Wu, *Genomics* 4:560, 1989; Landegren, *Science* 241:1077, 1988; Barringer, *Gene* 89:117, 1990); transcription amplification (see, e.g., Kwoh, *Proc. Natl. Acad. Sci. USA* 86:1173, 1989); and, self-sustained sequence replication (see, e.g., Guatelli, *Proc. Natl. Acad. Sci. USA* 87:1874, 1990); Q Beta replicase amplification (see, e.g., Smith, *J. Clin. Microbiol.* 35:1477-1491, 1997), automated Q-beta replicase amplification assay (see, e.g., Burg, *Mol. Cell. Probes* 10:257-271, 1996) and other RNA polymerase mediated techniques (e.g., NASBA, Cangene, Mississauga, Ontario); see also Berger, *Methods Enzymol.* 152:307-316, 1987; Sambrook; Ausubel; U.S. Pat. Nos. 4,683,195 and 4,683,202; Sooknanan, *Biotechnology* 13:563-564, 1995.

7. Hybridization of Nucleic Acids

The invention provides isolated or recombinant nucleic acids that hybridize under stringent conditions to an exemplary sequence of the invention, e.g., a sequence as set forth in SEQ ID NO:1 or SEQ ID NO:3, or the complement of any thereof, or a nucleic acid that encodes a polypeptide of the invention. In alternative aspects, the stringent conditions are highly stringent conditions, medium stringent conditions or low stringent conditions, as known in the art and as described herein. These methods can be used to isolate nucleic acids of the invention.

In alternative aspects, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800 or more residues in length, or, the full length of a gene or coding sequence, e.g., cDNA. Nucleic acids shorter than full length are also included. These nucleic acids can be useful as, e.g., hybridization probes, labeling probes, PCR oligonucleotide probes, iRNA, antisense or sequences encoding antibody binding peptides (epitopes), motifs, active sites and the like.

"Selectively (or specifically) hybridizes to" refers to the binding, duplexing, or hybridizing of a molecule to a particular nucleotide sequence under stringent hybridization conditions when that sequence is present in a complex mixture (e.g., total cellular or library DNA or RNA), wherein the particular nucleotide sequence is detected at least at about 10 times background. In one embodiment, a nucleic acid can be determined to be within the scope of the invention by its ability to hybridize under stringent conditions to a nucleic acid otherwise determined to be within the scope of the invention (such as the exemplary sequences described herein).

"Stringent hybridization conditions" refers to conditions under which a probe will hybridize to its target subsequence, typically in a complex mixture of nucleic acid, but not to other sequences in significant amounts (a positive signal (e.g., identification of a nucleic acid of the invention) is about 10 times background hybridization). Stringent conditions are sequence-dependent and will be different in different circumstances. Longer sequences hybridize specifically at higher temperatures. An extensive guide to the hybridization of nucleic acids is found in e.g., Sambrook, ed., MOLECULAR CLONING: A LABORATORY MANUAL ($2^{ND}$ ED.), Vols. 1-3, Cold Spring Harbor Laboratory, 1989; CURRENT PROTOCOLS IN MOLECULAR BIOLOGY, Ausubel, ed. John Wiley & Sons, Inc., New York, 1997; LABORATORY TECHNIQUES IN BIOCHEMISTRY AND MOLECULAR BIOLOGY: HYBRIDIZATION WITH NUCLEIC ACID PROBES, PART I. Theory and Nucleic Acid Preparation, Tijssen, ed. Elsevier, N.Y., 1993.

Generally, stringent conditions are selected to be about 5-10° C. lower than the thermal melting point I for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide as described in Sambrook (cited below). For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. For selective or specific hybridization, a positive signal (e.g., identification of a nucleic acid of the invention) is about 10 times background hybridization. Stringent hybridization conditions that are used to identify nucleic acids within the scope of the invention include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. In the present invention, genomic DNA or cDNA comprising nucleic acids of the invention can be identified in standard Southern blots under stringent conditions using the nucleic acid sequences disclosed here. Additional stringent conditions for such hybridizations (to identify nucleic acids within the scope of the invention) are those which include a hybridization in a buffer of 40% formamide, 1 M NaCl, 1% SDS at 37° C.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g., a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

8. Oligonucleotides Probes and Methods for Using Them

The invention also provides nucleic acid probes for identifying nucleic acids encoding a polypeptide which is a modulator of a Toll-like receptor 3-signaling, Toll-like receptor 7-signaling, or Toll-like receptor 9-signaling activity via unc-93A, unc-93B, or unc-93C. In one aspect, the probe comprises at least 10 consecutive bases of a nucleic acid of the invention. Alternatively, a probe of the invention can be at least about 5, 6, 7, 8, 9, 10, 15, 20, 25, 30, 35, 40, 45, 50, 60, 70, 80, 90, 100, 110, 120, 130, 150 or about 10 to 50, about 20 to 60 about 30 to 70, consecutive bases of a sequence as set forth in a nucleic acid of the invention. The probes identify a nucleic acid by binding and/or hybridization. The probes can be used in arrays of the invention, see discussion below. The probes of the invention can also be used to isolate other nucleic acids or polypeptides.

9. Determining the Degree of Sequence Identity

The invention provides nucleic acids having at least 90%, 91%, 92%, 93%, 94%, 95%, 96%, 97%, 98%, 99% or more sequence identity to SEQ ID NO:1, or SEQ ID NO:3. The invention provides polypeptides having at least 90%, 91%, 92%, 93%, 94%, 95%, 96%, 97%, 98%, 99% or more sequence identity to SEQ ID NO:2 or SEQ ID NO:4. The sequence identities can be determined by analysis with a sequence comparison algorithm or by a visual inspection. Protein and/or nucleic acid sequence identities (homologies) can be evaluated using any of the variety of sequence comparison algorithms and programs known in the art.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.2.2. or FASTA version 3.0t78 algorithms and the default parameters discussed below can be used.

A "comparison window", as used herein, includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2: 482, 1981, by the homology alignment algorithm of Needleman & Wunsch, *J. Mol. Biol.* 48: 443, 1970, by the search for similarity method of Pearson & Lipman, *Proc. Natl. Acad. Sci. U.S.A.* 85: 2444, 1988, by computerized implementations of these algorithms (FASTDB (Intelligenetics), BLAST (National Center for Biomedical Information), GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., (1999 Suppl.), *Current Protocols in Molecular Biology*, Greene Publishing Associates and Wiley Interscience, N.Y., 1987)

A preferred example of an algorithm that is suitable for determining percent sequence identity and sequence similarity is the FASTA algorithm, which is described in Pearson, W. R. & Lipman, D. J., *Proc. Natl. Acad. Sci. U.S.A.* 85: 2444, 1988. See also W. R. Pearson, *Methods Enzymol.* 266: 227-258, 1996. Preferred parameters used in a FASTA alignment of DNA sequences to calculate percent identity are optimized, BL50 Matrix 15: −5, k-tuple=2; joining penalty=40, optimization=28; gap penalty −12, gap length penalty=−2; and width=16.

Another preferred example of algorithm that is suitable for determining percent sequence identity and sequence similarity are the BLAST and BLAST 2.0 algorithms, which are described in Altschul et al., *Nuc. Acids Res.* 25:3389-3402, 1977; and Altschul et al., *J. Mol. Biol.* 215:403-410, 1990, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. U.S.A.* 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Natl. Acad. Sci. U.S.A.* 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another preferred example of an algorithm that is suitable for multiple DNA and amino acid sequence alignments is the CLUSTALW program (Thompson, J. D. et al., *Nucl. Acids. Res.* 22:4673-4680, 1994). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, *Proc. Natl. Acad. Sci. U.S.A.* 89:10915-10919, 1992).

"Sequence identity" refers to a measure of similarity between amino acid or nucleotide sequences, and can be measured using methods known in the art, such as those described below:

"Identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, 91%, 92%, 93%, 94%, 95%, 96%, 97%, 98%, or 99% or more identity over a specified region, when compared and aligned for maximum correspondence over a comparison window, or designated region as measured using one of the following sequence comparison algorithms or by manual alignment and visual inspection.

"Substantially identical," in the context of two nucleic acids or polypeptides, refers to two or more sequences or subsequences that have at least of at least 60%, often at least 70%, preferably at least 80%, most preferably at least 90% or at least 95% nucleotide or amino acid residue identity, when compared and aligned for maximum correspondence, as measured using one of the following sequence comparison algorithms or by visual inspection. Preferably, the substantial identity exists over a region of the sequences that is at least about 50 bases or residues in length, more preferably over a region of at least about 100 bases or residues, and most preferably the sequences are substantially identical over at least about 150 bases or residues. In a most preferred embodiment, the sequences are substantially identical over the entire length of the coding regions.

"Homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence (an exemplary sequence SEQ ID NO:1, SEQ ID NO:2, SEQ ID NO:3, or SEQ ID NO:4) to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, continuous residues ranging anywhere from 20 to the full length of an exemplary polypeptide or nucleic acid sequence of the invention, e.g., SEQ ID NO:1, SEQ ID NO:2, SEQ ID NO:3, SEQ ID NO:4, SEQ ID NO:5, are compared to a reference sequence of the same number of contiguous positions after the two sequences are optimally aligned. If the reference sequence has the requisite sequence identity to an exemplary polypeptide or nucleic acid sequence of the invention, e.g., at least 90%, 91%, 92%, 93%, 94%, 95%, 96%, 97%, 98%, 99% or more sequence identity to SEQ ID NO:1, SEQ ID NO:2, SEQ ID NO:3, or SEQ ID NO:4, that sequence is within the scope of the invention.

Motifs which can be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

10. Computer Systems and Computer Program Products

To determine and identify sequence identities, structural homologies, motifs and the like in silico, the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media can be a hard disk, a floppy disk, a magnetic tape, CD-ROM, Digital Versatile Disk (DVD), Random Access Memory (RAM), or Read Only Memory (ROM) as well as other types of other media known to those skilled in the art.

As used herein, the terms "computer," "computer program" and "processor" are used in their broadest general contexts and incorporate all such devices.

11. Inhibiting Expression of Polypeptides and Transcripts

The invention further provides for nucleic acids complementary to (e.g., antisense sequences to) the nucleic acid sequences of the invention. Antisense sequences are capable of inhibiting the transport, splicing or transcription of protein-encoding genes, e.g., the unc-93, unc-93a, unc-93b, or unc-93c polypeptides encoding nucleic acids of the invention. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind gene or message, in either case preventing or inhibiting the production or function of the protein. The association can be through sequence specific hybridization. Another useful class of inhibitors includes oligonucleotides which cause inactivation or cleavage of protein message. The oligonucleotide can have enzyme activity which causes such cleavage, such as ribozymes. The oligonucleotide can be chemically modified or conjugated to an enzyme or composition capable of cleaving the complementary nucleic acid. One can screen a pool of many different such oligonucleotides for those with the desired activity.

General methods of using antisense, ribozyme technology and RNAi technology, to control gene expression, or of gene therapy methods for expression of an exogenous gene in this manner are well known in the art. Each of these methods utilizes a system, such as a vector, encoding either an antisense or ribozyme transcript of a phosphatase polypeptide of the invention. The term "RNAi" stands for RNA interference. This term is understood in the art to encompass technology using RNA molecules that can silence genes. See, for example, McManus, et al. *Nature Reviews Genetics* 3: 737, 2002. In this application, the term "RNAi" encompasses molecules such as short interfering RNA (siRNA), microRNAs (mRNA), small temporal RNA (stRNA). Generally speaking, RNA interference results from the interaction of double-stranded RNA with genes.

12. Antisense Oligonucleotides

The invention provides antisense oligonucleotides capable of binding the unc-93, unc-93a, unc-93b, or unc-93c polypeptide message or binding to other polypeptides, for example, endosomal proteins involved in Toll-like receptor 3-signaling, Toll-like receptor 7-signaling, or Toll-like receptor 9-signaling activity via unc-93A, unc-93B, or unc-93C. Antisense oligonucleotides can inhibit polypeptide activity by targeting mRNA. Strategies for designing antisense oligonucleotides are well described in the scientific and patent literature, and the skilled artisan can design such oligonucleotides using the novel reagents of the invention. For example, gene walking/RNA mapping protocols to screen for effective antisense oligonucleotides are well known in the art, see, e.g., Ho, *Methods Enzymol.* 314: 168-183, 2000, describing an RNA mapping assay, which is based on standard molecular techniques to provide an easy and reliable method for potent antisense sequence selection. See also Smith, *Eur. J. Pharm. Sci.* 11: 191-198, 2000.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl)glycine units can be used. Antisense oligonucleotides having phosphorothioate linkages can also be used, as described in WO 97/03211; WO 96/39154; Mata, *Toxicol Appl Pharmacol* 144: 189-197, 1997; Antisense Therapeutics, ed. Agrawal (Humana Press, Totowa, N.J., 1996). Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and molpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense polypeptides sequences of the invention (see, e.g., Gold, *J. of Biol. Chem.* 270: 13581-13584, 1995).

13. siRNA

"Small interfering RNA" (siRNA) refers to double-stranded RNA molecules from about 10 to about 30 nucleotides long that are named for their ability to specifically interfere with protein expression through RNA interference (RNAi). Preferably, siRNA molecules are 12-28 nucleotides long, more preferably 15-25 nucleotides long, still more. Preferably 19-23 nucleotides long and most preferably 21-23 nucleotides long. Therefore, preferred siRNA molecules are 12, 13, 14, 15, 16, 17, 18, 19, 20, 21, 22, 23, 24, 25, 26, 27 28 or 29 nucleotides in length.

RNAi is a two-step mechanism (Elbashir et al., Genes Dev., 15(2): 188-200 (2001)). First, long dsRNAs are cleaved by an enzyme known as Dicer in 21-23 ribonucleotide (nt) fragments, called small interfering RNAs (siRNAs). Then, siRNAs associate with a ribonuclease complex (termed RISC for RNA Induced Silencing Complex) which target this complex to complementary mRNAs. RISC then cleaves the targeted mRNAs opposite the complementary siRNA, which makes the mRNA susceptible to other RNA degradation pathways.

siRNAs of the present invention are designed to interact with a target ribonucleotide sequence, meaning they complement a target sequence sufficiently to bind to the target sequence. The present invention also includes siRNA molecules that have been chemically modified to confer increased stability against nuclease degradation, but retain the ability to bind to target nucleic acids that may be present.

14. Inhibitory Ribozymes

The invention provides ribozymes capable of binding message which can inhibit polypeptide activity by targeting mRNA, e.g., inhibition of polypeptides with unc-93, unc-93a, unc-93b, or unc-93c activity, e.g., TLR3-, TLR7-, or TLR9- signaling activity or inhibition of endosomal proteins involved in Toll-like receptor 3-signaling, Toll-like receptor 7-signaling, or Toll-like receptor 9-signaling activity via unc-93A, unc-93B, or unc-93C. Strategies for designing ribozymes and selecting the protein-specific antisense sequence for targeting are well described in the scientific and patent literature, and the skilled artisan can design such ribozymes using the novel reagents of the invention.

Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The enzymatic ribozyme RNA molecule can be formed in a hammerhead motif, but can also be formed in the motif of a hairpin, hepatitis delta virus, group I intron or RnaseP-like RNA (in association with an RNA guide sequence). Examples of such hammerhead motifs are described by Rossi, *Aids Research and Human Retroviruses* 8: 183, 1992; hairpin motifs by Hampel, *Biochemistry* 28: 4929, 1989, and Hampel, *Nuc. Acids Res.* 18: 299, 1990; the hepatitis delta virus motif by Perrotta, *Biochemistry* 31: 16, 1992; the RnaseP motif by Guerrier-Takada, *Cell* 35: 849, 1983; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

15. Transgenic and "Knockout" Non-Human Animals

The invention provides transgenic non-human animals comprising a nucleic acid, a polypeptide, an expression cassette or vector or a transfected or transformed cell of the invention. The transgenic non-human animals can be, e.g., goats, rabbits, sheep, pigs, cows, rats and mice, comprising the nucleic acids of the invention. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA can encode mammalian kinases. Native expression in an animal can be reduced by providing an amount of antisense RNA or DNA effective to reduce expression of the receptor.

These animals can be used, e.g., as in vivo models to study Toll-like receptor 3-signaling, Toll-like receptor 7-signaling, or Toll-like receptor 9-signaling activity via unc-93A, unc-93B, or unc-93C, or, as models to screen for agents that change the TLR3-, TLR7-, or TLR9-signaling activity in vivo.

In one aspect, the inserted transgenic sequence is a sequence of the invention designed such that it does not express a functional unc-93, unc-93a, unc-93b, or unc-93c polypeptide (TLR3-, TLR7-, or TLR9-signal activating) polypeptide. The defect can be designed to be on the transcriptional, translational and/or the protein level.

The coding sequences for the polypeptides, unc-93, unc-93a, unc-93b, or unc-93c polypeptides, or 3d mutant polypeptide to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock, *J. Immunol. Methods* 231: 147-157, 1999, describing the production of recombinant proteins in the milk of transgenic dairy animals; Baguisi, *Nat. Biotechnol.* 17: 456-461, 1999, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP). One exemplary method to produce genetically altered non-human animals is to genetically modify embryonic stem cells. The modified cells are injected into the blastocoel of a blastocyst. This is then grown in the uterus of a pseudopregnant female. In order to readily detect chimeric progeny, the blastocysts can be obtained from a different parental line than the embryonic stem cells. For example, the blastocysts and embryonic stem cells can be derived from parental lines with different hair color or other readily observable phenotype. The resulting chimeric animals can be bred in order to obtain non-chimeric animals which have received the modified genes through germ-line transmission. Techniques for the introduction of embryonic stem cells into blastocysts and the resulting generation of transgenic animals are well known.

Because cells contain more than one copy of a gene, the cell lines obtained from a first round of targeting are likely to be heterozygous for the targeted allele. Homozygosity, in which both alleles are modified, can be achieved in a number of ways. In one approach, a number of cells in which one copy has been modified are grown. They are then subjected to another round of targeting using a different selectable marker. Alternatively, homozygotes can be obtained by breeding animals heterozygous for the modified allele, according to traditional Mendelian genetics. In some situations, it may be desirable to have two different modified alleles. This can be achieved by successive rounds of gene targeting or by breeding heterozygotes, each of which carries one of the desired modified alleles. See, e.g., U.S. Pat. No. 5,789,215.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci. USA* 82: 4438-4442, 1985). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia* 47: 897-905, 1991. Other procedures for introduction of DNA into tissues of animals are described in U.S. Pat. No. 4,945,050 (Sanford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice (Hammer et al., *Cell* 63: 1099-1112, 1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art (Teratocarcinomas and Embryonic Stem Cells, A Practical Approach, E. J. Robertson, ed., IRL Press, 1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination (Capecchi, *Science* 244: 1288-1292, 1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al. *Nature* 338: 153-156, 1989, the teachings of which are incorporated herein in their entirety including any drawings. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others (Houdebine and Chourrout, supra; Pursel et al., Science 244: 1281-1288, 1989; and Simms et al., Bio/Technology 6: 179-183, 1988).

16. unc-93, unc-93A unc-93B, or unc-93C Functional Knockouts

The invention provides non-human animals that do not express their endogenous unc-93, unc-93a, unc-93b, or unc-93c polypeptides, or, express their endogenous unc-93, unc-93a, unc-93b, or unc-93c polypeptides at lower than wild type levels (thus, while not completely "knocked out" their unc-93, unc-93a, unc-93b, or unc-93c activity is functionally "knocked out"). The invention also provides "knockout animals" and methods for making and using them. For example, in one aspect, the transgenic or modified animals of the invention comprise a "knockout animal," e.g., a "knockout mouse," engineered not to express an endogenous gene, e.g., an endogenous unc-93, unc-93a, unc-93b, or unc-93c gene, which is replaced with a gene expressing a polypeptide of the invention, or, a fusion protein comprising a polypeptide of the invention. Thus, in one aspect, the inserted transgenic sequence is a sequence of the invention designed such that it does not express a functional unc-93, unc-93a, unc-93b, or unc-93c (TLR3-, TLR7-, or TLR9-signal activating) polypeptide. The defect can be designed to be on the transcriptional, translational and/or the protein level. Because the endogenous unc-93, unc-93a, unc-93b, or unc-93c gene has been "knocked out," only the inserted polypeptide of the invention is expressed.

A "knock-out animal" is a specific type of transgenic animal having cells that contain DNA containing an alteration in the nucleic acid sequence that reduces the biological activity of the polypeptide normally encoded therefrom by at least 80% compared to the unaltered gene. The alteration can be an insertion, deletion, frameshift mutation, missense mutation, introduction of stop codons, mutation of critical amino acid residue, removal of an intron junction, and the like. Preferably, the alteration is an insertion or deletion, or is a frameshift mutation that creates a stop codon. Typically, the disruption of specific endogenous genes can be accomplished by deleting some portion of the gene or replacing it with other sequences to generate a null allele. Cross-breeding mammals having the null allele generates a homozygous mammals lacking an active copy of the gene.

A number of such mammals have been developed, and are extremely helpful in medical development. For example, U.S. Pat. No. 5,616,491 describes knock-out mice having suppression of CD28 and CD45. Procedures for preparation and manipulation of cells and embryos are similar to those described above with respect to transgenic animals, and are well known to those of ordinary skill in the art.

A knock out construct refers to a uniquely configured fragment of nucleic acid which is introduced into a stem cell line and allowed to recombine with the genome at the chromosomal locus of the gene of interest to be mutated. Thus, a given knock out construct is specific for a given gene to be targeted for disruption. Nonetheless, many common elements exist among these constructs and these elements are well known in the art. A typical knock out construct contains nucleic acid fragments of about 0.5 kb to about 10.0 kb from both the 5' and the 3' ends of the genomic locus which encodes the gene to be mutated. These two fragments are typically separated by an intervening fragment of nucleic acid which encodes a positive selectable marker, such as the neomycin resistance gene. The resulting nucleic acid fragment, consisting of a nucleic acid from the extreme 5' end of the genomic locus linked to a nucleic acid encoding a positive selectable marker which is in turn linked to a nucleic acid from the extreme 3' end of the genomic locus of interest, omits most of the coding sequence for the gene of interest to be knocked out. When the resulting construct recombines homologously with the chromosome at this locus, it results in the loss of the omitted coding sequence, otherwise known as the structural gene, from the genomic locus. A stem cell in which such a rare homologous recombination event has taken place can be selected for by virtue of the stable integration into the genome of the nucleic acid of the gene encoding the positive selectable marker and subsequent selection for cells expressing this marker gene in the presence of an appropriate drug.

Variations on this basic technique also exist and are well known in the art. For example, a "knock-in" construct refers to the same basic arrangement of a nucleic acid encoding a 5' genomic locus fragment linked to nucleic acid encoding a positive selectable marker which in turn is linked to a nucleic acid encoding a 3' genomic locus fragment, but which differs in that none of the coding sequence is omitted and thus the 5' and the 3' genomic fragments used were initially contiguous before being disrupted by the introduction of the nucleic acid encoding the positive selectable marker gene. This "knock-in" type of construct is thus very useful for the construction of mutant transgenic animals when only a limited region of the genomic locus of the gene to be mutated, such as a single exon, is available for cloning and genetic manipulation. Alternatively, the "knock-in" construct can be used to specifically eliminate a single functional domain of the targeted gene, resulting in a transgenic animal which expresses a polypeptide of the targeted gene which is defective in one function, while retaining the function of other domains of the encoded polypeptide. This type of "knock-in" mutant frequently has the characteristic of a so-called "dominant negative" mutant because, especially in the case of proteins which homomultimerize, it can specifically block the action of the polypeptide product of the wild-type gene from which it was derived.

Each knockout construct to be inserted into the cell must first be in the linear form. Therefore, if the knockout construct has been inserted into a vector, linearization is accomplished by digesting the DNA with a suitable restriction endonuclease selected to cut only within the vector sequence and not within the knockout construct sequence. For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

After suitable ES cells containing the knockout construct in the proper location have been identified by the selection techniques outlined above, the cells can be inserted into an embryo. Insertion can be accomplished in a variety of ways known to the skilled artisan, however a preferred method is by microinjection. For microinjection, about 10-30 cells are collected into a micropipette and injected into embryos that are at the proper stage of development to permit integration of the foreign ES cell containing the knockout construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan. After the ES cell has been introduced into the embryo, the embryo can be implanted into the uterus of a pseudopregnant foster mother for gestation as described above.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a target gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The functional unc-93, unc-93a, unc-93b, or unc-93c "knockout" non-human animals of the invention are of several types. Some non-human animals of the invention that are functional unc-93, unc-93a, unc-93b, or unc-93c "knockouts" express sufficient levels of a unc-93, unc-93a, unc-93b, or unc-93c inhibitory nucleic acid, e.g., antisense sequences or ribozymes of the invention, to decrease the levels or knockout the expression of functional polypeptide. Some non-human animals of the invention that are functional unc-93, unc-93a, unc-93b, or unc-93c "knockouts" express sufficient levels of a unc-93, unc-93a, unc-93b, or unc-93c dominant negative polypeptide such that the effective amount of free endogenous active unc-93, unc-93a, unc-93b, or unc-93c is decreased. Some non-human animals of the invention that are functional unc-93, unc-93a, unc-93b, or unc-93c "knockouts" express sufficient levels of an antibody of the invention, e.g., a unc-93, unc-93a, unc-93b, or unc-93c antibody, such that the effective amount of free endogenous active unc-93b is decreased. Some non-human animals of the invention that are functional unc-93, unc-93a, unc-93b, or unc-93c "knockouts" are "conventional" knockouts in that their endogenous unc-93, unc-93a, unc-93b, or unc-93c gene has been disrupted or mutated.

Functional unc-93, unc-93a, unc-93b, or unc-93c "knockout" non-human animals of the invention also include the inbred mouse strain of the invention and the cells and cell lines derived from these mice.

The invention provides a novel use for these non-human animals by discovering that animals that do not express sufficient levels of a unc-93, unc-93a, unc-93b, or unc-93c polypeptides have an autoimmune disease, an infectious disease, an inflammatory disease, an antigen presenting cell defect, a CD8 cell defect, or a CD4 cell defect. Thus, by using the transgenic non-human animals or inbred strains, e.g., mouse strains, of the invention the invention provides in vivo methods to identify modulators, e.g., chemical or genetic modulators, of an autoimmune disease, an infectious disease, an inflammatory disease, an antigen presenting cell defect, a CD8 cell defect, or a CD4 cell defect.

The invention provides methods for tolerizing a subject to an antigen (including, e.g., inducing humoral or cellular anergy to an immunogen). The method comprises providing an inhibitor of a unc-93, unc-93a, unc-93b, or unc-93c activity (TLR3-, TLR7-, or TLR9-signal inhibiting activity), e.g., a nucleic acid (e.g., antisense, ribozyme) or a polypeptide (e.g., antibody or dominant negative) of the invention. The inhibitor is administered in sufficient amounts to the subject to inhibit the expression of unc-93, unc-93a, unc-93b, or unc-93c polypeptides. This generates a T cell defect comprising a defective co-signal up-regulation of CD69 through CD28 signaling after TCR stimulation to generating a toleragenic signal in the subject. The antigen is then administered to the subject. This tolerizes the subject to the antigen. Methods and compositions for tolerizing subjects to antigens known in the art can be adapted to practice the methods of this invention, see, e.g., U.S. Pat. Nos. 6,245,752; 6,211,160; 6,060,056; 5,935,577; 5,856,446; 5,833,990; 4,428,965.

17. Inbred Mouse Strains

The invention provides an inbred mouse and an inbred mouse strain that can be generated as described herein and bred by standard techniques, see, e.g., U.S. Pat. Nos. 6,040, 495; 5,552,287.

In order to screen for mutations with recessive effects a number of strategies can be used, all involving a further two generations. For example, male G1 mice can be bred to wild-type female mice. The resulting progeny (G2 mice) can be interbred or bred back to the G1 father. The G3 mice that result from these crosses will be homozygotes for mutations in a small number of genes (3-6) in the genome, but the identity of these genes is unknown. With enough G3 mice, a good sampling of the genome should be present.

18. Peptides and Polypeptides

The invention provides isolated or recombinant polypeptides comprising an amino acid sequence having at least 95%, 96%, 97%, 98%, 99% or more sequence identity to SEQ ID NO:2 or SEQ ID NO:5 over a region of at least about 100, 150, 200, 250, 300, 350, 400, 450, 500, 550, 600, 650, 700, 750, 800, 850, 900, 950, 1000, 1100 or more residues, or, the full length of the polypeptide, or, a polypeptide encoded by a nucleic acid of the invention. In one aspect, the polypeptide comprises a sequence as set forth in SEQ ID NO:2 or SEQ ID NO:4. The invention provides methods for inhibiting the activity of unc-93, unc-93a, unc-93b, or unc-93c polypeptides, e.g., a polypeptide of the invention. The invention also provides methods for screening for compositions that inhibit the activity of, or bind to (e.g., bind to the active site), of unc-93, unc-93a, unc-93b, or unc-93c polypeptides, e.g., a polypeptide of the invention.

In one aspect, the invention provides unc-93, unc-93a, unc-93b, or unc-93c polypeptides (and the nucleic acids encoding them) where one, some or all of the unc-93, unc-93a, unc-93b, or unc-93c polypeptides replacement with substituted amino acids. In one aspect, the invention provides methods to disrupt the interaction of unc-93, unc-93a, unc-93b, or unc-93c polypeptides with other proteins, in antigen presentation pathways, including, but not limited to Toll like receptor signaling pathways, TLR3-, TLR7-, or TLR9-signaling pathways.

The peptides and polypeptides of the invention can be expressed recombinantly in vivo after administration of nucleic acids, as described above, or, they can be administered directly, e.g., as a pharmaceutical composition. They can be expressed in vitro or in vivo to screen for modulators of a unc-93, unc-93a, unc-93b, or unc-93c activity and for agents that can ameliorate an autoimmune disease, an infectious disease, an inflammatory disease, an antigen presenting cell defect or a CD4 cell defect. Polypeptides (e.g., antibody or dominant negative) of the invention can also be used to tolerize a subject to an antigen for, e.g., inducing humoral or cellular anergy to an immunogen.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers, *Nucleic Acids Res. Symp. Ser.* 215-223, 1980; Horn, *Nucleic Acids Res. Symp. Ser.* 225-232, 1980; Banga, A. K., Therapeutic Peptides and Proteins, Formulation, Processing and Delivery Systems Technomic Publishing Co., Lancaster, Pa., 1995. For example, peptide synthesis can be performed using various solid-phase techniques (see e.g., Roberge, *Science* 269: 202, 1995; Merrifield, *Methods Enzymol.* 289: 3-13, 1997) and automated synthesis can be achieved, e.g., using the ABI 431A Peptide Synthesizer (Perkin Elmer) in accordance with the instructions provided by the manufacturer.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, a mimetic composition is within the scope of the invention if, when administered to or expressed in a cell, it has an a TLR-3-, TLR7-, or TLR9-signaling activity. A mimetic composition can also be within the scope of the invention if it can inhibit an activity of a unc-93, unc-93a, unc-93b, or unc-93c polypeptides of the invention, e.g., be a dominant negative mutant or, bind to an antibody of the invention.

Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; K- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N=C=N—R') such as, e.g., 1-cyclohexyl-3(2-morpholin-yl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, citrulline, or (☐adioimmu)-acetic acid, or (☐adioimmu)alkyl-acetic acid, where alkyl is defined above. Nitrile derivative (e.g., containing the CN-moiety in place of COOH) can be substituted for ☐adioimmuno or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl)propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of □adioim include, e.g., pipecolic acid, thiazolidine carboxylic acid, 3- or 4-hydroxy □adioim, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of □adioim and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A component of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but which can additionally be referred to as the R— or S-form The invention also provides polypeptides that are "substantially identical" to an exemplary polypeptide of the invention. A "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for □adioimmuno). One or more amino acids can be deleted, for example, from a unc-93b polypeptide of the invention, resulting in modification of the structure of the polypeptide, without significantly altering its biological activity. For example, amino- or carboxyl-terminal, or internal, amino acids which are not required for a TLR-3-, TLR7-, or TLR9-signaling activity can be removed.

The skilled artisan will recognize that individual synthetic residues and polypeptides incorporating these mimetics can be synthesized using a variety of procedures and methodologies, which are well described in the scientific and patent literature, e.g., Organic Syntheses Collective Volumes, Gilman, et al. (Eds) John Wiley & Sons, Inc., NY. Peptides and peptide mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi, *Mol. Biotechnol.* 9: 205-223, 1998; Hruby, *Curr. Opin. Chem. Biol.* 1: 114-119, 1997; Ostergaard, *Mol. Divers.* 3: 17-27, 1997; Ostresh, *Methods Enzymol.* 267: 220-234, 1996. Modified peptides of the invention can be further produced by chemical modification methods, see, e.g., Belousov, *Nucleic Acids Res.* 25: 3440-3444, 1997; Frenkel, *Free Radic. Biol. Med.* 19: 373-380, 1995; Blommers, *Biochemistry* 33: 7886-7896, 1994.

Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams, *Biochemistry* 34: 1787-1797, 1995; Dobeli, *Protein Expr. Purif.* 12: 404-14, 1998). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll, *DNA Cell. Biol.*, 12: 441-53, 1993.

The terms "polypeptide" and "protein" as used herein, refer to amino acids joined to each other by peptide bonds or modified peptide bonds, i.e., peptide isosteres, and can contain modified amino acids other than the 20 gene-encoded amino acids. The term "polypeptide" also includes peptides and polypeptide fragments, motifs and the like. The term also includes glycosylated polypeptides. The peptides and polypeptides of the invention also include all "mimetic" and "peptidomimetic" forms, as described in further detail, below.

As used herein, the term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

An exemplary unc-93b is presented; SEQ ID NO:1 being the nucleic acid sequence, and SEQ ID NO:2 being the amino acid translation thereof. An exemplary 3d mutant of unc-93b is presented; SEQ ID NO:3 being the nucleic acid sequence, and SEQ ID NO:4 being the amino acid translation thereof.

19. Screening Methodologies

In practicing the methods of the invention, a variety of apparatus and methodologies can be used to in conjunction with the polypeptides and nucleic acids of the invention, e.g., to screen polypeptides for TLR3-, TLR7-, or TLR9-signaling activity, to screen compounds as potential modulators (e.g., inhibitors or activators) of a unc-93, unc-93a, unc-93b, or unc-93c activity, e.g., an TLR-3-, TLR7-, or TLR9-signaling activity, for antibodies that bind to a polypeptide of the invention, for nucleic acids that hybridize to a nucleic acid of the invention, to screen for cells expressing a polypeptide of the invention and the like.

In one aspect, the peptides and polypeptides of the invention can be bound to a solid support. Solid supports can include, e.g., membranes (e.g., nitrocellulose or nylon), a microtiter dish (e.g., PVC, polypropylene, or polystyrene), a test tube (glass or plastic), a dip stick (e.g., glass, PVC, polypropylene, polystyrene, latex and the like), a microfuge tube, or a glass, silica, plastic, metallic or polymer bead or other substrate such as paper. One solid support uses a metal (e.g., cobalt or nickel)-comprising column which binds with specificity to a histidine tag engineered onto a peptide.

Adhesion of peptides to a solid support can be direct (i.e., the protein contacts the solid support) or indirect (a particular compound or compounds are bound to the support and the target protein binds to this compound rather than the solid support). Peptides can be immobilized either covalently (e.g., utilizing single reactive thiol groups of cysteine residues (see, e.g., Colliuod, *Bioconjugate Chem.* 4: 528-536, 1993) or non-covalently but specifically (e.g., via immobilized antibodies (see, e.g., Schuhmann, *Adv. Mater.* 3: 388-391, 1991; Lu, *Anal. Chem.* 67: 83-87, 1995; the biotin/strepavidin system (see, e.g., Iwane, *Biophys. Biochem. Res. Comm.* 230: 76-80, 1997); metal chelating, e.g., Langmuir-Blodgett films (see, e.g., Ng, *Langmuir* 11: 4048-55, 1995); metal-chelating self-assembled monolayers (see, e.g., Sigal, *Anal. Chem.* 68: 490-497, 1996) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (SLAB) and the sulfosuccinimidyl derivatives such as sulfosuccinimidyl(4-iodoacetyl)aminobenzoate (sulfo-SIAB) (Pierce). Another group of coupling agents is the heterobifunctional and thiol cleavable agents such as N-succinimidyl 3-(2-pyridyidithio)propiona-te (SPDP) (Pierce Chemicals, Rockford, Ill.).

Antibodies can be used for binding polypeptides and peptides of the invention to a solid support. This can be done directly by binding peptide-specific antibodies to the column or it can be done by creating fusion protein chimeras comprising motif-containing peptides linked to, e.g., a known epitope (e.g., a tag (e.g., FLAG, myc) or an appropriate immunoglobulin constant domain sequence (an "immunoadhesin," see, e.g., Capon, *Nature* 377: 525-531, 1989.

20. Arrays or "Biochips"

The invention provides methods for identifying/screening for modulators (e.g., inhibitors, activators) of a unc-93, unc-93a, unc-93b, or unc-93c activity, e.g., a TLR-3-, TLR7-, or TLR9-signaling activity, using arrays. Potential modulators, including small molecules, nucleic acids, polypeptides (including antibodies) can be immobilized to arrays. Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention, e.g., a unc-93, unc-93a, unc-93b, or unc-93c activity. For example, in one aspect of the invention, a monitored parameter is transcript expression of a gene comprising a nucleic acid of the invention. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays can be used to simultaneously quantify a plurality of proteins. Small molecule arrays can be used to simultaneously analyze a plurality of unc-93, unc-93a, unc-93b, or unc-93c modulating or binding activities.

The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts. In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston, *Curr. Biol.* 8: R171-R174, 1998; Schummer, *Biotechniques* 23: 1087-1092, 1997; Kern, *Biotechniques* 23: 120-124, 1997; Solinas-Toldo, *Genes, Chromosomes & Cancer* 20: 399-407, 1997; Bowtell, *Nature Genetics Supp.* 21: 25-32, 1999. See also published U.S. patent applications Nos. 20010018642; 20010019827; 20010016322; 20010014449; 20010014448; 20010012537; 20010008765.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface.

21. Combinatorial Chemical Libraries

The invention provides methods for identifying/screening for modulators (e.g., inhibitors, activators) of a unc-93, unc-93a, unc-93b, or unc-93c activity, e.g., a TLR-3-, TLR7-, or TLR9-signaling activity. In practicing the screening methods of the invention, a test compound is provided. It can be contacted with a polypeptide of the invention in vitro or administered to a cell of the invention or an animal of the invention in vivo. Compounds are also screened using the compositions, cells, non-human animals and methods of the invention for their ability to ameliorate autoimmune disease, an infectious disease, an inflammatory disease, an antigen presenting cell defect or a CD4 cell defect, and, or for their ability to generate a toleragenic environment in an animal. Combinatorial chemical libraries are one means to assist in the generation of new chemical compound leads for, e.g., compounds that inhibit an TLR-3-, TLR7-, or TLR9-signaling activity or, using a transgenic or a knockout non-human animal of the invention, a compound that can be used to treat or ameliorate a an autoimmune disease, an infectious disease, an inflammatory disease, an antigen presenting cell defect or a CD4 cell defect, or to be used to tolerize a subject to an antigen.

A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, the systematic, combinatorial mixing of 100 interchangeable chemical building blocks results in the theoretical synthesis of 100 million tetrameric compounds or 10 billion pentameric compounds (see, e.g., Gallop et al. (1994) 37(9): 1233-1250). Preparation and screening of combinatorial chemical libraries are well known to those of skill in the art, see, e.g., U.S. Pat. Nos. 6,004,617; 5,985,356. Such combinatorial chemical libraries include, but are not limited to, peptide libraries (see, e.g., U.S. Pat. No. 5,010,175; Furka, *Int. J. Pept. Prot. Res.* 37: 487-493, 1991, Houghton et al. *Nature,* 354: 84-88, 1991). Other chemistries for generating chemical diversity libraries include, but are not limited to: peptoids (see, e.g., WO 91/19735), encoded peptides (see, e.g., WO 93/20242), random bio-oligomers (see, e.g., WO 92/00091), benzodiazepines (see, e.g., U.S. Pat. No. 5,288,514), diversomers such as hydantoins, benzodiazepines and dipeptides (see, e.g., Hobbs, *Proc. Nat. Acad. Sci. USA* 90: 6909-6913, 1993), vinylogous polypeptides (see, e.g., Hagihara, *J. Amer. Chem. Soc.* 114: 6568, 1992), non-peptidal peptidomimetics with a Beta-D-Glucose scaffolding (see, e.g., Hirschmann, *J. Amer. Chem. Soc.* 114: 9217-9218, 1992), analogous organic syntheses of small compound libraries (see, e.g., Chen, *J. Amer. Chem. Soc.* 116: 2661, 1994), oligocarbamates (see, e.g., Cho, *Science* 261: 1303, 1993), and/or peptidyl phosphonates (see, e.g., Campbell, *J. Org. Chem.* 59: 658, 1994). See also Gordon, *J. Med. Chem.* 37: 1385, 1994; for nucleic acid libraries, peptide nucleic acid libraries, see, e.g., U.S. Pat. No. 5,539,083; for antibody libraries, see, e.g., Vaughn, *Nature Biotecinology* 14: 309-314, 1996; for carbohydrate libraries, see, e.g., Liang et al. *Science* 274: 1520-1522, 1996, U.S. Pat. No. 5,593,853; for small organic molecule libraries, see, e.g., for isoprenoids U.S. Pat. No. 5,569,588; for thiazolidinones and metathiazanones, U.S. Pat. No. 5,549,974; for pyrrolidines, U.S. Pat. Nos. 5,525,735 and 5,519,134; for morpholino compounds, U.S. Pat. No. 5,506,337; for benzodiazepines U.S. Pat. No. 5,288,514.

Devices for the preparation of combinatorial libraries are commercially available (see, e.g., U.S. Pat. Nos. 6,045,755; 5,792,431; 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). A number of robotic systems have also been developed for solution phase chemistries. These systems include automated workstations, e.g., like the automated synthesis apparatus developed by Taleda Chemical Industries, LTD. (Osaka, Japan) and many robotic systems utilizing robotic arms (Zymate II, Zymark Corporation, Hopkinton, Mass; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

22. Antibodies and Antibody-Based Screening Methods

The invention provides isolated or recombinant antibodies that specifically bind to a polypeptide or nucleic acid of the invention, e.g., unc-93, unc-93a, unc-93b, or unc-93c nucleic acids or polypeptides, or 3d mutant nucleic acid or polypeptide. These antibodies can be used to isolate, identify or quantify a polypeptide of the invention or related polypeptides. These antibodies can be used to isolate other polypeptides within the scope the invention or other related TLR-3-, TLR7-, or TLR9-signaling activity polypeptides.

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y., 1993; Wilson, *J. Immunol. Methods* 175: 267-273, 1994; Yarmush, *J. Biochem. Biophys. Methods* 25: 85-97, 1992. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341: 544-546, 1989), which consists of a VH domain; and (vi) an isolated complementarity determining region (CDR). Single chain antibodies are also included by reference in the term "antibody."

The antibodies can be used in immunoprecipitation, staining (e.g., FACS), immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY ($7^{th}$ ed.) Lange Medical Publications, Los Altos, Calif. ("Stites"); Goding, MONOCLONAL ANTIBODIES: PRINCIPLES AND PRACTICE (2d ed.) Academic Press, New York, N.Y., 1986;

Kohler, *Nature* 256: 495, 1975; Harlow, ANTIBODIES, A LABORATORY MANUAL, Cold Spring Harbor Publications, New York, 1988. Antibodies also can be generated in vitro, e.g., using recombinant antibody binding site expressing phage display libraries, in addition to the traditional in vivo methods using animals. See, e.g., Hoogenboom, *Trends Biotechnol.* 15: 62-70, 1997; Katz, *Annu. Rev. Biophys. Biomol. Struct.* 26: 27-45, 1997.

Polypeptides or peptides can be used to generate antibodies which bind specifically to the polypeptides of the invention. The resulting antibodies can be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody can be determined using any of a variety of procedures familiar to those skilled in the art. For example, binding can be determined by labeling the antibody with a detectable label such as a fluorescent agent, an enzymatic label, or a radioisotope. Alternatively, binding of the antibody to the sample can be detected using a secondary antibody having such a detectable label thereon. Particular assays include ELISA assays, sandwich assays, ☐adioimmunoassay, and Western Blots.

Polyclonal antibodies generated against the polypeptides of the invention can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which can bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the invention. Alternatively, transgenic mice can be used to express humanized antibodies to these polypeptides or fragments thereof.

Antibodies generated against the polypeptides of the invention can be used in screening for similar polypeptides from other organisms and samples. In such techniques, polypeptides from the organism are contacted with the antibody and those polypeptides which specifically bind the antibody are detected. Any of the procedures described above can be used to detect antibody binding.

23. Kits

The invention provides kits comprising the compositions, e.g., nucleic acids, expression cassettes, vectors, cells, polypeptides (e.g., unc-93, unc-93a, unc-93b, or unc-93c polypeptides or TLR-3-, TLR7-, or TLR9-signaling activating polypeptides) and/or antibodies of the invention. The kits also can contain instructional material teaching the methodologies and uses of the invention, as described herein.

24. Therapeutic Applications

The compounds and modulators identified by the methods of the present invention can be used in a variety of methods of treatment. Thus, the present invention provides compositions and methods for treating an autoimmune disease, an infectious disease, an inflammatory disease, an antigen presenting cell defect or a CD4 cell defect.

Exemplary autoimmune diseases are acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, parnphigus vulgaris, Wegener's granulomatosis, membranous nephropathy, amyotrophic lateral sclerosis, tabes dorsalis, giant cell arteritis/polymyalgia, pemiciousanemia, rapidly progressive glomerulonephritis and fibrosing alveolitis.

Exemplary infectious disease, include but are not limited to, viral, bacterial, fungal, or parasitic diseases. The polypeptide or polynucleotide of the present invention can be used to treat or detect infectious agents. For example, by increasing the immune response, particularly increasing the proliferation and differentiation of B and/or T cells, infectious diseases can be treated. The immune response can be increased by either enhancing an existing immune response, or by initiating a new immune response. Alternatively, the polypeptide or polynucleotide of the present invention can also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fingi: Actinomycetales (e.g., *Corynebacterium, Mycobacterium, Norcardia*), Aspergillosis, Bacillaceae (e.g., Anthrax, *Clostridium*), Bacteroidaceae, Blastomycosis, *Bordetella, Borrelia*, Brucellosis, Candidiasis, *Campylobacter*, Coccidioidomycosis, Cryptococcosis, Dermatocycoses, Enterobacteriaceae (*Klebsiella, Salmonella, Serratia, Yersinia*), Erysipelothrix, *Helicobacter*, Legionellosis, Leptospirosis, *Listeria*, Mycoplasmatales, Neisseriaceae (e.g., Acinetobacter, Gonorrhea, Menigococcal), Pasteurellacea Infections (e.g., Actinobacillus, Heamophilus, Pasteurella), *Pseudomonas*, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

25. Formulation and Administration of Pharmaceutical Compositions

The invention provides pharmaceutical compositions comprising nucleic acids, peptides and polypeptides (including Abs) of the invention. As discussed above, the nucleic acids, peptides and polypeptides of the invention can be used to inhibit or activate expression of an endogenous unc-93, unc-93a, unc-93b, or unc-93c polypeptides. Such inhibition in a cell or a non-human animal can generate a screening modality for identifying compounds to treat or ameliorate an autoimmune disease, an infectious disease, an inflammatory disease, an antigen presenting cell defect or a CD4 cell defect. Administration of a pharmaceutical composition of the invention to a subject is used to generate a toleragenic immunological environment in the subject. This can be used to tolerize the subject to an antigen.

The nucleic acids, peptides and polypeptides of the invention can be combined with a pharmaceutically acceptable carrier (excipient) to form a pharmacological composition. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptide are known to the skilled artisan and are described in detail in the scientific and patent literature, see e.g., the latest edition of Remington's Pharmaceutical Science, Mack Publishing Company, Easton, Pa. ("Remington's").

Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. One skilled in the art would appreciate that the choice of a pharmaceutically acceptable carrier including a physiologically acceptable compound depends, for example, on the route of administration of the peptide or polypeptide of the invention and on its particular physio-chemical characteristics.

In one aspect, a solution of nucleic acids, peptides or polypeptides of the invention are dissolved in a pharmaceutically acceptable carrier, e.g., an aqueous carrier if the composition is water-soluble. Examples of aqueous solutions that can be used in formulations for enteral, parenteral or transmucosal drug delivery include, e.g., water, saline, phosphate buffered saline, Hank's solution, Ringer's solution, dextrose/saline, glucose solutions and the like. The formulations can contain pharmaceutically acceptable auxiliary substances as required to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration. The concentration of peptide in these formulations can vary widely, and will be selected primarily based on fluid volumes, viscosities, body weight and the like in accordance with the particular mode of administration selected and the patient's needs.

Solid formulations can be used for enteral (oral) administration. They can be formulated as, e.g., pills, tablets, powders or capsules. For solid compositions, conventional nontoxic solid carriers can be used which include, e.g., pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10% to 95% of active ingredient (e.g., peptide). A non-solid formulation can also be used for enteral administration. The carrier can be selected from various oils including those of petroleum, animal, vegetable or synthetic origin, e.g., peanut oil, soybean oil, mineral oil, sesame oil, and the like. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Nucleic acids, peptides or polypeptides of the invention, when administered orally, can be protected from digestion. This can be accomplished either by complexing the nucleic acid, peptide or polypeptide with a composition to render it resistant to acidic and enzymatic hydrolysis or by packaging the nucleic acid, peptide or polypeptide in an appropriately resistant carrier such as a liposome. Means of protecting compounds from digestion are well known in the art, see, e.g., Fix, *Pharm Res.* 13: 1760-1764, 1996; Samanen, *J. Pharm. Pharmacol.* 48: 119-135, 1996; U.S. Pat. No. 5,391,377, describing lipid compositions for oral delivery of therapeutic agents (liposomal delivery is discussed in further detail, infra).

Systemic administration can also be by transmucosal or transdermal means. For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. See, e.g., Sayani, *Crit. Rev. Ther. Drug Carrier Syst.* 13: 85-184, 1996. For topical, transdermal administration, the agents are formulated into ointments, creams, salves, powders and gels. Transdermal delivery systems can also include, e.g., patches.

The nucleic acids, peptides or polypeptides of the invention can also be administered in sustained delivery or sustained release mechanisms, which can deliver the formulation internally. For example, biodegradeable microspheres or capsules or other biodegradeable polymer configurations capable of sustained delivery of a peptide can be included in the formulations of the invention (see, e.g., Putney, *Nat. Biotechnol.* 16: 153-157, 1998).

For inhalation, the nucleic acids, peptides or polypeptides of the invention can be delivered using any system known in the art, including dry powder aerosols, liquids delivery systems, air jet nebulizers, propellant systems, and the like. See, e.g., Patton, *Biotechniques* 16: 141-143, 1998; product and inhalation delivery systems for polypeptide macromolecules by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the compositions of the invention in vesicles composed of substances such as proteins, lipids (for example, liposomes, see below), carbohydrates, or synthetic polymers (discussed above). For a general discussion of pharmacokinetics, see, e.g., Remington's, Chapters 37-39.

The nucleic acids, peptides or polypeptides of the invention can be delivered alone or as pharmaceutical compositions by any means known in the art, e.g., systemically, regionally, or locally (e.g., directly into, or directed to, a tumor); by intraarterial, intrathecal (IT), intravenous (IV), parenteral, intrapleural cavity, topical, oral, or local administration, as subcutaneous, intra-tracheal (e.g., by aerosol) or transmucosal (e.g., buccal, bladder, vaginal, uterine, rectal, nasal mucosa). Actual methods for preparing administrable compositions will be known or apparent to those skilled in the art and are described in detail in the scientific and patent literature, see e.g., Remington's. For a "regional effect," e.g., to focus on a specific organ, one mode of administration includes intraarterial or intrathecal (IT) injections, e.g., to focus on a specific organ, e.g., brain and CNS (see e.g., Gurun, *Anesth Analg.* 85: 317-323, 1997). For example, intra-carotid artery injection if preferred where it is desired to deliver a nucleic acid, peptide or polypeptide of the invention directly to the brain. Parenteral administration is a preferred route of delivery if a high systemic dosage is needed. Actual methods for preparing parenterally administrable compositions will be known or apparent to those skilled in the art and are described in detail, in e.g., Remington's, See also, Bai, *J. Neuroimmunol.* 80: 65-75, 1997; Warren, *J. Neurol. Sci.* 152: 31-38, 1997; Tonegawa, *J. Exp. Med.* 186: 507-515, 1997.

In one aspect, the pharmaceutical formulations comprising nucleic acids, peptides or polypeptides of the invention are incorporated in lipid monolayers or bilayers, e.g., liposomes, see, e.g., U.S. Pat. Nos. 6,110,490; 6,096,716; 5,283,185; 5,279,833. The invention also provides formulations in which water soluble nucleic acids, peptides or polypeptides of the invention have been attached to the surface of the monolayer or bilayer. For example, peptides can be attached to hydrazide-PEG-(distearoylphosphatidyl) ethanolamine-containing liposomes (see, e.g., Zalipsky, *Bioconjug. Chem.* 6: 705-708, 1995). Liposomes or any form of lipid membrane, such as planar lipid membranes or the cell membrane of an intact cell, e.g., a red blood cell, can be used. Liposomal formulations can be by any means, including administration intravenously, transdermally (see, e.g., Vutla, *J. Pharm. Sci.* 85: 5-8, 1996), transmucosally, or orally. The invention also provides pharmaceutical preparations in which the nucleic acid, peptides and/or polypeptides of the invention are incorporated within micelles and/or liposomes (see, e.g., Suntres, *J. Pharm. Pharmacol.* 46: 23-28, 1994; Woodle, *Pharm. Res.* 9: 260-265, 1992). Liposomes and liposomal formulations can be prepared according to standard methods and are also well known in the art, see, e.g., Remington's; Akimaru, *Cytokines Mol. Ther.* 1: 197-210, 1995; Alving, *Immunol. Rev.* 145: 5-31, 1995; Szoka, *Ann. Rev. Biophys. Bioeng.* 9: 467, 1980, U.S. Pat. Nos. 4,235,871, 4,501,728 and 4,837, 028.

The pharmaceutical compositions are generally formulated as sterile, substantially isotonic and in full compliance with all Good Manufacturing Practice (GMP) regulations of the U.S. Food and Drug Administration.

26. Treatment Regimens: Pharmacokinetics

The pharmaceutical compositions of the invention can be administered in a variety of unit dosage forms depending upon the method of administration. Dosages for typical nucleic acid, peptide and polypeptide pharmaceutical compositions are well known to those of skill in the art. Such dosages are typically advisorial in nature and are adjusted depending on the particular therapeutic context, patient tolerance, etc. The amount of nucleic acid, peptide or polypeptide adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton, *Peptides* 18: 1431-1439, 1997; Langer, *Science* 249: 1527-1533, 1990.

In therapeutic applications, compositions are administered to a patient suffering from autoimmune disease, an infectious disease, an inflammatory disease, an antigen presenting cell defect or a CD4 cell defect in an amount sufficient to at least partially arrest the condition or a disease and/or its complications. For example, in one aspect, a soluble peptide pharmaceutical composition dosage for intravenous (IV) administration would be about 0.01 mg/hr to about 1.0 mg/hr administered over several hours (typically 1, 3, or 6 hours), which can be repeated for weeks with intermittent cycles. Considerably higher dosages (e.g., ranging up to about 10 mg/ml) can be used, particularly when the drug is administered to a secluded site and not into the blood stream, such as into a body cavity or into a lumen of an organ, e.g., the cerebrospinal fluid (CSF).

The invention will be further described with reference to the following examples; however, it is to be understood that the invention is not limited to such examples.

EXEMPLARY EMBODIMENTS

Example 1

Figure 1B:
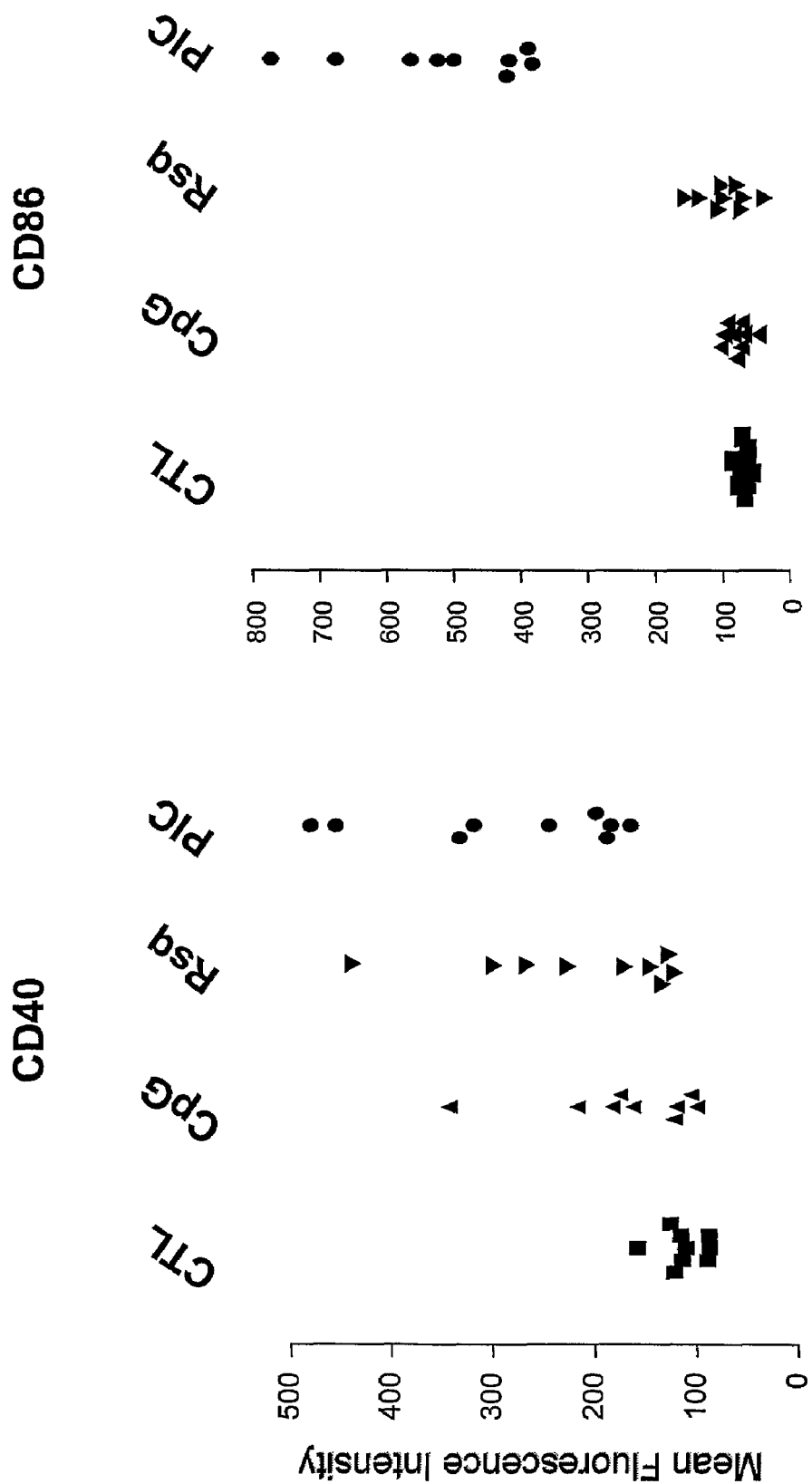

By screening macrophages derived from C57BL/6 mice homozygous for ENU-induced germline mutations, we identified two G3 animals of a single kindred that failed to produce normal quantities of TNF in response to poly-I:C (a TLR3-selective stimulus), resiquimod (a TLR7-selective stimulus), and unmethylated DNA oligonucleotides bearing CpG motifs (CpG-ODN; a TLR9-selective stimulus). These mice were bred to produce a homozygous mutant stock, which permitted phenotypic characterization of a larger number of homozygotes and obligate heterozygotes. The mutant phenotype, called "Triple D" (3d) to denote a triple defect in nucleic acid sensing, was strictly recessive, 100% penetrant, and specific for the detection of nucleic acids (FIG. 1a). Normal sensing of LPS, lipoteichoic acid, and both di- and tri-acylated bacterial lipopeptides was observed. Not only TNF production, but also the induction of costimulatory molecule expression was abolished by the 3d mutation (FIG. 1b). However, some residual response to poly-I:C was evident in this latter assay, consistent with the previous observation that a Toll/IL-1 receptor/resistance motif (TIR)-independent pathway for dsRNA sensing exists in C57BL/6 mice. Hoebe, K. et al., *Nature Immunology* 4: 1223-1229, 2003. Notably, 3d homozygotes had normally developed lymphoid organs, and showed normal numbers of peripheral CD4 and CD8 T cells, B cells, NK cells, and NKT cells. They also express normal levels of both class I and class II MHC antigens on the surface of antigen presenting cells.

The 3d phenotype is partly mimicked by treating cells with chloroquine prior to stimulation (not shown). However, careful analysis of endosome pH in macrophages and dendritic cells disclosed normal acidification of numerous endosome compartments as well as the Golgi bodies of 3d mice.

FIG. 1 shows TLR3, TLR7 and TLR9 signaling are prevented by the 3d mutation, which has no effect on endosome pH. (a) Mice were injected intraperitoneally with 3% thioglycolate. After 3 days macrophages were isolated and cultured at a density of $5 \times 10^5$ cells per well in 96-well plates with varying concentrations of the TLR-dependent inducers poly I:C; Resiquimod (Res); CpG-oligodeoxynucleotide (CpG); lipopolysaccharide (LPS); the bacterial lipopeptide $PAM_3CysSer(Lys)_4$ (LP); and peptidoglycan/lipoteichoic acid preparation (PGN/LTA). After 4 h of incubation at 37° C., media were collected for TNF-α bioassay (L-929 cytolysis). Values represent means±s.e.m (n=6 mice). (b) TLR3, 7 and 9-induced costimulatory molecule expression is inhibited in 3d homozygotes. Each point represents measurements on macrophages from a single mouse. Blue points, 3d/3d; red points, 3d/+. Peritoneal macrophages were incubated with inducers (CpG, Rsq, PIC) for 24 hours or left uninduced (CTL). CD40 and CD86 expression was analyzed by FACS.

Example 2

Since mutations that affect signaling via the TLR3 and TLR9 pathways are known to enhance susceptibility to mouse cytomegalovirus (MCMV), a β-herpesvirus to which C57BL/6 mice normally show robust resistance, we examined the susceptibility of 3d homozygotes. Hoebe, K. et al., *Nature* 424: 743-748, 2003; Tabeta, K. et al., *Proc. Natl Acad. Sci. U.S.A.* 101: 3516-3521, 2004. All animals inoculated with $10^5$ pfu of MCMV died within five days, and showed approximately 10,000-fold higher titres of the virus in splenic homogenates than C57BL/6 control animals (comparable to BALB/c mice, which are MCMV susceptible). Moreover, 3d homozygotes do not mount an adequate cytokine response to MCMV in vivo (FIG. 2a-2f). The short time frame within which death results from MCMV infection indicates that an innate immune defect is produced by 3d. Innate responses to other microbes were also impaired. For example, production of TNF and IL-12p40 mRNA in response to *Listeria monocytogenes*, processes that are known to be MyD88-dependent, were diminished, most strikingly when organisms incapable of escaping from the endosome were used to infect macrophages (the hly mutant, which lacks the listerolysin protein; FIG. 2g-h). Edelson, B. T. and Unanue, E. R. *J. Immunol.* 169: 3869-3875, 2002; McCaffrey, R. L. et al., *Proc. Natl. Acad. Sci U.S.A* 101: 11386-11391, 2004; Serbina, N. V. et al., *Immunity* 19: 891-901, 2003. Notably, when macrophages were infected by hly mutant *L. monocytogenes*, they produced far more IL-12p40 mRNA than macrophages infected by wild type *L. monocytogenes* organisms which efficiently escape from the endosome, indicating that a stronger signal was generated as a result of endosomal confinement. But this signal was nullified if the host was homozygous for the 3d mutation. 3d homozygotes were also less capable of eliminating a *Staphylococcus aureus* infection (FIG. 5).

FIG. 2 shows susceptibility to infection in 3d homozygotes. (a) Splenic viral titers were determined by plaque-forming assay 4 days after inoculation with $5 \times 10^5$ pfu of MCMV. N refers to the number of mice in each group.

BALB/c mice were used as a positive control for susceptibility. (b) Mortality following i.p. inoculation with 5×10⁵ pfu of MCMV. P value refers to the comparison between 3d/3d and +/+ mice. (c), (d), (e), and (f), concentrations of interferon-γ, IL-12, TNF-α, and type I interferon, respectively, in plasma 36h after inoculation with MCMV (5×10⁵ pfu, i.p). Interferon-γ, IL-12, and TNF-α were measured by ELISA; type I interferon activity was measured by biological assay (inhibition of VSV plaque formation). N indicates the number of mice. Error bars indicate s.e.m. (g) and (h), primary bone-marrow derived macrophages from 3d/3d mutant mice show decreased expression of IL-12p40 and TNFα after infection with *Listeria monocytogenes*. mRNA encoding IL-12p40 and TNF-α, respectively, in macrophages from C57BL/6 or 3d mutant mice infected with wildtype or hly mutant *Listeria monocytogenes*. Measurements were performed by real-time PCR six hours after infection (or stimulation with PAM₃CSK₄). Results are presented as a mean of three independent experiments±s.d.

FIG. 5 shows 3d homozygous mutant mice are unable to contain Gram-positive *S. aureus* infection. (a) Wild type C57BL/6 mice and homozygous 3d mice were each injected intravenously with luminescent *S. aureus* (10⁸ c.f.u.ml⁻¹). 3d homozygous mice showed apparent higher bacterial growth compared to that of wild type control animals at day 2 post injection. The bacterial growth is depicted as luminescent intensity. (b) Real-time monitoring of *S. aureus* growth with Xenogen IVIS imaging system. (c) Heat-killed *S. aureus* induced TNFα production of macrophages isolated from wild-type and 3d homozygotes. (d) Survival of wild type C57BL/6 mice, 3d/3d and Tlr2⁻/⁻ mice after intravenous administration of *S. aureus* (10⁸ c.f.u.ml⁻¹).

Example 3

Figure 3A:
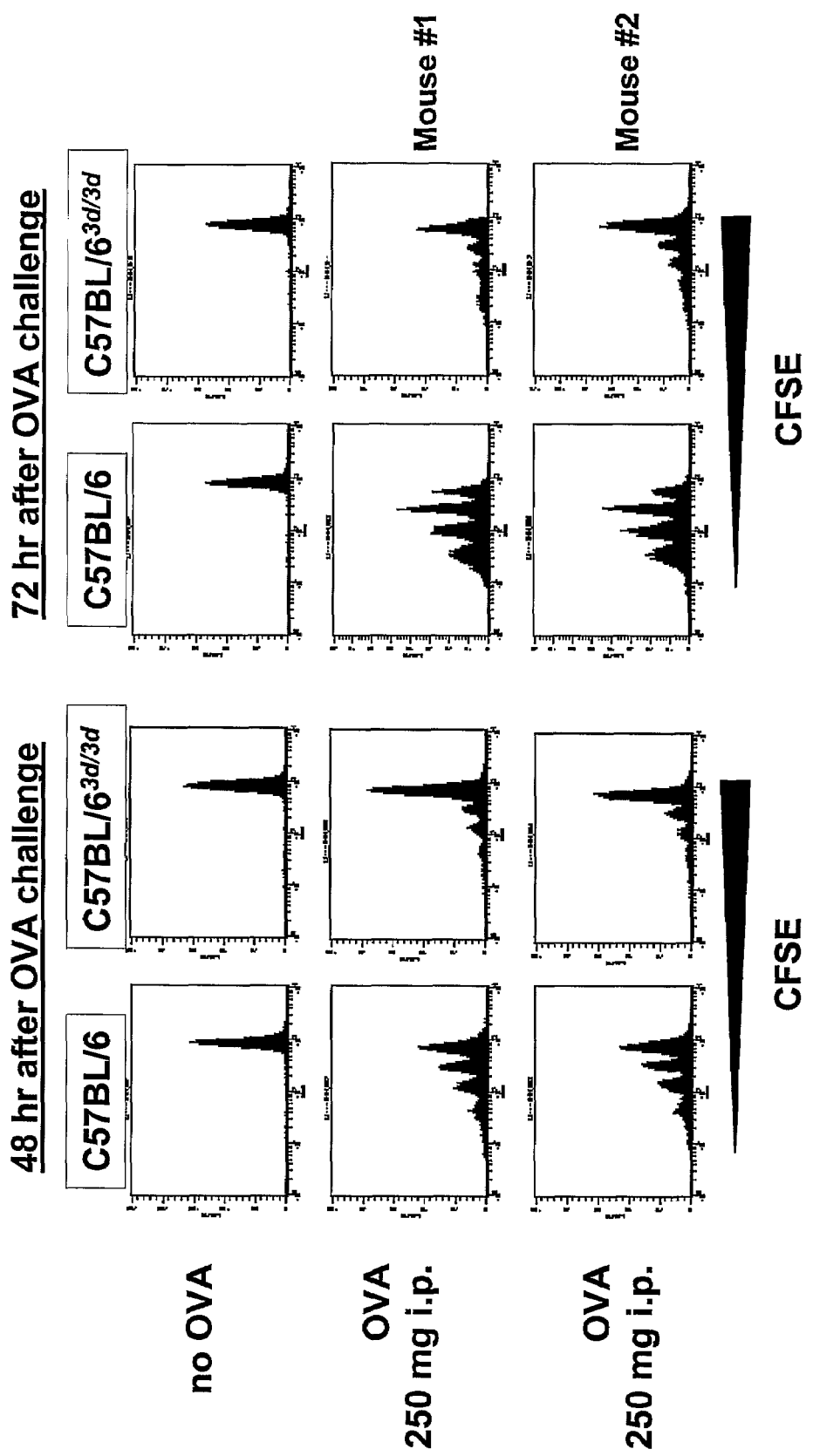
FIGS. 3A, 3B, 3C show 3d homozygous mice show defective ability to present antigen.

Quite apart from the defects described above, 3d homozygotes also fail to process antigen normally. When 3d homozygotes are injected with CFSE-labeled OT-2 cells (CD4 T-cells from a C57BL/6 mouse transgenic for a rearranged T-cell receptor that recognizes ovalbumin [OVA]) and subsequently challenged with highly pure OVA, a diminished OT-2 mitogenic response is observed in vivo. Hence, class II antigen presentation is much reduced, though not entirely abolished in the 3d environment (FIG. 3a). Cross presentation of OVA for class I activation is also inhibited by the 3d mutation. 3d homozygotes and C57BL/6 control mice were immunized with UV-irradiated C57BL/6 splenocytes expressing OVA (which as shown elsewhere, elicit an adaptive immune response that is entirely independent of TLR signaling; Hoebe, et al., concurrently submitted). Their spleens were harvested seven days later, and splenocytes were re-stimulated with class I-specific OVA peptide in vitro. The 3d homozygotes produced no OVA peptide-specific CD8⁺, IFNγ⁺ cells, and their cells showed no cytolytic activity against peptide antigen-loaded targets (FIG. 3b).

Figure 3C:
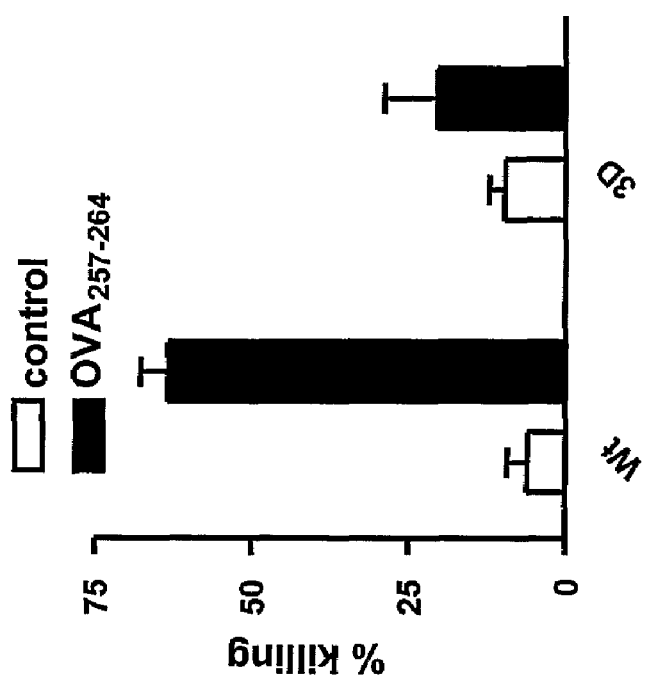
Figure 3B:
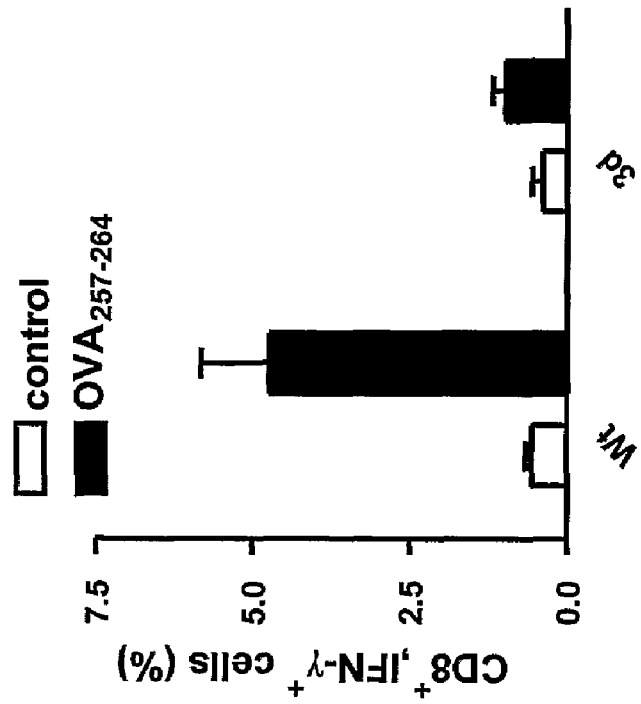

FIG. 3 shows 3d homozygous mice show defective ability to present antigen. (a) Class II MHC presentation is impaired in C57BL/6$^{3d/3d}$ mice in vivo. 3d homozygous mice received CFSE-labeled Va2⁺CD4⁺ OT-2 cells intravenously, and were then challenged with 0.25 mg of chicken ovalbumin (OVA), freshly prepared from egg white and free of microbial contaminants. Division of antigen-specific Va2⁺CD4⁺ cells was measured in the spleen 48 hrs and 72 hrs later. Results of experiments performed on two mutant mice and two wildtype mice are shown. (b), (c) Cross presentation of ovalbumin for class I activation is inhibited by the 3d mutation. 3d homozygotes and C57BL/6 control mice were immunized with UV-irradiated C57BL/6 splenocytes expressing OVA. 7 days later, splenocytes were re-stimulated with class I-specific OVA peptide in vitro or left unstimulated (control). Cross presentation was evaluated by determining the number of OVA peptide-specific CD8⁺IFN-γ⁺ cells and the cytolytic activity against OVA peptide-loaded targets (effector:target ratio 100:1).

Example 4

Figure 4A:
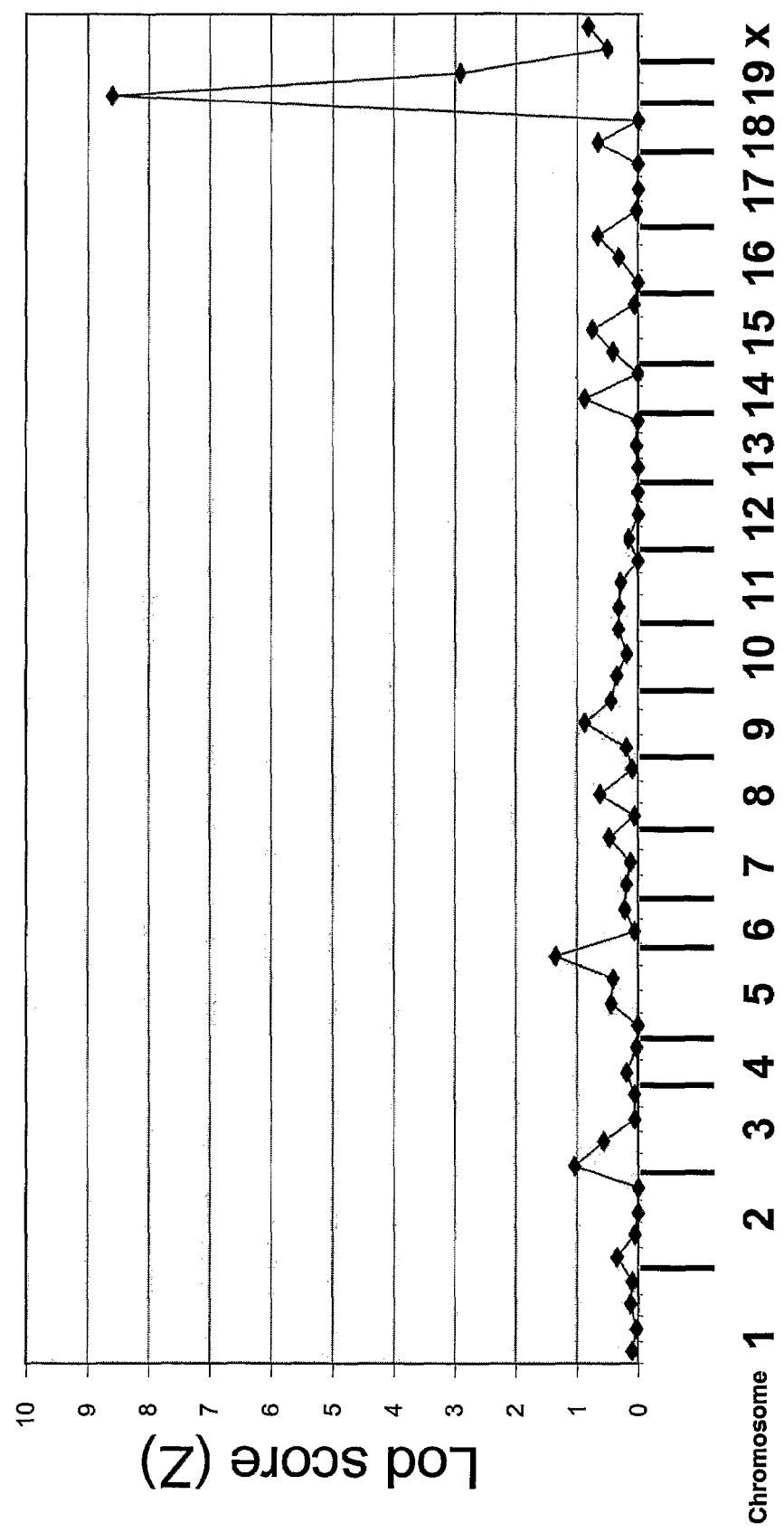
FIGS. 4A, 4B, and 4C show positional cloning of the 3d mutation.
Figure 4B:
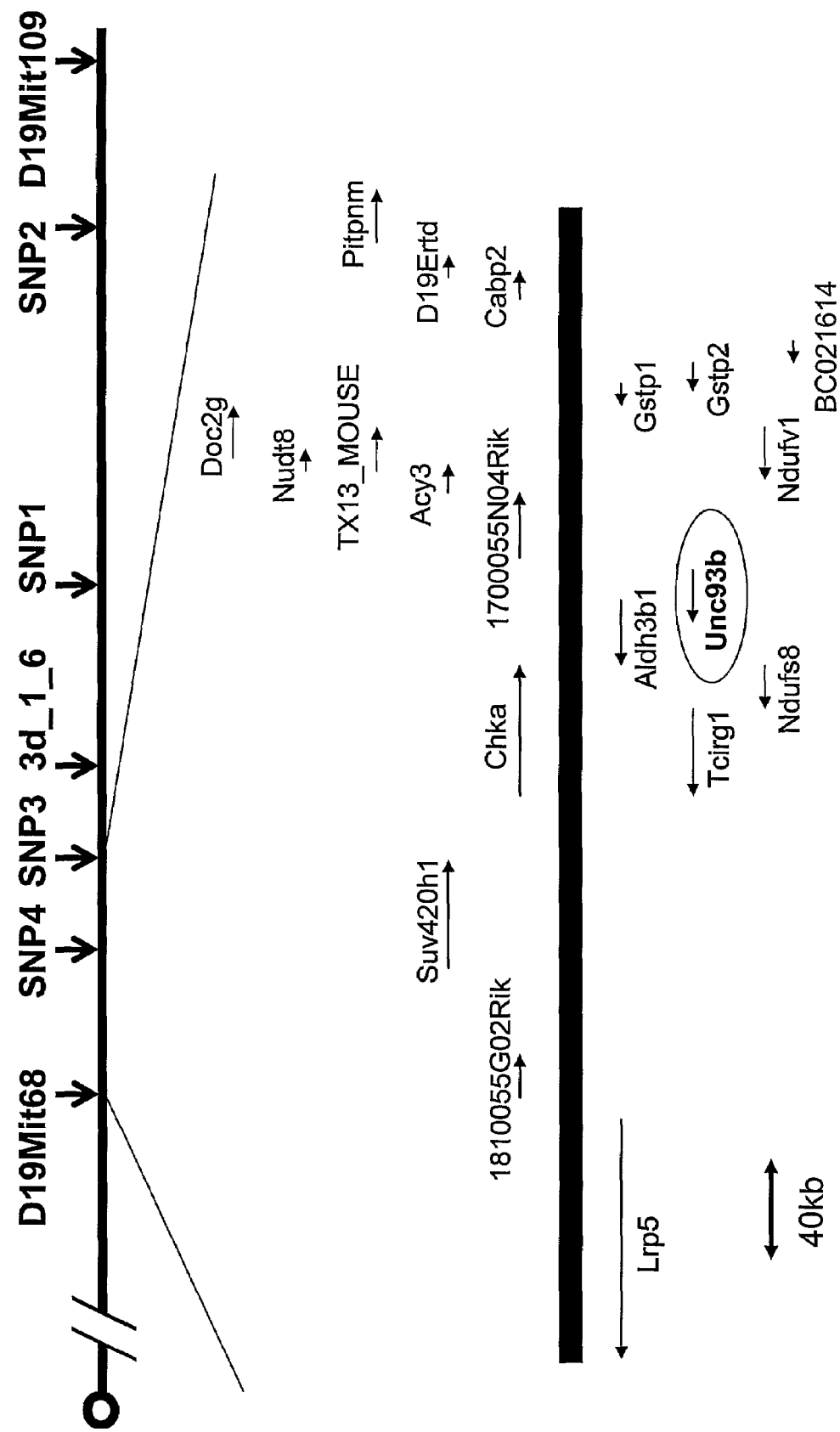
Figure 4C:
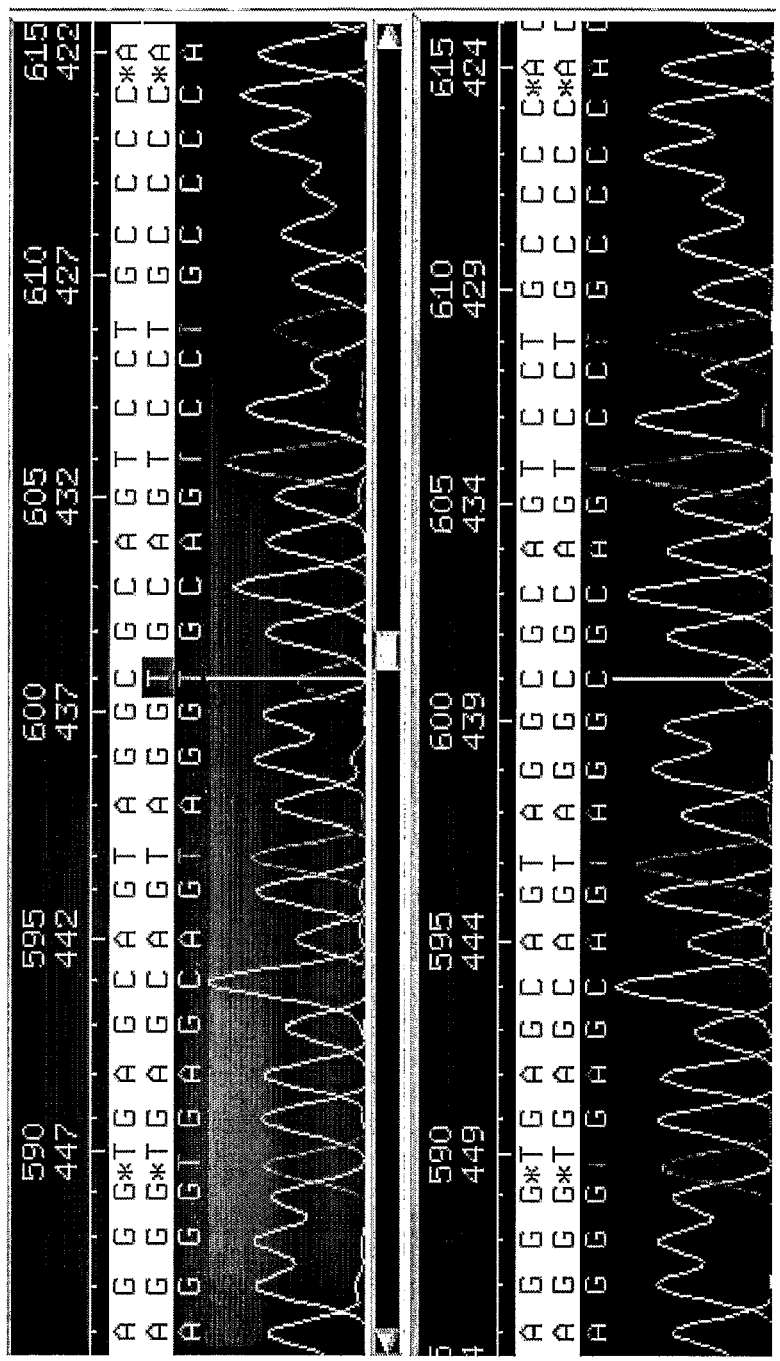
Figure 4D:
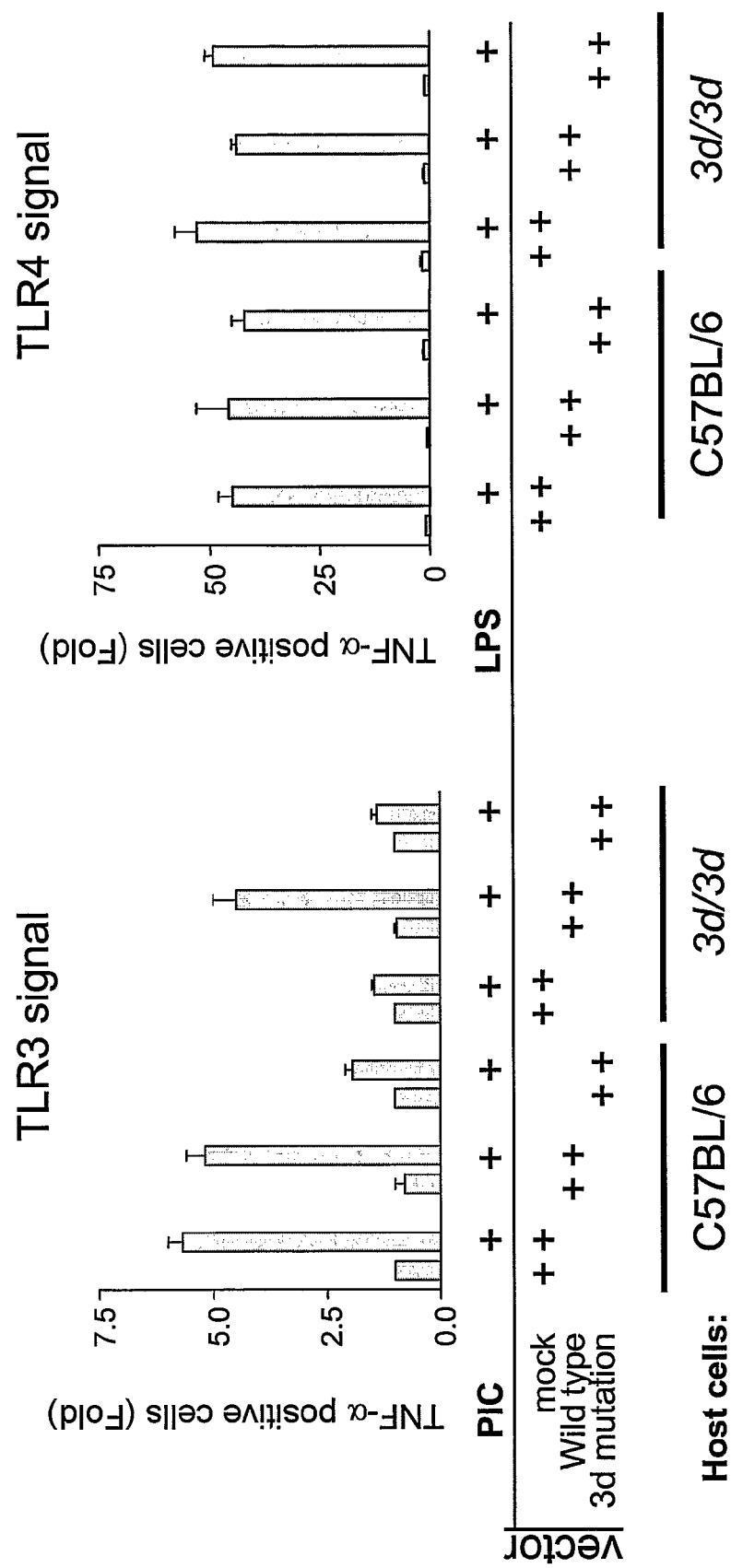
FIG. 4D shows rescue of the 3d phenotype with wildtype unc-93b.
Figure 5A:
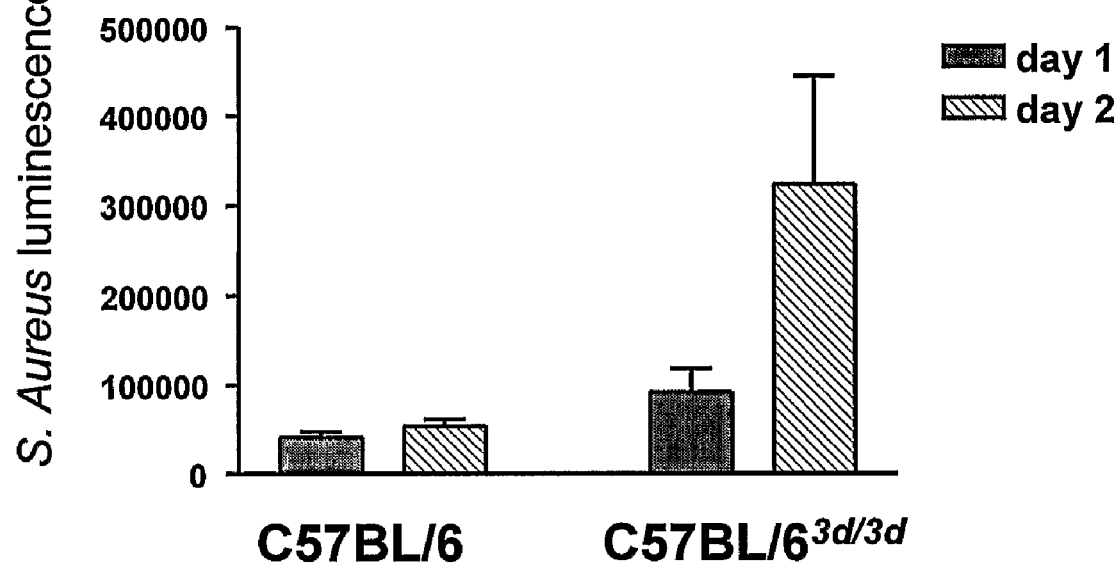
FIGS. 5A, 5B, 5C, 5D show 3d homozygous mutant mice are unable to contain Gram-positive *S. aureus* infection.
Figure 5B:
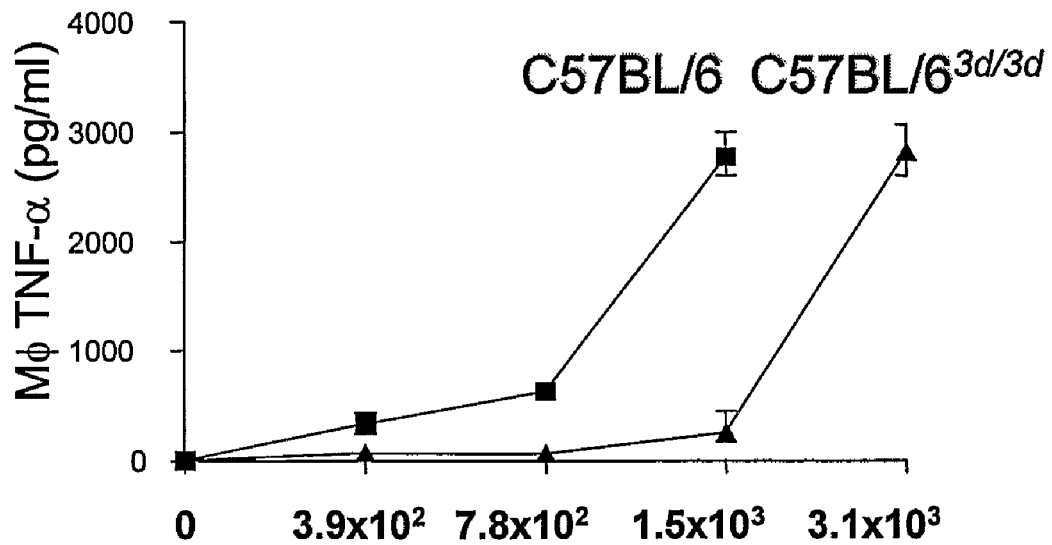
Figure 5C:
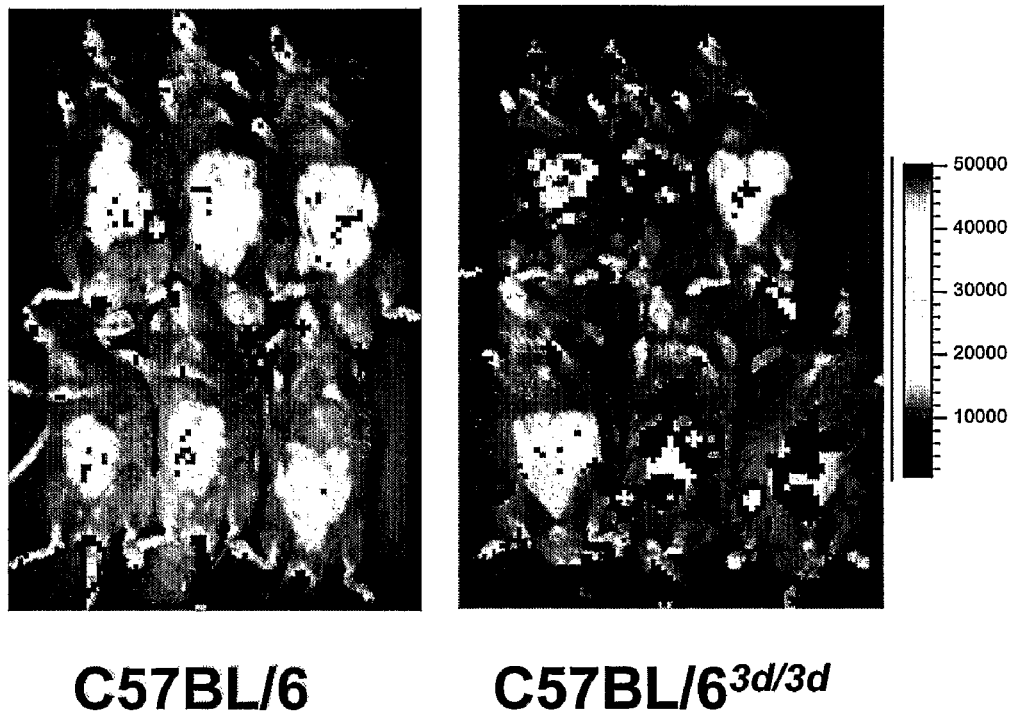
Figure 5D:
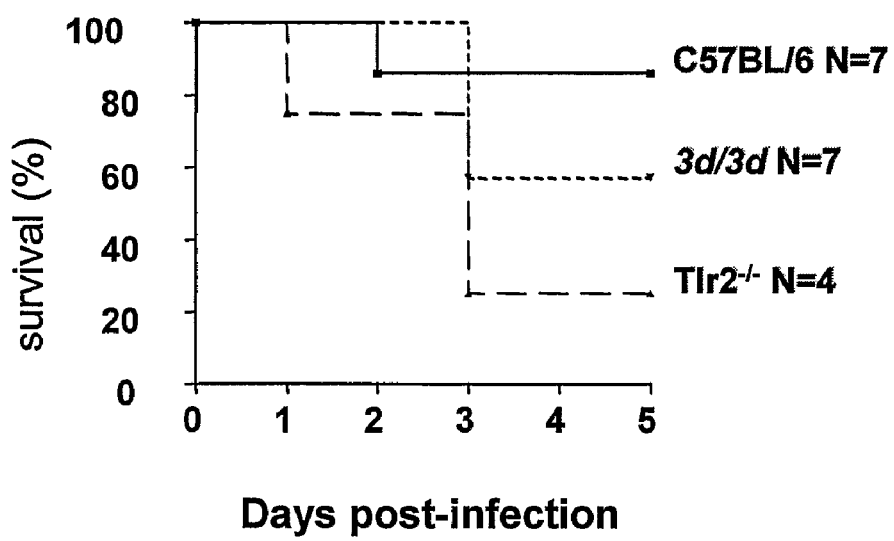
Figure 6:
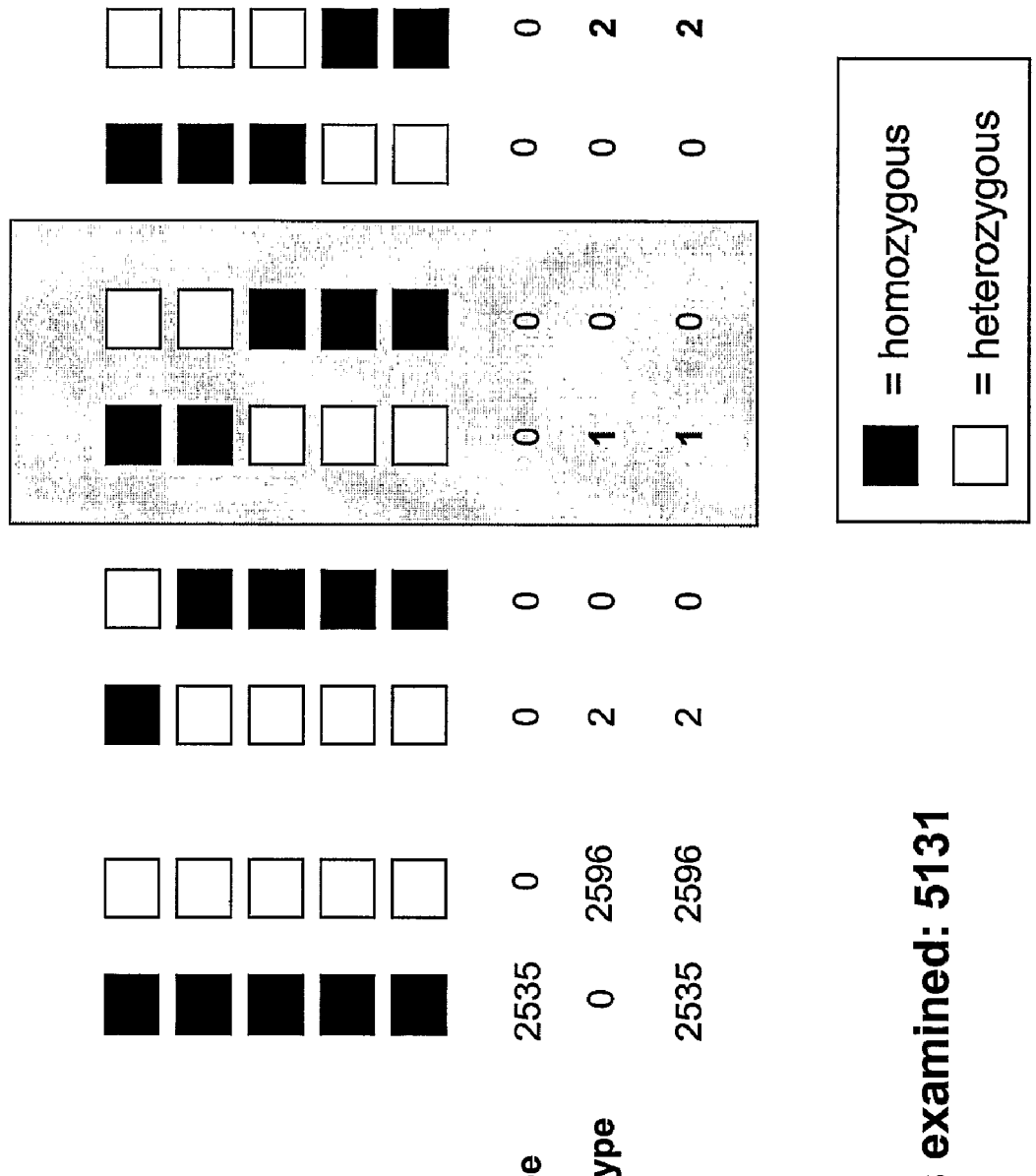
FIG. 6 shows fine genetic mapping of 3d region.

The 3d locus was genetically mapped by outcrossing the mutant stock to C3H/HeN mice and backcrossing and intercrossing the offspring. On 45 meioses, the locus was assigned to proximal chromosome 19 with a peak LOD score of 8.6 (FIG. 4a), and on 5131 meioses, the locus was confined to a chromosomal interval 0.45 Mb in length (between 0.52 and 0.97 Mb from the centromere; Ensembl distances, release 27.33c.1). One crossover separated the mutation from the proximal marker D19Mit68, and two crossovers separated the mutation from the distal marker D19SNP3 (FIG. 6). Each of these three crossover events was confirmed in a subsequent generation of mice. The critical region (FIG. 4b) contained 20 annotated genes. All candidates were sequenced at the cDNA level and at the level of genomic DNA, using primer pairs that amplified all annotated exons and splice junctions. One and only one mutation, a single base pair transversion, was identified within exon 9 of the 11-exon unc-93b gene, and was visualized in both genomic and cDNA templates (FIG. 4c). The mutation creates a missense allele, predicted to alter the 598 aa unc-93b protein, introducing a positively charged residue into the 9$^{th}$ of 12 predicted transmembrane domains (H412R). The residue in question is invariant among all known vertebrate unc-93b orthologs, including those of mice, rats, humans, chickens, and the green pufferfish.

By transfecting macrophages from 3d homozygotes to express the normal unc-93b cDNA sequence, the phenotypic defect (impaired nucleic acid sensing) was corrected in vitro, confirming the culpability of the missense mutation that was identified. When the mutant cDNA was overexpressed, a modest codominant effect was evident. Neither the normal nor the mutant form of the protein affected TLR4 signaling. When expressed in RAW 264.7 macrophages as a C-terminally GFP-tagged species, unc-93b co-localizes with calreticulin, suggesting that it is an endoplasmic reticulum component. No cell surface fluorescence, endosomal fluorescence, or Golgi fluorescence were observed, and no co-localization with endosomal markers was apparent.

FIG. 4 shows positional cloning and phenotype rescue of the 3d mutation. (a) Coarse microsatellite mapping of the 3d locus. Phenotypic classification was based on measurement of TNF-α production induced by CpG-ODN, Resiquimod and Poly I: C. On 59 meioses, using 58 markers informative for the C3H/HeN x C57BL/6 cross, the mutation was localized to proximal chromosome 19 with a peak LOD score of 8.7. (b) Illustration of 3d critical region. The 3d critical region is flanked by the public microsatellite marker D19Mit68 and by D19SNP3 (Celera accession #mcv24711430). Unc-93b (circled) was found identical with 3d. (c) Consed display (http://www.phrap.org/consed.html) of the mutation in unc-93b. A single base pair transition (T→C) creates H412R. (d) Rescue of the 3d phenotype reveals a mild dominant negative effect of the 3d allele. Bone marrow-derived dendritic cells from mutant or wildtype mice were transfected with a bicistronic GFP-encoding expression vector containing cDNA indicated. TNF-α positive cells were quantitated with or without PIC stimulation (10 μg/ml), LPS (10 ng/ml). Error bars indicate s.e.m. of three independent experiments.

FIG. 6 shows fine genetic mapping of 3d region. On 5131 meiosis, the mutation was confined between public microsatellite marker D19mit 68 and SNP3 (shaded box; markers and SNPs shown in table 1), and is separated by one crossover in proximal and two crossover in distal.

Example 5

In *C. elegans*, unc93 is a regulatory subunit of a tripartite potassium channel. Greenwald, I. S. and Horvitz, H. R. *Genetics* 96: 147-164, 1980; Levin, J. Z. and Horvitz, H. R. *J Cell Biol.* 117: 143-155, 1992; De, L. C. et al., *J Neurosci.* 23: 9133-9145, 2003. The other components of this channel are encoded by the genes sup-9 and sup-10. The sup-9 product is a 329 amino-acid protein with sequence similarity to the mammalian TASK family proteins: two-pore acid-sensitive potassium channels. Bayliss, D. A. et al., *Mol. Interv.* 3: 205-219, 2003. Based on genetic and biochemical arguments sup-10 and unc-93 are believed to encode essential regulatory components of the potassium channel. De, L. C. et al., *J Neurosci.* 23: 9133-9145, 2003. In the mammalian context, it might be postulated that unc-93b serves a related function; i.e., that it regulates a two-pore potassium channel. Alternatively, the protein may have assumed an entirely new function in mammals, unrelated to ion transport. Indeed, the mammalian protein exhibits only 18% amino acid identity to its *C. elegans* homologue.

Unc-93b is highly expressed in human dendritic cells, and in mouse B-cells (GNP expression anatomy database), consistent with a role in microbial sensing and antigen presentation. This pattern of expression is consistent with the phenotypic effects that we have observed in 3d homozygotes. A distant paralog of unc-93b (unc-93a) is known to exist, and its function remains to be established. SMART (Simple Modular Architecture Research Tool) indicates no domains in unc-93b that can be assigned functions with high confidence. While unc-93b is predicted to have twelve transmembrane domains, unc-93a is predicted to have ten (FIG. 7)

Example 6

Microbial sensing and the processing of exogenous antigens for cross presentation on class I MHC molecules or for class II MHC presentation both involve directional trafficking of macromolecules that initially reside in the phagosome, then the endosome, and ultimately the lysosomal compartment. While class II MHC peptide loading occurs within an acidified vesicular compartment and is believed to involve local proteolysis, class I MHC cross-presentation requires that proteins must be converted to peptides, which in turn must gain access to the ER where they become incorporated into the antigen presenting groove of class I MHC heterodimers. It is widely believed that proteolysis for cross-presentation occurs in the cytosol through the action of the proteasome, and that the transporter associated with antigen processing (TAP) complex serves as a channel for the translocation of cytosolic peptides into the ER. Nucleic acids might potentially cause TLR activation within the confines of the endosome or within the ER, though their mode of transport to the latter site, if it occurs, is not understood at present.

A single amino acid substitution within unc-93b profoundly impairs signaling via three TLRs and also impairs two biochemically distinct antigen presentation pathways. A definitive conclusion concerning the subcellular location of unc-93b must await direct antibody binding studies. However, given the existing evidence that unc-93b resides within the ER, it might potentially affect the endosome-targeted expression of class II MHC antigen or other proteins that are required for efficient class II MHC loading. Alternatively, peptide loading and surface expression of class II MHC antigen may not be an "endosome-autonomous" process, but may in some way require communication between the endosomes and the ER. The role of unc-93b in cross-presentation and nucleic acid sensing are mysterious as well, though it is quite clear that both of these processes do involve the ER. Like unc-93b itself, TLR9 is located primarily within the ER, while endocytosed DNA is routed from endosomes to tubular lysosomes. Latz, E. et al., 5: 190-198, 2004. Molecular contact between TLR9 and endocytosed DNA, which serves as its target ligand and is required for TLR9 activation, must entail co-localization of ligand and receptor within a common organelle. Bauer, S. et al., *Proc. Natl. Acad. Sci. U.S.A.* 98: 9237-9242, 2001. The data presented here suggest that activation probably occurs within the ER, since this is the site at which unc-93b apparently resides.

The 3d mutation raises a number of questions related to antigen processing, TLR signal transduction, and their relationship to one another. Whether directly or indirectly, unc-93b may be required for communication between an endocytic compartment and the ER; i.e., as a channel for macromolecules generated within the endosomes, or for vesicle trafficking, docking, or fusion. Because unc-93b is required both for innate and adaptive immune responses, it is an attractive target for pharmacologic intervention in autoimmune and/or inflammatory disease states. A full mechanistic understanding of unc-93b may also help to illuminate the evolution of exogenous antigen processing for adaptive immune responses, as it appears to be built upon a protein that is also required for innate defense.

Example 7

Structure, Expression, and Homologues of Unc93b1. Bioinformatic analyses revealed that Unc93b1 is highly expressed mouse B-cells and that its human homologue (UNC93B1) is highly expressed in dendritic cells (GNF expression anatomy database), consistent with a role in microbial sensing and antigen presentation, and with the phenotypic effects that were observed in 3d homozygotes. UNC93B1 has the Genbank accession number BC018388 and has been mapped to chromosome 19A (GeneID: 54445). In humans, a total of five proteins homolgous to unc-93B are predicted by Ensembl. Three of these (including one encoded by a very closely-linked gene and two genes located on other chromosomes) resemble truncations of unc-93B with nearly complete sequence identity. Their existence as expressed proteins has yet to be verified experimentally. In both humans and in mice, unc-93A (NCBI accession no. CAD19523) was found to be the nearest paralogue of unc-93B with a clearly divergent sequence along its entire length. Its function has not been determined. In mice, unc-93A is encoded by a gene on chromosome 17 (Unc93A; MGI:1933250). unc-93A was itself found to be homologous to a still more distant paralogue, also of unknown function (Unc93C; MGI:1917150), encoded by a gene on chromosome 11. Sureau, A. et al., *Nucleic Acids Res.* 25, 4513-4522, 1997. The existence of still other, more distant family members was not definitively excluded.

Simple Modular Architecture Research Tool (SMART) analysis disclosed no domains in unc-93B that could be assigned functions with high confidence. Between residues 124 and 189, a pFAM domain of unknown function (DUF895) was identified, and also found to be represented within unc-93A as well as the more distant paralogue mentioned above.

Example 8

The Subcellular Location of unc-93B. Since TLR3, 7, and 9 signaling, class II MHC loading, and acquisition of antigens destined for cross-presentation all occur within the endosomal/lysosomal compartment, it was anticipated that unc-93B would be a component of this organellar system. Surprisingly, however, when expressed in RAW 264.7 macrophages as a C-terminally GFP-tagged or myc-tagged species, unc-93B was found to be widely distributed, with a reticular pattern suggestive of ER localization. This was confirmed by the extensive colocalization of myc-tagged unc-93B with the ER marker, GFP-KDEL (Pearson's colocalization coefficient=0.88; p<0.01). By contrast, the distribution of unc-93B was clearly distinct from that of LAMP-1, a marker of late endosomes and lysosomes, and from the Golgi or plasma membrane.

It was then considered that the 3d mutation might exert its phenotypic effect by altering the subcellular distribution of class I and class II MHC proteins as well as TLRs 3, 7, and 9 through an effect on trafficking of these proteins. However, detailed immunolocalization studies excluded this hypothesis. Direct immunostaining of TLR9 showed it to reside within a punctate sub-plasmalemmal vesicular compartment which, in contrast to the conclusions of a previous study that employed a GFP-tagged version of the TLR9 for localization15, was clearly distinct from the ER. No redistribution of GFP-tagged unc-93B was observed in response to TLR9 or TLR3 ligands, nor was a difference in ligand uptake or distribution observed on comparisons of homozygous 3d vs wildtype cells. Ultrastructural analysis of macrophages harvested from 3d homozygotes and wildtype mice gave no added insight into the mechanism of action of unc-93B, as the cells appeared identical in all respects.

Example 9

Preliminary data indicate that the lupus-like disease that normally develops in C57BL/6 mice with homozygous for the Lpr allele of the gene encoding the Fas antigen is prevented by concurrent homozygosity for the 3d allele of Unc93b1. This provides further support for the use of unc-93B inhibitors in the treatment of systemic lupus erythematosus, the human disease modeled by mutations of the Fas antigen in mice. Not only inhibitors of unc-93B, but inhibitors that block the downstream events that depend on unc-93B (for example, inhibitors of proteases that are targeted to the endosomes by unc-93B) would be useful in this regard.

Example 10

Germline mutagenesis: ENU was obtained from Sigma and germline mutagenesis was performed as elsewhere described. Hoebe, K. et al., *Nature* 424: 743-748, 2003; Hoebe, K. et al., *J. Endotoxin Res.* 9: 250-255, 2003.

Innate immune activators and antibodies: *Salmonella minesota* Re595 LPS was obtained from Alexis. Peptidoglycan was purchased from Fluka. dsRNA (poly(I:C)) was obtained from Amersham Pharmacia Biotech. $Pam_3CysSer(Lys)_4$ was purchased from EMC microcollections GmbH Phosphorothioate-stabilized CpG-ODN (5'-TCCATGACGTTCCTGATGCT-3') was obtained from Integrated DNA Technologies. FITC-labeled antibodies against CD40 and CD86 were purchased from BD Biosciences. ELISA kits for IL-12 and INF-γ measurements were obtained from R&D systems.

TNF-α and Type I interferon assays: TNF-α assays were performed as previously described. Hoebe, K. et al., *Nature* 424: 743-748, 2003; Hoebe, K. et al., *J. Endotoxin Res.* 9: 250-255, 2003. Type I interferon assays were performed as described by Orange and Biron. Orange, J. S. and Biron, C. A. *J. Immunol.* 156: 4746-4756, 1996. Purified IFN-α (R&D systems) was used as standard.

Determination of Endosome pH

Rescue studies and expression of GFP-tagged unc-93b for localization. Rescue studies with bone marrow cells were performed as described elsewhere. Hoebe, K. et al., *Nature* 424: 743-748, 2003; Hoebe, K. et al., *J. Endotoxin Res.* 9: 250-255, 2003. unc-93b and unc-93$^{3d}$ were expressed using the vector pGFP-N (BD Biosciences). Transfected cells were identified by GFP fluorescence, and intracellular TNF staining was performed in this population using a labeled second antibody. RAW 264.7 cells were stably transfected using a vector with C-terminally GFP-tagged versions of unc-93b, and used for co-localization studies.

MCMV infection study. MCMV infection studies were performed as described previously. Tabeta, K. et al., *Proc. Natl. Acad. Sci U.S.A* 101: 3516-3521, 2004.

Infection of bone marrow-derived macrophages by *Listeria monocytogenes*. Primary bone-marrow macrophages prepared from C57BL/6 and 3d/3d mice were incubated with 100 U/ml IFNγ (Biosource) for 36 h prior to infection with *Listeria monocytogenes* w.t. strain (10403S at an MOI~5:1), isogenic Δhly strain (DP-L2161 at an MOI~100:1) or by stimulation with $Pam_3CSK_4$ (300 ng/ml, Invivogen). Six hours after infection, total RNA was extracted and reverse-transcribed using random hexamers. The levels of mRNA encoding IL-12p40 and TNFα were quantified by SYBR® Green real-time quantitative PCR using specific primers and normalized to the level of GAPDH mRNA.

Class II antigen presentation. $10^7$ CFSE-labeled $Va2^+CD4^+$ cells obtained from OT-2 mice were transferred intravenously to 3d homozygotes mice. After immunizing with 0.25 mg OVA, Class II presentation was analyzed on CFSE intensity of divided $Va2^+CD4^+$ cells 48 hrs and 72 hrs later, respectively.

Class I cross presentation. 3d homozygotes and C57BL/6 control mice were immunized with UV-irradiated $10^7$ transgenic C57BL/6 splenocytes expressing OVA under the influence of an actin promoter. 7 days later, splenocytes were harvested from the immunized mice and re-stimulated in vitro with class I-specific OVA peptide (SIINFEKL). Cross presentation was evaluated by measuring the percentage of OVA peptide-specific $CD8^+IFN^+$ cells as well as cytolytic activity against OVA peptide-loaded target cells at an effector:target ratio of 100:1.

Each recited range includes all combinations and sub-combinations of ranges, as well as specific numerals contained therein.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed:

1. An inbred mouse comprising a genome that is homozygous for a nucleic acid sequence encoding a polypeptide having at least 95% sequence identity to SEQ ID NO:4, wherein said polypeptide comprises a change in the amino acid sequence of SEQ ID NO:4 at amino acid residue number 412, wherein the mouse has a phenotype of increased susceptibility to viral or bacterial infections.

2. An inbred mouse according to claim 1, wherein the polypeptide comprises a sequence as set forth in SEQ ID NO:2.

3. A cell or cell line derived from an inbred mouse according to claim 1.

4. An in vitro method of screening for a modulator of a Toll-like receptor 3-, Toll-like receptor 7-, or Toll-like receptor 9-signaling activity, said method comprising: contacting a cell or cell line according to claim 3 with a test compound; and detecting an increase or a decrease in the amount of TNF-α production, susceptibility to viral or bacterial infection, or an Toll-like receptor 3-, Toll-like receptor 7-, or Toll-like receptor 9-induced macrophage activating activity; thereby identifying the test compound as a modulator of a Toll-like receptor 3-, Toll-like receptor 7-, or Toll-like receptor 9-signaling activity.

5. An in vivo method of screening for a modulator of a Toll-like receptor 3-, Toll-like receptor 7-, or Toll-like receptor 9-signaling activity, said method comprising: contacting a cell or cell line according to claim 3 with a test compound; and detecting an increase or a decrease in the amount of TNF-α production, susceptibility to viral or bacterial infection, or an Toll-like receptor 3-, Toll-like receptor 7-, or Toll-like receptor 9-induced macrophage activating activity; thereby identifying the test compound as a modulator of a Toll-like receptor 3-, Toll-like receptor 7-, or Toll-like receptor 9-signaling activity.

6. An in vivo method for screening for a modulator of an autoimmune disease, an infectious disease, an inflammatory disease, an antigen presenting cell defect, a CD8 cell defect, or a CD4 cell defect, said method comprising: contacting an inbred mouse according to claim 1 with a test compound; and detecting an increase or a decrease in the amount or severity of the autoimmune disease, the infectious disease, the antigen presenting cell defect, the CD8 cell defect, or the CD4 cell defect; wherein the increase or the decrease identifies the test compound as a modulator of the autoimmune disease, the infectious disease, the inflammatory disease, the antigen presenting cell defect, the CD8 cell defect, or the CD4 cell defect.

7. An in vivo method to identify a genetic modulator of an autoimmune disease, an infectious disease, an inflammatory disease, an antigen presenting cell defect, a CD8 cell defect, or a CD4 cell defect, said method comprising: inserting a test gene into one or more cells of an inbred mouse according to claim 1; and detecting an increase or a decrease in the amount or severity of the autoimmune disease, the infectious disease, the inflammatory disease, the antigen presenting cell defect, the CD8 cell defect, or the CD4 cell defect; wherein the increase or decrease identifies the test gene as a genetic modulator of the autoimmune disease, the infectious disease, the inflammatory disease, the antigen presenting cell defect, the CD8 cell defect, or the CD4 cell defect.

8. An in vivo method to identify a genetic modulator of an autoimmune disease, an infectious disease, an inflammatory disease, an antigen presenting cell defect, a CD8 cell defect, or a CD4 cell defect, said method comprising: mating a first inbred mouse according to claim 1 with a second mouse of a sex opposite of the first inbred mouse, wherein the second mouse is selected from the group consisting of an inbred mouse strain, a randomly mutagenized mouse, a transgenic mouse, and a knockout mouse; and selecting an offspring of the mating that exhibits an increase or a decrease in the amount or severity of the autoimmune disease, the infectious disease, the inflammatory disease, the antigen presenting cell defect, the CD8 cell defect, or the CD4 cell defect, thereby identifying a genetic modulator of the autoimmune disease, the infectious disease, the inflammatory disease, the antigen presenting cell defect, the CD8 cell defect, or the CD4 cell defect.

9. An in vivo method to identify a genetic modulator of an autoimmune disease, an infectious disease, an inflammatory disease, an antigen presenting cell defect, a CD8 cell defect, or a CD4 cell defect, said method comprising: (i) mating a first inbred mouse according to claim 1 with a second mouse of a sex opposite of the first inbred mouse, wherein the second mouse is a randomly mutagenized non-human animal; (ii) mating two offspring of the mating of step (i); and (iii) identifying offspring of the mating of step (ii) that carry two mutated alleles of a nucleic acid encoding unc-93A, unc-93B, or unc-93C, and that exhibit an increase or a decrease in the amount or severity of the autoimmune disease, the infectious disease, the inflammatory disease, the antigen presenting cell defect, the CD8 cell defect, or the CD4 cell defect, thereby identifying a genetic modulator of the autoimmune disease, the infectious disease, the inflammatory disease, the antigen presenting cell defect, the CD8 cell defect, or the CD4 cell defect.

10. The method of claim 9 wherein the nucleic acid encoding unc-93B has at least 90% identity with SEQ ID NO:1.

11. An in vivo method to identify a genetic modulator of an autoimmune disease, an infectious disease, an inflammatory disease, an antigen presenting cell defect, a CD8 cell defect, or a CD4 cell defect, said method comprising: (i) mating a first inbred mouse according to claim 1 with a second mouse of a sex opposite of the first inbred mouse, wherein the second mouse is a randomly mutagenized non-human animal; (ii) mating an offspring of the mating of step (i) with an inbred mouse according to claim 1; and (iii) identifying offspring of the mating of step (ii) that carry two mutated alleles of a nucleic acid encoding unc-93A, unc-93B, or unc-93C and that exhibit an increase or a decrease in the amount or severity of the autoimmune disease, the infectious disease, the inflammatory disease, the antigen presenting cell defect, the CD8 cell defect, or the CD4 cell defect, thereby identifying a genetic modulator of the autoimmune disease, the infectious disease, the inflammatory disease, the antigen presenting cell defect, the CD8 cell defect, or the CD4 cell defect.

12. The method of claim 11 wherein the nucleic acid encoding unc-93B has at least 90% identity with SEQ ID NO:1.

13. An in vivo method to identify a genetic modulator of an autoimmune disease, an infectious disease, an inflammatory disease, an antigen presenting cell defect, a CD8 cell defect, or a CD4 cell defect, said method comprising: (i) mating a first inbred mouse according to claim 1 with a second mouse of a sex opposite of the first inbred mouse, wherein the second mouse is a randomly mutagenized mouse; (ii) mating an offspring of the mating of step (i) with a randomly mutagenized mouse; and (iii) identifying offspring of the mating of step (ii) that carry a mutated allele of a nucleic acid encoding unc-93A, unc-93B, or unc-93C and that exhibit an increase or a decrease in the amount or severity of the autoimmune disease, the infectious disease, the inflammatory disease, the antigen presenting cell defect, the CD8 cell defect, or the CD4 cell defect, thereby identifying a genetic modulator of the autoimmune disease, the infectious disease, the inflammatory disease, the antigen presenting cell defect, the CD8 cell defect, or the CD4 cell defect.

14. The method of claim 13 wherein the nucleic acid encoding unc-93B has at least 90% identity with SEQ ID NO:1.

* * * * *

SEQUENCE LISTING

<160> NUMBER OF SEQ ID NOS: 10

<210> SEQ ID NO 1
<211> LENGTH: 1797
<212> TYPE: DNA
<213> ORGANISM: Artificial Sequence
<220> FEATURE:
<223> OTHER INFORMATION: Oligonucleotide

<400> SEQUENCE: 1

| | | | | | | |
|---|---|---|---|---|---|---|
| atggaggtgg | agcctccgct | ctaccctgtg | gccggggccg | cgggtcctca | agggggatgaa | 60 |
| gaccggcacg | gagttcctga | tgggccagag | gctcccttgg | acgaactcgt | gggtgcgtac | 120 |
| cccaactaca | atgaggagga | ggaagagcgc | cgctactacc | gccgcaagcg | cctcggagtg | 180 |
| gtcaagaacg | tgctggcggc | cagcacgggt | gtcacccta | cttacggcgt | ctacctgggc | 240 |
| ctcctgcaga | tgcaactgat | cctgcactat | gatgagacct | acagagaggt | gaagtatggc | 300 |
| aacatggggc | tgccggacat | cgatagcaag | atgctgatgg | gtatcaacgt | gacgcctatc | 360 |
| gctgccctgc | tctacacacc | tgtgctcatc | aggttttttg | gtaccaagtg | gatgatgttc | 420 |
| ttggctgtgg | gcatctatgc | cctctttgtc | tctaccaact | actgggaacg | ctactacacg | 480 |
| ctggtgccct | ctgctgtggc | tctgggcatg | gccattgtgc | ctctgtgggc | ctccatgggc | 540 |
| aactatatca | ccaggatgtc | ccagaagtac | tatgaatact | cccactacaa | ggagcaagat | 600 |
| gagcagggac | ctcagcagcg | cccaccacga | ggttcccacg | caccctatct | cctggttttc | 660 |
| caggccatct | tctatagctt | cttccacttg | agcttcgcgt | gtgcccagct | gcccatgatt | 720 |
| tacttcctca | caactacct | gtatgacctg | aaccacacac | tgatcaacgt | gcagagctgc | 780 |
| ggtactaaga | gccaaggcat | tctgaatggc | ttcaacaaga | cggtccttcg | gacgctgccg | 840 |
| cgcagcaaaa | accttattgt | tgtagagagc | gtgctcatgg | cggtggcctt | cttggccatg | 900 |
| ctgatggtgc | tgggcctgtg | tggagccgct | taccggccca | cggaagagat | cgacctgcgc | 960 |
| agcgtgggct | ggggcaacat | cttccagctg | cccttcaaac | acgtgcgtga | ctttcgctta | 1020 |
| cgccatctgg | tgcccttctt | tatctacagt | ggctttgagg | tgctctttgc | ctgcactggt | 1080 |
| tttgccctgg | gctacggcgt | gtgctccatg | gggctggagc | gactggcata | cctgctcata | 1140 |
| gcttacagcc | tgggtgcctc | agcctcctcg | gttctggggc | tgctgggact | gtggctgcct | 1200 |
| cgctctgtcc | cgctcgtggc | tggggcagga | ctgcgcctac | tgctcaccct | tagcctcttt | 1260 |
| ttctgggctc | ctgctcctcg | ggtcctccag | cacagttgga | tcttttactt | cgtggctgcc | 1320 |
| ctctgggtg | tgggcagcgc | cctcaacaag | accggactta | gcacactcct | gggcatccta | 1380 |
| tatgaagaca | aagagaggca | ggacttcatc | ttcaccatct | atcactggtg | gcaggccgtg | 1440 |
| gccatctttg | ttgtgtacct | gggctccagc | ttgcccatga | aggccaagct | ggcagtgttg | 1500 |
| ctggtgaccc | tggtagcagc | agcagcctca | tacctgtgga | tggagcagaa | gttgcagcaa | 1560 |
| ggattggtcc | cgcggcagcc | gcgcattccg | aagccacagc | acaaagtccg | cggctaccgc | 1620 |
| tacctggagg | aggacaactc | ggatgagagt | gacatggagg | gcgagcaggg | tcagggggac | 1680 |
| tgcgcagagg | acgaagcacc | acaggcaggg | cccctgggtg | cagagccagc | tggcccctgc | 1740 |
| cgcaagccct | gtcccatga | acaggctctg | ggtggcgatg | ggcctgagga | gcagtga | 1797 |

<210> SEQ ID NO 2
<211> LENGTH: 598
<212> TYPE: PRT
<213> ORGANISM: Artificial Sequence

```
<220> FEATURE:
<223> OTHER INFORMATION: Synthetic construct

<400> SEQUENCE: 2

Met Glu Val Glu Pro Leu Tyr Pro Val Ala Gly Ala Ala Gly Pro
1               5                   10                  15

Gln Gly Asp Glu Asp Arg His Gly Val Pro Asp Gly Pro Glu Ala Pro
                20                  25                  30

Leu Asp Glu Leu Val Gly Ala Tyr Pro Asn Tyr Asn Glu Glu Glu
            35                  40                  45

Glu Arg Arg Tyr Tyr Arg Arg Lys Arg Leu Gly Val Val Lys Asn Val
50                  55                          60

Leu Ala Ala Ser Thr Gly Val Thr Leu Thr Tyr Gly Val Tyr Leu Gly
65                  70                  75                  80

Leu Leu Gln Met Gln Leu Ile Leu His Tyr Asp Glu Thr Tyr Arg Glu
                85                  90                  95

Val Lys Tyr Gly Asn Met Gly Leu Pro Asp Ile Asp Ser Lys Met Leu
            100                 105                 110

Met Gly Ile Asn Val Thr Pro Ile Ala Ala Leu Leu Tyr Thr Pro Val
        115                 120                 125

Leu Ile Arg Phe Phe Gly Thr Lys Trp Met Met Phe Leu Ala Val Gly
130                 135                 140

Ile Tyr Ala Leu Phe Val Ser Thr Asn Tyr Trp Glu Arg Tyr Tyr Thr
145                 150                 155                 160

Leu Val Pro Ser Ala Val Ala Leu Gly Met Ala Ile Val Pro Leu Trp
                165                 170                 175

Ala Ser Met Gly Asn Tyr Ile Thr Arg Met Ser Gln Lys Tyr Tyr Glu
            180                 185                 190

Tyr Ser His Tyr Lys Glu Gln Asp Glu Gln Gly Pro Gln Gln Arg Pro
        195                 200                 205

Pro Arg Gly Ser His Ala Pro Tyr Leu Leu Val Phe Gln Ala Ile Phe
    210                 215                 220

Tyr Ser Phe Phe His Leu Ser Phe Ala Cys Ala Gln Leu Pro Met Ile
225                 230                 235                 240

Tyr Phe Leu Asn Asn Tyr Leu Tyr Asp Leu Asn His Thr Leu Ile Asn
                245                 250                 255

Val Gln Ser Cys Gly Thr Lys Ser Gln Gly Ile Leu Asn Gly Phe Asn
            260                 265                 270

Lys Thr Val Leu Arg Thr Leu Pro Arg Ser Lys Asn Leu Ile Val Val
        275                 280                 285

Glu Ser Val Leu Met Ala Val Ala Phe Leu Ala Met Leu Met Val Leu
290                 295                 300

Gly Leu Cys Gly Ala Ala Tyr Arg Pro Thr Glu Glu Ile Asp Leu Arg
305                 310                 315                 320

Ser Val Gly Trp Gly Asn Ile Phe Gln Leu Pro Phe Lys His Val Arg
                325                 330                 335

Asp Phe Arg Leu Arg His Leu Val Pro Phe Phe Ile Tyr Ser Gly Phe
            340                 345                 350

Glu Val Leu Phe Ala Cys Thr Gly Phe Ala Leu Gly Tyr Gly Val Cys
        355                 360                 365

Ser Met Gly Leu Glu Arg Leu Ala Tyr Leu Leu Ile Ala Tyr Ser Leu
370                 375                 380

Gly Ala Ser Ala Ser Ser Val Leu Gly Leu Leu Gly Leu Trp Leu Pro
385                 390                 395                 400
```

```
Arg Ser Val Pro Leu Val Ala Gly Ala Gly Leu Arg Leu Leu Leu Thr
                405                 410                 415

Leu Ser Leu Phe Phe Trp Ala Pro Ala Pro Arg Val Leu Gln His Ser
            420                 425                 430

Trp Ile Phe Tyr Phe Val Ala Ala Leu Trp Gly Val Gly Ser Ala Leu
        435                 440                 445

Asn Lys Thr Gly Leu Ser Thr Leu Leu Gly Ile Leu Tyr Glu Asp Lys
    450                 455                 460

Glu Arg Gln Asp Phe Ile Phe Thr Ile Tyr His Trp Trp Gln Ala Val
465                 470                 475                 480

Ala Ile Phe Val Val Tyr Leu Gly Ser Ser Leu Pro Met Lys Ala Lys
                485                 490                 495

Leu Ala Val Leu Leu Val Thr Leu Val Ala Ala Ala Ser Tyr Leu
            500                 505                 510

Trp Met Glu Gln Lys Leu Gln Gln Gly Leu Val Pro Arg Gln Pro Arg
        515                 520                 525

Ile Pro Lys Pro Gln His Lys Val Arg Gly Tyr Arg Tyr Leu Glu Glu
    530                 535                 540

Asp Asn Ser Asp Glu Ser Asp Met Glu Gly Glu Gln Gly Gln Gly Asp
545                 550                 555                 560

Cys Ala Glu Asp Glu Ala Pro Gln Ala Gly Pro Leu Gly Ala Glu Pro
                565                 570                 575

Ala Gly Pro Cys Arg Lys Pro Cys Pro Tyr Glu Gln Ala Leu Gly Gly
            580                 585                 590

Asp Gly Pro Glu Glu Gln
        595

<210> SEQ ID NO 3
<211> LENGTH: 1797
<212> TYPE: DNA
<213> ORGANISM: Artificial Sequence
<220> FEATURE:
<223> OTHER INFORMATION: Oligonucleotide

<400> SEQUENCE: 3
atggaggtgg agcctccgct ctaccctgtg gccggggccg cgggtcctca agggatgaa      60 gaccggcacg gagttcctga tgggccagag gctcccttgg acgaactcgt gggtgcgtac    120
cccaactaca atgaggagga ggaagagcgc cgctactacc gccgcaagcg cctcggagtg    180
gtcaagaacg tgctggcggc cagcacgggt gtcacccctt cttacggcgt ctacctgggc    240
ctcctgcaga tgcaactgat cctgcactat gatgagacct acagagaggt gaagtatggc    300
aacatggggc tgccggacat cgatagcaag atgctgatgg gtatcaacgt gacgcctatc    360
gctgccctgc tctacacacc tgtgctcatc aggttttttg gtaccaagtg gatgatgttc    420
ttggctgtgg gcatctatgc cctctttgtc tctaccaact actgggaacg ctactacacg    480
ctggtgccct gctgtgggc tctgggcatg gccattgtgc tctgtgggc tccatgggc      540 aactatatca ccaggatgtc ccagaagtac tatgaatact cccactacaa ggagcaagat    600
gagcagggac ctcagcagcg cccaccacga ggttcccacg cacccta tct cctggttttc    660 caggccatct tctatagctt cttccacttg agcttcgcgt gtgccagct gcccatgatt    720 tacttcctca caactaccct gtatgacctg aaccacacac tgatcaacgt gcagagctgc    780
ggtactaaga gccaaggcat tctgaatggc ttcaacaaga cggtccttcg acgctgccg     840 cgcagcaaaa accttattgt tgtagagagc gtgctcatgg cggtggcctt cttggccatg    900
```

-continued

```
ctgatggtgc tgggcctgtg tggagccgct taccggccca cggaagagat cgacctgcgc    960
agcgtgggct ggggcaacat cttccagctg cccttcaaac acgtgcgtga ctttcgctta   1020
cgccatctgg tgcccttctt tatctacagt ggctttgagg tgctctttgc ctgcactggt   1080
tttgccctgg gctacggcgt gtgctccatg gggctggagc gactggcata cctgctcata   1140
gcttacagcc tgggtgcctc agcctcctcg gttctgggc tgctgggact gtggctgcct    1200
cgctctgtcc cgctcgtggc tggggcagga ctgcgcctac tgctcaccct tagcctcttt   1260
ttctgggctc ctgctcctcg ggtcctccag cacagttgga tcttttactt cgtggctgcc   1320
ctctggggtg tgggcagcgc cctcaacaag accggactta gcacactcct gggcatccta   1380
tatgaagaca aagagaggca ggacttcatc ttcaccatct atcactggtg caggccgtg    1440 gccatctttg ttgtgtacct gggctccagc ttgcccatga aggccaagct ggcagtgttg   1500
ctggtgaccc tggtagcagc agcagcctca tacctgtgga tggagcagaa gttgcagcaa   1560
ggattggtcc cgcggcagcc gcgcattccg aagccacagc acaaagtccg cggctaccgc   1620
tacctggagg aggacaactc ggatgagagt gacatggagg gcgagcaggg tcaggggac    1680 tgcgcagagg acgaagcacc acaggcaggg cccctgggtg cagagccagc tggcccctgc   1740
cgcaagccct gtccctatga acaggctctg ggtggcgatg ggcctgagga gcagtga      1797
```

```
<210> SEQ ID NO 4
<211> LENGTH: 598
<212> TYPE: PRT
<213> ORGANISM: Artificial Sequence
<220> FEATURE:
<223> OTHER INFORMATION: Synthetic Construct

<400> SEQUENCE: 4

Met Glu Val Glu Pro Pro Leu Tyr Pro Val Ala Gly Ala Ala Gly Pro
1               5                   10                  15

Gln Gly Asp Glu Asp Arg His Gly Val Pro Asp Gly Pro Glu Ala Pro
            20                  25                  30

Leu Asp Glu Leu Val Gly Ala Tyr Pro Asn Tyr Asn Glu Glu Glu Glu
        35                  40                  45

Glu Arg Arg Tyr Tyr Arg Arg Lys Arg Leu Gly Val Val Lys Asn Val
    50                  55                  60

Leu Ala Ala Ser Thr Gly Val Thr Leu Thr Tyr Gly Val Tyr Leu Gly
65                  70                  75                  80

Leu Leu Gln Met Gln Leu Ile Leu His Tyr Asp Glu Thr Tyr Arg Glu
                85                  90                  95

Val Lys Tyr Gly Asn Met Gly Leu Pro Asp Ile Asp Ser Lys Met Leu
            100                 105                 110

Met Gly Ile Asn Val Thr Pro Ile Ala Ala Leu Leu Tyr Thr Pro Val
        115                 120                 125

Leu Ile Arg Phe Phe Gly Thr Lys Trp Met Met Phe Leu Ala Val Gly
    130                 135                 140

Ile Tyr Ala Leu Phe Val Ser Thr Asn Tyr Trp Glu Arg Tyr Tyr Thr
145                 150                 155                 160

Leu Val Pro Ser Ala Val Ala Leu Gly Met Ala Ile Val Pro Leu Trp
                165                 170                 175

Ala Ser Met Gly Asn Tyr Ile Thr Arg Met Ser Gln Lys Tyr Tyr Glu
            180                 185                 190

Tyr Ser His Tyr Lys Glu Gln Asp Glu Gln Gly Pro Gln Gln Arg Pro
        195                 200                 205
```

-continued

```
Pro Arg Gly Ser His Ala Pro Tyr Leu Leu Val Phe Gln Ala Ile Phe
    210                 215                 220
Tyr Ser Phe Phe His Leu Ser Phe Ala Cys Ala Gln Leu Pro Met Ile
225                 230                 235                 240
Tyr Phe Leu Asn Asn Tyr Leu Tyr Asp Leu Asn His Thr Leu Ile Asn
                245                 250                 255
Val Gln Ser Cys Gly Thr Lys Ser Gln Gly Ile Leu Asn Gly Phe Asn
                260                 265                 270
Lys Thr Val Leu Arg Thr Leu Pro Arg Ser Lys Asn Leu Ile Val Val
            275                 280                 285
Glu Ser Val Leu Met Ala Val Ala Phe Leu Ala Met Leu Met Val Leu
    290                 295                 300
Gly Leu Cys Gly Ala Ala Tyr Arg Pro Thr Glu Glu Ile Asp Leu Arg
305                 310                 315                 320
Ser Val Gly Trp Gly Asn Ile Phe Gln Leu Pro Phe Lys His Val Arg
                325                 330                 335
Asp Phe Arg Leu Arg His Leu Val Pro Phe Phe Ile Tyr Ser Gly Phe
                340                 345                 350
Glu Val Leu Phe Ala Cys Thr Gly Phe Ala Leu Gly Tyr Gly Val Cys
            355                 360                 365
Ser Met Gly Leu Glu Arg Leu Ala Tyr Leu Leu Ile Ala Tyr Ser Leu
    370                 375                 380
Gly Ala Ser Ala Ser Ser Val Leu Gly Leu Leu Gly Leu Trp Leu Pro
385                 390                 395                 400
Arg Ser Val Pro Leu Val Ala Gly Ala Gly Leu His Leu Leu Leu Thr
                405                 410                 415
Leu Ser Leu Phe Phe Trp Ala Pro Ala Pro Arg Val Leu Gln His Ser
                420                 425                 430
Trp Ile Phe Tyr Phe Val Ala Ala Leu Trp Gly Val Gly Ser Ala Leu
            435                 440                 445
Asn Lys Thr Gly Leu Ser Thr Leu Leu Gly Ile Leu Tyr Glu Asp Lys
    450                 455                 460
Glu Arg Gln Asp Phe Ile Phe Thr Ile Tyr His Trp Trp Gln Ala Val
465                 470                 475                 480
Ala Ile Phe Val Val Tyr Leu Gly Ser Ser Leu Pro Met Lys Ala Lys
                485                 490                 495
Leu Ala Val Leu Leu Val Thr Leu Val Ala Ala Ala Ser Tyr Leu
                500                 505                 510
Trp Met Glu Gln Lys Leu Gln Gln Gly Leu Val Pro Arg Gln Pro Arg
            515                 520                 525
Ile Pro Lys Pro Gln His Lys Val Arg Gly Tyr Arg Tyr Leu Glu Glu
    530                 535                 540
Asp Asn Ser Asp Glu Ser Asp Met Glu Gly Glu Gln Gly Gln Gly Asp
545                 550                 555                 560
Cys Ala Glu Asp Glu Ala Pro Gln Ala Gly Pro Leu Gly Ala Glu Pro
                565                 570                 575
Ala Gly Pro Cys Arg Lys Pro Cys Pro Tyr Glu Gln Ala Leu Gly Gly
                580                 585                 590
Asp Gly Pro Glu Glu Gln
            595
```

-continued

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 5
tccatgacgt tcctgatgct                                              20

<210> SEQ ID NO 6
<211> LENGTH: 8
<212> TYPE: PRT
<213> ORGANISM: Artificial Sequence
<220> FEATURE:
<223> OTHER INFORMATION: Synthetic construct

<400> SEQUENCE: 6

Ser Ile Ile Asn Phe Glu Lys Leu
1               5

<210> SEQ ID NO 7
<211> LENGTH: 30
<212> TYPE: DNA
<213> ORGANISM: Artificial Sequence
<220> FEATURE:
<223> OTHER INFORMATION: Oligonucleotide

<400> SEQUENCE: 7
agggtgagca gtaggcgcag tcctgcccca                                   30

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide

<400> SEQUENCE: 8
agggtgagca gtaggtgcag tcctgcccca                                   30

<210> SEQ ID NO 9
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 9
tcggaagcgg ttcatcactg actc                                         24

<210> SEQ ID NO 10
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 10
ccagcagaca gacagctcat cggaag                                       26